(12) United States Patent
Amari et al.

(10) Patent No.: US 8,492,548 B2
(45) Date of Patent: *Jul. 23, 2013

(54) ALKALOID AMINOESTER DERIVATIVES AND MEDICINAL COMPOSITIONS THEREOF

(75) Inventors: Gabriele Amari, Parma (IT); Mauro Riccaboni, Parma (IT); Stefano Bossolo, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/165,930

(22) Filed: Jun. 22, 2011

(65) Prior Publication Data

US 2011/0311458 A1 Dec. 22, 2011

(30) Foreign Application Priority Data

Jun. 22, 2010 (EP) ..................................... 10166907

(51) Int. Cl.
*C07D 221/02* (2006.01)
*A61K 31/44* (2006.01)

(52) U.S. Cl.
USPC .......................................... 546/112; 514/299

(58) Field of Classification Search
USPC .......................................... 514/299; 546/112
See application file for complete search history.

(56) References Cited

U.S. PATENT DOCUMENTS

| 2010/0035922 A1 | 2/2010 | Amari et al. |
| 2010/0173880 A1 | 7/2010 | Caligiuri et al. |
| 2011/0308519 A1* | 12/2011 | Schiaretti ................ 128/203.15 |
| 2011/0311461 A1* | 12/2011 | Amari et al. ................ 424/45 |

FOREIGN PATENT DOCUMENTS

| WO | 03/053966 | 7/2003 |
| WO | WO 2010/072338 | * 7/2010 |

OTHER PUBLICATIONS

U.S. Appl. No. 13/165,936, filed Jun. 22, 2011, Amari, et al.
U.S. Appl. No. 13/165,948, filed Jun. 22, 2011, Amari, et al.
European Search Report in Application No. 10166907.5, issued Dec. 29, 2010.
U.S. Appl. No. 13/219,109, filed Aug. 26, 2011, Amari, et al.
U.S. Appl. No. 13/232,415, Sep. 14, 2011, Amari, et al.
U.S. Appl. No. 13/303,413, Nov. 23, 2011, Amari, et al.
U.S. Appl. No. 13/729,388, filed Dec. 28, 2012, Amari, et al.

* cited by examiner

*Primary Examiner* — John Mabry
(74) *Attorney, Agent, or Firm* — Oblon, Spivak, McClelland, Maier & Neustadt, L.L.P.

(57) ABSTRACT

The present invention relates to alkaloid aminoester compounds which act as muscarinic receptor antagonists, processes for their preparation, compositions comprising them, and therapeutic uses thereof.

22 Claims, No Drawings

ALKALOID AMINOESTER DERIVATIVES AND MEDICINAL COMPOSITIONS THEREOF

CROSS REFERENCES TO RELATED APPLICATIONS

This application claims priority to European Patent Application No. 10166907.5, filed on Jun. 22, 2010, which is incorporated herein by reference in its entirety.

BACKGROUND OF THE INVENTION

1. Field of the Invention

The present invention relates to alkaloid aminoester derivatives which act as muscarinic receptor antagonists, processes for their preparation, compositions comprising them and therapeutic uses thereof.

2. Discussion of the Background

Quaternary ammonium salts acting as muscarinic (M) receptor antagonist drugs are currently used in therapy to induce bronchodilation for the treatment of respiratory diseases. Examples of well known M receptor antagonists are for instance represented by ipratropium bromide and tiotropium bromide.

Several chemical classes acting as selective M3 receptor antagonist drugs have been developed for the treatment of inflammatory or obstructive airway diseases such as asthma and chronic obstructive pulmonary disease (COPD).

Quinuclidine carbamate derivatives and their use as M3 antagonists are for instance disclosed in WO 02/051841, WO 03/053966 and WO 2008/012290, all of which are incorporated herein by reference in their entireties.

Said M and M3 receptor antagonists are currently administered through inhalation route in order to deliver the drug directly at the site of action, thus limiting the systemic exposure and any undesirable side effect due to systemic absorption. Therefore, it is highly desirable to provide M3 receptor antagonists able to act locally, while having high potency and long duration of action. Said drugs, once adsorbed, are degraded to inactive compounds which are deprived of any systemic side effects typical of muscarinic antagonists.

The co-pending application WO 2010/072338, which is incorporated herein by reference in its entirety, describes azonia-bicyclo[2.2.2]octane compounds acting as muscarinic receptor antagonists, further possessing the above therapeutically desirable characteristics.

However, there remains a need for muscarinic receptor antagonists with even further improved properties.

SUMMARY OF THE INVENTION

Accordingly, it is one object of the present invention to provide novel compounds which act as muscarinic receptor antagonists.

It is another object of the present invention to provide novel processes for producing such a compound.

It is another object of the present invention to provide novel pharmaceutical compositions which contain such a compound.

It is another object of the present invention to provide novel methods of treating and/or preventing certain diseases and conditions by administering an effective amount of such a compound.

These and other objects, which will become apparent during the following detailed description, have been achieved by the inventors' discovery that compounds characterized by the presence of a substituted oxoethyl group on the azonia-bicyclo[2.2.2]octane ring are endowed with high plasma instability and longer duration of action than the corresponding compounds devoid of such group.

Thus, the present invention provides alkaloid aminoester derivatives of general formula (I) with a substituted oxoethyl group on the azonia-bicyclo[2.2.2]octane, acting as muscarinic receptor antagonists.

In another embodiment, the present invention provides processes for the preparation of such compounds.

In another embodiment, the present invention provides pharmaceutical compositions which contain such a compound.

In another embodiment, the present invention provides methods for the treatment of respiratory disorders.

In another embodiment, the present invention provides combinations of the such a compound with other pharmaceutical active ingredients among which are, for instance, those currently used in the treatment of respiratory disorders, e.g. beta2-agonists, corticosteroids, P38 MAP kinase inhibitors, IKK2, HNE inhibitors, PDE4 inhibitor, leukotriene modulators, NSAIDs, and mucus regulators.

The compounds of the present invention thus behave as soft-drugs, since they are able to produce a more persistent bronchodilating effect in the lungs but are more consistently and rapidly transformed into inactive metabolites after passing into human plasma. This behavior gives great advantages in terms of safety.

DETAILED DESCRIPTION OF THE PREFERRED EMBODIMENTS

In particular, the invention is directed to alkaloid aminoester derivatives of general formula (I):

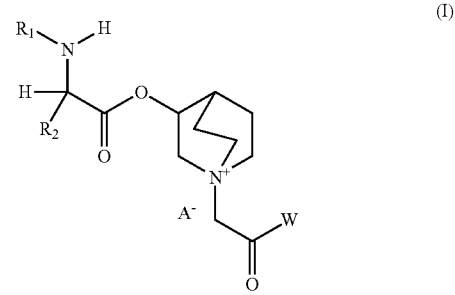

wherein:

$R_1$ is aryl optionally substituted by one or more substituents selected from the group consisting of halogen atoms, —OH, —SH, —NO$_2$, —CN, —COOH, ($C_1$-$C_6$)alkoxycarbonyl, ($C_1$-$C_6$)alkylsulfanyl, ($C_1$-$C_6$)alkylsulfinyl, ($C_1$-$C_6$) alkylsulfonyl, ($C_1$-$C_6$)alkyl, ($C_1$-$C_6$)haloalkyl, ($C_1$-$C_6$) alkoxy, and ($C_1$-$C_6$)haloalkoxy;

$R_2$ is aryl optionally substituted by one or more substituents selected from the group consisting of halogen atoms, —OH, —SH, —NO$_2$, —CN, —COOH, ($C_1$-$C_6$)alkoxycarbonyl, ($C_1$-$C_6$)alkylsulfanyl, ($C_1$-$C_6$)alkylsulfinyl, ($C_1$-$C_6$) alkylsulfonyl, ($C_1$-$C_6$)alkyl, ($C_1$-$C_6$)haloalkyl, ($C_1$-$C_6$) alkoxy, and ($C_1$-$C_6$)haloalkoxy;

W is selected from the group consisting of ($C_1$-$C_6$)alkyl, aryl, —NH-heterocyclyl and heteroaryl, each of which optionally substituted by one or more substituents, the same or different, selected from the group consisting of halogen atoms, oxo, —NO$_2$, —CN, ($C_1$-$C_6$)alkyl, ($C_1$-$C_6$)alkoxy, ($C_1$-$C_6$)haloalkyl, ($C_1$-$C_6$)haloalkoxy, ($C_3$-$C_8$)cycloalkyl, heterocyclyl, aryl, aryloxy, haloaryl, ($C_1$-$C_6$)alkyl-NCO—($C_1$-$C_6$)alkyl, —$OR_3$, —$N(R_3)_2$, —$SR_3$, —$OSO_2R_3$, —$COR_3$, —$CO_2R_3$, —$OCOR_3$, —$CON(R_3)_2$, —$NHCOR_3$, —$NHCO_2R_3$, —$NHSO_2R_3$, —NHCO—($C_1$-$C_6$)alkyl-COOH, —$CO_2$—($C_1$-$C_6$)alkyl-$N(R_3)_2$ and —CO-heterocyclyl;

$R_3$ is H or is selected from the group consisting of ($C_1$-$C_6$) alkyl and heteroaryl, optionally substituted by one or more substituents selected from the group consisting of phenyl, halogen atoms, —OH, oxo, —SH, —$NO_2$, —CN, —$CONH_2$ and —COOH;

$A^-$ is a physiologically acceptable anion;

and pharmaceutically acceptable salts thereof.

In the present description, unless otherwise provided, the term "halogen" includes fluorine, chlorine, bromine and iodine atoms.

The term "($C_1$-$C_6$)alkyl", refers to straight or branched chain alkyl groups wherein the number of carbon atoms is from 1 to 6. Examples of said groups are methyl, ethyl, n-propyl, isopropyl, n-butyl, isobutyl, sec-butyl, tert-butyl, pentyl, hexyl and the like.

The term "($C_1$-$C_6$)alkoxy" refers to alkyl-oxy (e.g. alkoxy) groups. Examples of said groups may thus comprise methoxy, ethoxy, n-propoxy, isopropoxy, n-butoxy, isobutoxy, sec-butoxy, tert-butoxy, pentoxy, hexoxy and the like.

Likewise, the expression "($C_1$-$C_6$)alkoxycarbonyl" refers to the above ($C_1$-$C_6$)alkoxy groups further bearing a carbonyl group among which is, for instance, acetoxy (e.g. acetyloxycarbonyl), tert-butoxycarbonyl and the like.

The expressions "($C_1$-$C_6$)haloalkyl" and "($C_1$-$C_6$)haloalkoxy", refer to the above "($C_1$-$C_6$)alkyl" and "($C_1$-$C_6$) alkoxy" groups wherein one or more hydrogen atoms are replaced by one or more halogen atoms, which can be the same or different from each other. Examples of said ($C_1$-$C_6$) haloalkyl and ($C_1$-$C_6$)haloalkoxy groups may thus include halogenated, poly-halogenated and fully halogenated alkyl and alkoxy groups wherein one or more of the hydrogen atoms are replaced by halogen atoms, e.g. trifluoromethyl or trifluoromethoxy groups.

Likewise, the expression "($C_1$-$C_6$)alkylsulfanyl", "($C_1$-$C_6$) alkylsulfinyl" or "($C_1$-$C_6$)alkylsulfonyl" refer, respectively, to alkyl-S—, alkyl-SO— or alkyl-$SO_2$— groups.

The expression "($C_3$-$C_8$)cycloalkyl" refers to cyclic non-aromatic hydrocarbon groups with from 3 to 8 carbon atoms. Examples include cyclopropyl, cyclobutyl, cyclopentyl, cyclohexyl, cycloheptyl, and the like.

The expression "aryl" refers to mono or bi- or tri-cyclic ring systems which have 6 to 20 ring atoms, preferably from 6 to 15 and wherein at least one ring is aromatic.

The expression "heteroaryl" refers to mono, bi- or tri-cyclic ring systems with 5 to 20 ring atoms, preferably from 5 to 15, in which at least one ring is aromatic and in which at least one ring atom is a heteroatom or heteroaromatic group (e.g. N, NH, S or O).

Examples of suitable aryl or heteroaryl monocyclic systems include, for instance, thiophene (thiophenyl), benzene (phenyl), pyrrole (pyrrolyl), pyrazole (pyrazolyl), imidazole (imidazolyl), isoxazole (isoxazolyl), oxazole (oxazolyl), isothiazole (iosthiazolyl), thiazole (thiazolyl), pyridine (pyridinyl), imidazolidine (imidazolidinyl), furan (furanyl) radicals and the like.

Examples of suitable aryl or heteroaryl bicyclic systems include naphthalene (naphthyl), biphenyl (biphenylyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, dihydrobenzo dioxepin, dihydrobenzo oxazin radicals, and the like.

Examples of suitable aryl or heteroaryl tricyclic systems include fluorene (fluorenyl) radicals as well as benzocondensed derivatives of the aforementioned heteroaryl bicyclic systems.

The expression "aryloxy" refers to aryl-oxy groups.

Examples of said groups may thus comprise phenyloxy and the like.

The expression "haloaryl" refers to aryl groups wherein one or more hydrogen atoms are replaced by halogen atoms.

The expression "heterocyclyl" refers to a saturated, partially unsaturated or fully unsaturated 3 to 8 membered heterocyclic ring system in which at least one ring atom is a heteroatom or heteroaromatic group (e.g. N, NH, S or O).

Examples include pyrrolidinyl, piperidinyl, pyridinyl, morpholinyl, furyl, and imidazolyl, and the like.

From the above, it is clear that when referring to a fully unsaturated heterocyclic ring, the above definition also embraces the aforementioned heteroaryl-groups.

Advantageously, the physiologically acceptable anions $A^-$ include those selected from chloride, bromide, iodide, trifluoroacetate, formate, sulfate, phosphate, methanesulfonate, nitrate, maleate, acetate, citrate, fumarate, tartrate, oxalate, succinate, benzoate, and p-toluenesulfonate, preferably chloride, bromide and trifluoroacetate.

Besides the presence of $A^-$ anion, whenever further basic amino groups are present in the compounds of formula (I), additional physiological acceptable anions, among those formerly indicated, may be present. Likewise, in the presence of acidic groups such as COOH groups, corresponding physiological cation salts may be present as well, for instance including alkali or earth-alkali metal ions.

A first preferred group of compounds of general formula (I) is that wherein $R_1$ and $R_2$ are independently aryl groups optionally substituted by one or more halogen atoms or —COOH groups; and W and $A^-$ have the above reported meanings.

Still more preferred, within this class, are the compounds of general formula (I) wherein $R_1$ and $R_2$ are independently phenyl groups optionally substituted by one or more halogen atoms or —COOH groups.

Another preferred group of compounds of general formula (I) is that wherein W is aryl or heteroaryl, each of which being optionally substituted by one or more substituents, the same or different, selected from the group consisting of halogen atoms, —$OR_3$, oxo, —$SR_3$, —$OSO_2R_3$, —$NO_2$, —$COR_3$, —$CO_2R_3$, —$OCOR_3$, —$CON(R_3)_2$, —CN, —$N(R_3)_2$, —$NHCOR_3$, —$NHCO_2R_3$, —$NHSO_2R_3$, ($C_1$-$C_6$)alkyl, ($C_1$-$C_6$)haloalkyl, ($C_1$-$C_6$)alkoxy, ($C_1$-$C_6$)haloalkoxy ($C_3$-$C_8$)cycloalkyl, ($C_3$-$C_8$)heterocyclyl, aryl, —NHCO—($C_1$-$C_6$) alkyl-COOH, —$CO_2$—($C_1$-$C_6$)alkyl-$N(R_3)_2$, ($C_1$-$C_6$)alkyl-NCO—($C_1$-$C_6$)alkyl and —CO-heterocyclyl; and $R_1$, $R_2$ and $A^-$ are as defined above.

Even more preferred, within this class, are the compounds of formula (I) wherein W is selected from the group consisting of phenyl, thiophenyl, dihydrobenzo-dioxepin, dihydrobenzo-dioxin, dihydrobenzo-oxazin, naphthalenyl, or pyrrolidinyl-phenyl, each of which being optionally substituted as above indicated; and $R_1$ and $R_2$ and $A^-$ are as set forth above.

Still more preferred, within this class, are the compounds of formula (I) wherein W is phenyl optionally substituted by one or more groups selected from halogen atoms, —CN, —$NO_2$, —$CF_3$, —$OCH_3$, —$OCF_3$, —OH, —$CONH_2$, methyl, ethyl, ethoxy, phenoxy, ethoxycarbonyl, butoxycarbonyl, —COOH, —$NH_2$, —$N(CH_3)_2$, ($C_1$-$C_6$)alkyl, acetamidopropyl, —SCH$_3$, phenyl, fluorophenyl, morpholinyl, morpholinecarbonyl, isopropoxycarbonyl, dimethylamino ethoxy, methylsulfonyloxy, acetoxy, butyramidyl, pivalamidyl, carboxypropanamidyl, methylsulfonamidyl and pyrrolidinyl; and R$_1$, R$_2$, R$_3$ and A$^-$ are as defined above.

Still more preferred are the compounds of formula (I) wherein W is selected from the group consisting of dihydrobenzo-dioxepin, dihydrobenzo-dioxin, dihydrobenzo-oxazin, naphthalenyl or pyrrolidinyl-phenyl optionally substituted by one or more groups selected from halogen atoms, —COOH and ethyl.

Another preferred group of compounds of formula (I) is that wherein W is —NH-heterocyclyl and R$_1$, R$_2$ and A$^-$ are as defined above.

Still more preferred, within this class, are the compounds of formula (I) wherein W is pyridin-2-ylamino and R$_1$, R$_2$, R$_3$ and A$^-$ are as defined above.

According to specific embodiments of the invention, specific examples of compounds of general formula (I) are reported below:

| Compound | Chemical Name |
| --- | --- |
| C20 | (R)-1-(2-(3-cyanophenyl)-2-oxoethyl)-3-((R)-2-phenyl-2-(phenylamino)acetoxy)-1-azoniabicyclo[2.2.2]octane bromide |
| C21 | (R)-1-(2-(biphenyl-4-yl)-2-oxoethyl)-3-((R)-2-phenyl-2-(phenylamino)acetoxy)-1-azoniabicyclo[2.2.2]octane bromide |
| C22 | (R)-1-(2-(2-nitrophenyl)-2-oxoethyl)-3-((R)-2-phenyl-2-(phenylamino)acetoxy)-1-azoniabicyclo[2.2.2]octane bromide |
| C23 | (R)-1-(2-(3-methoxyphenyl)-2-oxoethyl)-3-((R)-2-phenyl-2-(phenylamino)acetoxy)-1-azoniabicyclo[2.2.2]octane bromide |
| C24 | (R)-1-(2-(2-methoxyphenyl)-2-oxoethyl)-3-((R)-2-phenyl-2-(phenylamino)acetoxy)-1-azoniabicyclo[2.2.2]octane bromide |
| C25 | (R)-1-(2-(2,5-dimethoxyphenyl)-2-oxoethyl)-3-((R)-2-phenyl-2-(phenylamino)acetoxy)-1-azoniabicyclo[2.2.2]octane bromide |
| C26 | (R)-1-(2-(3,4-dimethoxyphenyl)-2-oxoethyl)-3-((R)-2-phenyl-2-(phenylamino)acetoxy)-1-azoniabicyclo[2.2.2]octane bromide |
| C27 | (R)-1-(2-(3-carbamoyl-4-hydroxyphenyl)-2-oxoethyl)-3-((R)-2-phenyl-2-(phenylamino)acetoxy)-1-azoniabicyclo[2.2.2]octane bromide |
| C28 | (R)-1-(2-(2-hydroxyphenyl)-2-oxoethyl)-3-((R)-2-phenyl-2-(phenylamino)acetoxy)-1-azoniabicyclo[2.2.2]octane bromide |
| C29 | (R)-1-(2-(3-chlorophenyl)-2-oxoethyl)-3-((R)-2-phenyl-2-(phenylamino)acetoxy)-1-azoniabicyclo[2.2.2]octane bromide |
| C30 | (R)-1-(2-oxo-2-(4-(trifluoromethoxy)phenyl)ethyl)-3-((R)-2-phenyl-2-(phenylamino)acetoxy)-1-azoniabicyclo[2.2.2]octane bromide |
| C31 | (R)-1-(2-(5-fluoro-2-hydroxyphenyl)-2-oxoethyl)-3-((R)-2-phenyl-2-(phenylamino)acetoxy)-1-azoniabicyclo[2.2.2]octane bromide |
| C32 | (R)-1-(2-(2,3-dihydrobenzo[b][1,4]dioxin-6-yl)-2-oxoethyl)-3-((R)-2-phenyl-2-(phenylamino)acetoxy)-1-azoniabicyclo[2.2.2]octane bromide |
| C33 | (R)-1-(2-(3,4-dihydro-2H-benzo[b][1,4]dioxepin-7-yl)-2-oxoethyl)-3-((R)-2-phenyl-2-(phenylamino)acetoxy)-1-azoniabicyclo[2.2.2]octane bromide |
| C34 | (R)-1-(2-oxo-2-(4-(pyrrolidin-1-yl)phenyl)ethyl)-3-((R)-2-phenyl-2-(phenylamino)acetoxy)-1-azoniabicyclo[2.2.2]octane bromide |
| C35 | (R)-1-(2-(4-carboxyphenyl)-2-oxoethyl)-3-((R)-2-phenyl-2-(phenylamino)acetoxy)-1-azoniabicyclo[2.2.2]octane bromide |
| C36 | (R)-1-(2-(3-nitrophenyl)-2-oxoethyl)-3-((R)-2-phenyl-2-(phenylamino)acetoxy)-1-azoniabicyclo[2.2.2]octane 2,2,2-trifluoroacetate |
| C37 | (R)-1-(2-(4-(3-acetamidopropyl)phenyl)-2-oxoethyl)-3-((R)-2-phenyl-2-(phenylamino)acetoxy)-1-azoniabicyclo[2.2.2]octane 2,2,2-trifluoroacetate |
| C38 | (R)-1-(2-oxo-2-(3-oxo-3,4-dihydro-2H-benzo[b][1,4]oxazin-6-yl)ethyl)-3-((R)-2-phenyl-2-(phenylamino)acetoxy)-1-azoniabicyclo[2.2.2]octane 2,2,2- trifluoroacetate |
| C39 | R)-1-(2-(3-aminophenyl)-2-oxoethyl)-3-((R)-2-phenyl-2-(phenylamino)acetoxy)-1-azoniabicyclo[2.2.2]octane 2,2,2-trifluoroacetate |
| C40 | (R)-1-(2-(2-aminophenyl)-2-oxoethyl)-3-(R)-2-phenyl-2-(phenylamino)acetoxy)-1-azoniabicyclo[2.2.2]octane 2,2,2-trifluoroacetate |
| C44 | (3R)-3-(2-(3-fluorophenyl)-2-(3,4,5-trifluorophenylamino)acetoxy)-1-(2-oxo-2-(thiophen-2-yl)ethyl)-1-azoniabicyclo[2.2.2]octane chloride |
| C46 | (R)-1-(2-(5-ethylthiophen-3-yl)-2-oxoethyl)-3-((R)-2-phenyl-2-(phenylamino)acetoxy)-1-azoniabicyclo[2.2.2]octane 2,2,2-trifluoroacetate |
| C47 | (R)-1-(2-(naphthalen-2-yl)-2-oxoethyl)-3-((R)-2-phenyl-2-(phenylamino)acetoxy)-1-azoniabicyclo[2.2.2]octane bromide |
| C48 | (R)-1-(2-(4-fluoro-2-hydroxyphenyl)-2-oxoethyl)-3-((R)-2-phenyl-2-(phenylamino)acetoxy)-1-azoniabicyclo[2.2.2]octane bromide |
| C49 | (R)-1-(2-(4-(methylthio)phenyl)-2-oxoethyl)-3-((R)-2-phenyl-2-(phenylamino)acetoxy)-1-azoniabicyclo[2.2.2]octane bromide |
| C50 | (R)-1-(2-(3,4-dihydroxyphenyl)-2-oxoethyl)-3-((R)-2-phenyl-2-(phenylamino)acetoxy)-1-azoniabicyclo[2.2.2]octane bromide |
| C51 | (R)-1-(2-(3-chloro-4-fluorophenyl)-2-oxoethyl)-3-((R)-2-phenyl-2-(phenylamino)acetoxy)-1-azoniabicyclo[2.2.2]octane bromide |
| C52 | (R)-1-(2-(4-morpholinophenyl)-2-oxoethyl)-3-((R)-2-phenyl-2-(phenylamino)acetoxy)-1-azoniabicyclo[2.2.2]octane bromide |
| C53 | (R)-1-(2-(3-fluoro-4-hydroxyphenyl)-2-oxoethyl)-3-((R)-2-phenyl-2-(phenylamino)acetoxy)-1-azoniabicyclo[2.2.2]octane bromide |
| C54 | (R)-1-(2-(4-(diethylamino)phenyl)-2-oxoethyl)-3-((R)-2-phenyl-2-(phenylamino)acetoxy)-1-azoniabicyclo[2.2.2]octane bromide |
| C55 | (R)-1-(2-oxo-2-(4-(trifluoromethyl)phenyl)ethyl)-34(R)-2-phenyl-2-(phenylamino)acetoxy)-1-azoniabicyclo[2.2.2]octane bromide |
| C56 | (R)-1-(2-(4-(ethoxycarbonyl)phenyl)-2-oxoethyl)-3-((R)-2-phenyl-2-(phenylamino)acetoxy)-1-azoniabicyclo[2.2.2]octane bromide |
| C57 | (R)-1-(2-(4-(butoxycarbonyl)phenyl)-2-oxoethyl)-3-((R)-2-phenyl-2-(phenylamino)acetoxy)-1-azoniabicyclo[2.2.2]octane bromide |
| C58 | (R)-1-(2-oxo-2-o-tolylethyl)-3-((R)-2-phenyl-2-(phenylamino)acetoxy)-1-azoniabicyclo[2.2.2]octane bromide |
| C59 | ((R)-1-(2-oxo-2-m-tolylethyl)-3-((R)-2-phenyl-2-(phenylamino)acetoxy)-1-azoniabicyclo[2.2.2]octane bromide |
| C60 | (R)-1-(2-(5-ethylthiophen-2-yl)-2-oxoethyl)-3-((R)-2-phenyl-2-(phenylamino)acetoxy)-1-azoniabicyclo[2.2.2]octane chloride |
| C61 | (R)-1-(2-(4-ethoxyphenyl)-2-oxoethyl)-3 -((R)-2-phenyl-2-(phenylamino)acetoxy)-1-azoniabicyclo[2.2.2]octane bromide |
| C62 | (R)-1-(2-(2,5-dichlorothiophen-3-yl)-2-oxoethyl)-3-((R)-2-phenyl-2-(phenylamino)acetoxy)-1-azoniabicyclo[2.2.2]octane chloride |
| C63 | (R)-1-(2-oxo-2-(4-phenoxyphenyl)ethyl)-3-((R)-2-phenyl-2-(phenylamino)acetoxy)-1-azoniabicyclo[2.2.2]octane 2,2,2-trifluoroacetate |
| C64 | (R)-1-(2-(biphenyl-3-yl)-2-oxoethyl)-3-((R)-2-phenyl-2-(phenylamino)acetoxy)-1-azoniabicyclo[2.2.2]octane 2,2,2-trifluoroacetate |
| C65 | (R)-1-(2-(4'-fluorobiphenyl-4-yl)-2-oxoethyl)-3-((R)-2-phenyl-2-(phenylamino)acetoxy)-1-azoniabicyclo[2.2.2]octane 2,2,2-trifluoroacetate |
| C66 | (R)-1-(2-oxo-2-(pyridin-2-ylamino)ethyl)-3-((R)-2-phenyl-2-(phenylamino)acetoxy)-1-azoniabicyclo[2.2.2]octane chloride |
| C67 | (R)-1-(2-(4-carboxyphenyl)-2-oxoethyl)-3-((R)-2-phenyl-2-(phenylamino)acetoxy)-1-azoniabicyclo[2.2.2]octane bromide |
| C68 | (R)-1-(2-(4-(morpholine-4-carbonyl)phenyl)-2-oxoethyl)-3-((R)-2-phenyl-2-(phenylamino)acetoxy)-1-azoniabicyclo[2.2.2]octane bromide |
| C69 | (R)-1-(2-(4-(isopropoxycarbonyl)phenyl)-2-oxoethyl)-3-((R)-2-phenyl-2-(phenylamino)acetoxy)-1-azoniabicyclo[[2.2.2]octane 2,2,2-trifluoroacetate |
| C70 | (R)-1-(2-(4-((2-(dimethylamino)ethoxy)carbonyl)phenyl)-2-oxoethyl)-3-((R)-2-phenyl-2-(phenylamino)acetoxy)-1-azoniabicyclo[2.2.2]octane 2,2,2-trifluoroacetate 2,2,2-trifluoroacetate anion |
| C72 | (R)-1-(2-(4-(methylsulfonyloxy)phenyl)-2-oxoethyl)-3-((R)-2-phenyl-2-(phenylamino)acetoxy)-1-azoniabicyclo[2.2.2]octane bromide |
| C73 | (R)-1-(2-(4-acetoxyphenyl)-2-oxoethyl)-3-((R)-2-phenyl-2-(phenylamino)acetoxy)-1-azoniabicyclo[2.2.2]octane bromide |
| C75 | (R)-1-(2-(4-butyramidophenyl)-2-oxoethyl)-3-((R)-2-phenyl-2-(phenylamino)acetoxy)-1-azoniabicyclo[2.2.2]octane 2,2,2-trifluoroacetate |

-continued

| Compound | Chemical Name |
|---|---|
| C76 | (R)-1-(2-oxo-2-(4-pivalamidophenyl)ethyl)-3-((R)-2-phenyl-2-(phenylamino)acetoxy)-1-azoniabicyclo[2.2.2]octane 2,2,2-trifluoroacetate |
| C77 | (R)-1-(2-(4-(3-carboxypropanamido)phenyl)-2-oxoethyl)-3-((R)-2-phenyl-2-(phenylamino)acetoxy)-1-azoniabicyclo[2.2.2]octane 2,2,2-trifluoroacetate |
| C78 | (R)-1-(2-(4-(methylsulfonamido)phenyl)-2-oxoethyl)-3-((R)-2-phenyl-2-(phenylamino)acetoxy)-1-azoniabicyclo[2.2.2]octane 2,2,2-trifluoroacetate |
| C79 | (R)-1-(2-(4-(ethoxycarbonylamino)phenyl)-2-oxoethyl)-3-((R)-2-phenyl-2-(phenylamino)acetoxy)-1-azoniabicyclo[2.2.2]octane bromide |
| C80 | (3R)-3-(2-(3-carboxyphenylamino)-2-phenylacetoxy)-1-(2-oxo-2-phenylethyl)-1-azoniabicyclo[2.2.2]octane chloride |
| C81 | (R)-3-((S)-2-(4-fluorophenylamino)-2-phenylacetoxy)-1-(2-(4-hydroxyphenyl)-2-oxoethyl)-1-azoniabicyclo[2.2.2]octane 2,2,2-trifluoroacetate |
| C82 | (R)-3-((R)-2-(4-fluorophenylamino)-2-phenylacetoxy)-1-(2-(4-hydroxyphenyl)-2-oxoethyl)-1-azoniabicyclo[2.2.2]octane 2,2,2-trifluoroacetate |
| C83 | (R)-3-((R)-2-(4-fluorophenylamino)-2-phenylacetoxy)-1-(2-(3-hydroxyphenyl)-2-oxoethyl)-1-azoniabicyclo[2.2.2]octane 2,2,2-trifluoroacetate |
| C84 | (R)-3-((R)-2-(4-fluorophenylamino)-2-phenylacetoxy)-1-(2-(2-hydroxyphenyl)-2-oxoethyl)-1-azoniabicyclo[2.2.2]octane 2,2,2-trifluoroacetate |

The compounds of general formula (I) show at least two chiral centers, which are represented by the carbon atoms with asterisks as set forth below:

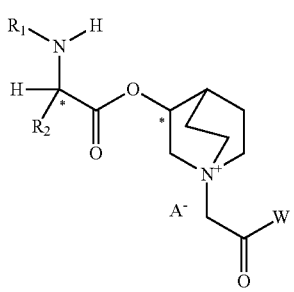

Further, depending on the meanings of $R_1$, $R_2$ and W, it will be clear that additional asymmetric centers may be present in the compounds of formula (I). Therefore, the invention also includes any of the optical stereoisomers, diastereomers and mixtures thereof, in any proportion.

In one of the preferred embodiment, the chiral center on the quinuclidine ring shows a R configuration.

In the present invention, since the absolute configuration of the diastereomers is not defined, they are indicated in the examples as diastereomer 1, 2, or mixtures of them.

The invention also provides pharmaceutical compositions comprising one or more compounds of formula (I), optionally in combination or in admixture with one or more pharmaceutically acceptable carriers and/or excipients.

The invention also provides pharmaceutical compositions suitable for administration by inhalation such as, for instance, inhalable powders, propellant-containing metering aerosols or propellant-free inhalable formulations.

The invention also provides compounds of formula (I) for use as a medicament.

The invention also provides compounds of formula (I) for use in the treatment of broncho-obstructive or inflammatory diseases, preferably asthma or chronic bronchitis or chronic obstructive pulmonary disease (COPD).

In a further aspect, the invention provides the use of the compounds of formula (I) for the manufacture of a medicament for the prevention and/or treatment of broncho-obstructive or inflammatory diseases, preferably asthma or chronic bronchitis or chronic obstructive pulmonary disease (COPD).

The present invention also provides methods for the prevention and/or treatment of broncho-obstructive or inflammatory diseases, preferably asthma or chronic bronchitis or chronic obstructive pulmonary disease (COPD), which comprises administering to a subject in need thereof a therapeutically effective amount of a compound of formula (I).

The invention also refers to a device for the administration of the above pharmaceutical composition, which may be a single- or multi-dose dry powder inhaler, a metered dose inhaler and a soft mist nebulizer comprising the compounds of formula (I).

The invention also refers to a kit comprising the above pharmaceutical compositions in a suitable vial or container and a device which may be a single- or multi-dose dry powder inhaler, a metered dose inhaler and a soft mist nebulizer, adapted to hold the above vial or container.

The compounds of formula (I) may be prepared according to known or conventional methods.

The present invention is also directed to a process for the preparation of the compounds of general formula (I), which process comprises:

(a) the alkylation of a compound of general formula (III) wherein $R_1$ is as defined above

with a compound of general formula (II)

wherein $R_2$ is as defined above, LG is a suitable leaving group and K is a carboxyl group, either as such or in an optionally protected form or an acyl halide group, to give a compound of general formula (IV)

(b) the optional removal of the protecting carboxyl group from the compound of general formula (IV) and its coupling with the compound of formula (V)

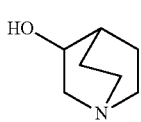
(V)

to give a compound of general formula (VI)

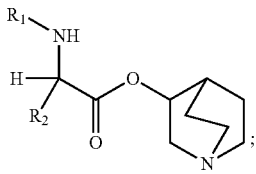
(VI)

(c) the alkylation reaction of the compound of general formula (VI) with an alkylating agent of general formula (VII)

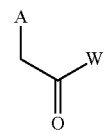
(VII)

in which A is a suitable leaving group and W is as defined above, so as to obtain a compound of general formula (I); and, optionally (d) the conversion of the compound of general formula (I) into another compound of general formula (I) and/or into a pharmaceutically acceptable salt thereof.

The operative conditions that may be used in the process of the invention are described in more details below and are further reported in the following Scheme 1. The starting materials for the preparation of the compounds of formula (I), that is the compounds of formula (II) and (III), as well as any reactant of the process, are known or are easily prepared according to known procedures.

Scheme 1

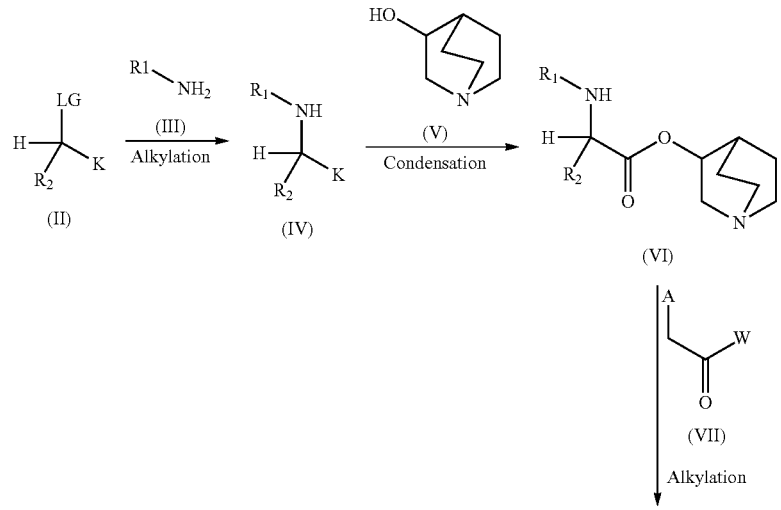

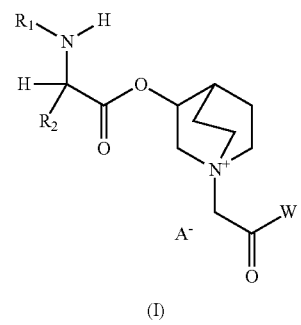

Procedure for the preparation of compounds of formula (I).

According to step (a) of the process, the compounds of formula (IV) may be prepared through the alkylation of an amine of formula (III) with a compound of formula (II), in which LG is a suitable leaving group (e.g. an halide such as bromine) and K is a carboxyl group in an optionally protected form.

Typically, LG is a halide atom and, more preferably, it is a bromine atom. K may be a carboxyl group either as such or in an optionally protected form, typically including carboxyalkyl ester groups (e.g. K=COO($C_1$-$C_6$)alkyl), preferably carboxymethyl (e.g. COOMe).

The alkylation reaction may be promoted by the presence of a base, for instance an amine selected from the group consisting of triethylamine, pyridine and 4-dimethylaminopyridine, either neat or in a suitable solvent (e.g. acetonitrile). This reaction is usually performed in a temperature range from about 0° C. to about 130° C. over a period of about 1 hour to about 74 hours. The reaction may be conducted under conventional heating (using an oil bath) or under microwave heating. The reaction may be carried out in an open vessel or in a sealed tube.

According to step (b) of the process, the compounds of general formula (VI) may then be prepared by coupling the alcohol of formula (V) with a compound of formula (IV), as per step (a). The operative conditions are chosen on the basis of the reactivity of the compound (IV) over alcohol (V) and of the compatibility of other groups being present in both reactants (for a general reference on the above reaction and operative conditions thereof, see, for instance, Carey, F. A. and Sundeberg, R. J. Advanced Organic Chemistry, Third Edition (1990), Plenum Press, New York and London, pg 145, which is incorporated herein by reference in its entirety).

In particular, when K is a protecting carboxyl group, the protecting group has to be first removed before the coupling reaction takes place. When K is a carboxyester moiety (e.g. K=COOMe), removal of the protecting group is carried out under hydrolysis conditions, typically in the presence of any suitable aqueous base selected from the group consisting of sodium, lithium and potassium hydroxide. The reaction is performed in any suitable solvent, for instance in the presence of tetrahydrofuran or dioxane, at room temperature (RT) and over a period of about 1 hour to about 36 hours.

Alternatively, when starting from a compound of formula (IV) wherein K is carboxyl, standard amidation and peptide coupling conditions may be applied to obtain the compounds of formula (VI). Said conditions include, for instance, activating intermediate (IV) by means of one or more equivalents of a commercially available condensing agent such as a carbodiimide (e.g., N,N'-dicyclohexylcarbodiimide (DCC) and the like) in the presence of N-hydroxybenzotriazole (HOBt). An organic base such as triethylamine may be also present in the reaction mixture. The activated intermediate may be either isolated, or pre-formed or generated in situ, and then properly reacted with the alcohol of formula (V). Suitable solvents for the coupling reaction include, but are not limited to, halocarbon solvents (e.g. dichloromethane), tetrahydrofuran, dioxane and acetonitrile. The reaction proceeds at temperature ranging from about 0° C. to about 170° C., for a time period in the range of about 1 hour to about 72 hours. The reaction may be carried out under conventional heating (using an oil bath) or under microwave irradiation. The reaction may be conducted either in an open vessel or in a sealed tube.

Alternatively, a compound of formula (IV) wherein K=COOH may be first activated with other commercially available activating agents such as, for instance, bromotripyrrolidinophosphonium hexafluorophosphate (PyBrOP) or carbonylimidazole, in a suitable aprotic solvent (e.g. dichloromethane, tetrahydrofuran), at about RT, to be then reacted with compound (V).

In addition, compounds of formula (VI) may also be efficiently prepared by the condensation between carboxylic acids (IV) alcohol (V) under typical Mitsunobu conditions (see Kumara Swamy, K. C., Chem. Rev., 2009, 109, 2551-2651, which is incorporated herein by reference in its entirety). For example, acid (IV) and alcohol (V) are reacted in the presence of a suitable phosphine (e.g. triphenylphosphine) and an azadicarboxylate ester (e.g. diethyl azodicarboxylate or diisopropyl azodicarboxylate) in an aprotic solvent such as tetrahydrofuran. The reaction typically proceeds at temperature range from about 0° C. to about 100° C., for a time in the range of about 30 minutes to about 72 hours.

In some embodiments of the present invention, the carboxylic acid (IV) wherein K=COOH may be most conveniently converted into the corresponding acyl halide (IV) wherein K=COCl. This activation may be affected according to one of the several standard procedures reported in the literature. They comprise, for instance, treatment of acid (IV) wherein K=COOH with one or more equivalents of oxalyl chloride in the presence of a catalytic amount of dimethylformamide (DMF) in a halocarbon solvent, such as dichloromethane, at temperature ranging from about 0° C. to about 35° C.

Finally, the acyl chloride (IV) (K=COCl) is directly reacted with the alcohol (V), using known or conventional methods. The reaction may be promoted by a base such as triethylamine, pyridine and 4-dimethylaminopyridine, and carried out in a suitable solvent (e.g. dichloromethane). This reaction is performed in a temperature range from about 0° C. to about 130° C. over a period of about 1 hour to about 74 hours. The reaction may be conducted under conventional heating (using an oil bath) or under microwave heating. The reaction may be carried out in an open vessel or in a sealed tube.

From all of the above, it is clear that alternative conventional synthetic pathways may be applied as well for the preparation of the compounds of formula (VI) from reactants (IV) and (V).

In particular, carboxylic derivatives of formula (IV) may be conveniently converted, in situ, into the corresponding acyl halides to be then reacted with alcohol (V). For example, alcohols (V) are reacted with acids (IV) wherein K=COOH in the presence of triphenylphosphine and a halocarbon solvent such as carbon tetrachloride or dichloromethane, at about RT, in a maximum period of time of 16 hours (see Lee, J. B. J. Am. Chem. Soc., 1966, 88, 3440, which is incorporated herein by reference in its entirety).

Once obtained, compounds of general formula (VI) can be obtained either as single diastereomer or as a mixture of diastereomers. For instance, when alcohol (V) has the R configuration, the corresponding compounds of formula (VI) can be obtained in both S—R configuration or R—R configuration, as well as a mixture of diastereomers (R—R and S—R configuration).

The mixture of diastereomers may be converted to compounds of formula (I) as per step (c) of the process or can be most conveniently resolved to give the two single diastereomers which, in turn, may be converted to compounds of formula (I). This separation can be accomplished by using known procedures. These procedures include, but are not limited to, chromatography purification, preparative HPLC purification and crystallization. For example, the two diastereomers may be separated by flash chromatography on silica gel eluting with suitable solvents or with a mixture of solvents such as DCM (dichloromethane) and methanol and the like. In another process of the present invention, separation of diastereomers may be carried out by using a column filled with a chiral stationary phase, for example Chiralpack AY or Chiralcel OD or Chiralcel OZ, and eluting, for example, with acetonitrile and/or with mixtures of acetonitrile and an alcohol. Alternatively, the separation of diastereomers may be most conveniently achieved by crystallization from an opportune solvent (e.g. ethyl ether), as a free base or after the formation of a suitable salt (e.g. (+)-tartaric acid)).

According to step (c) of the process, the compounds of formula (VI) are then alkylated with an agent of formula (VII) to give compounds of formula (I).

This kind of reaction is largely described in the literature under several different conditions. For instance, the reaction may be performed neat or in a suitable solvent selected from the group consisting of acetonitrile, ethyl acetate, dimethylformamide (DMF), dimethyl sulfoxide (DMSO) and tetrahydrofuran (THF). The reaction typically proceeds at temperature range from about 0° C. to about 170° C., for a time in the range of few minutes to about 72 hours. The reaction may be carried out under conventional heating (using an oil bath) or under microwave irradiation. The reaction may be conducted either in an open vessel or in a sealed tube.

According to step (d) of the process, the compounds of formula (I) can be either considered as final products or can be further reacted to prepare other compounds of general formula (I). Thus, any suitable moiety of $R_1$, $R_2$ or W group in formula (I) could undergo a variety of reactions to afford other final compounds of formula (I).

Likewise, the optional salification of the compounds of formula (I) may be carried out by properly converting any of the free acidic groups (e.g. carboxylic) or free amino groups into the corresponding pharmaceutically acceptable salts.

In this case too, the operative conditions employed for the optional salification of the compounds of the invention are conventional.

As previously reported, the compounds of formula (II) and (III) are known and, if not commercially available, may be readily prepared according to known methods.

In particular, compounds of formula (II) are commercially available or may be conveniently prepared according to standard procedures extensively reported in literature. For instance, compounds of general formula (II) in which LG is a halogen such as a bromine, may be prepared by halogenation of the opportunely substituted phenyl acetic ester (for example following the procedure reported by Epstein, J. W. in *J. Med. Chem.*, 1981, 24/5, 481, which is incorporated herein by reference in its entirety). Alternatively, compounds of general formula (II) may be prepared starting from the appropriately substituted mandelic derivative, using known procedures (a survey of the suitable reactions is given by Larock, L. C., *Comprehensive Organic Transformation*, Second edition (1999), John Wiley & Son Inc, pg 689-700, which is incorporated herein by reference in its entirety).

From all of the above, it should be clear that the above process, comprehensive of any variant thereof for the preparation of suitable compounds of formula (I) of the invention, may be conveniently modified so as to adapt the reaction conditions to the specific needs, for instance by choosing appropriate condensing agents, solvents and protective groups.

More in particular, functional groups present in any of the compounds of formula (II), (III) or (IV) and which could give rise to unwanted side reactions and by-products, need to be properly protected before the condensation reaction takes place.

Likewise, subsequent deprotection of those same protected groups may follow upon completion of the said reactions.

In the present invention, unless otherwise indicated, the term "protecting group", designates a protective group adapted to preserving the function of the group to which it is bound. Specifically, protective groups are used to preserve amino, hydroxyl or carboxyl functions.

Appropriate protective groups may thus include, for example, benzyl, benzyloxycarbonyl, alkyl or benzyl esters, or other substituents commonly used for the protection of such functions, which are all well known [see, for a general reference, T. W. Green; Protective Groups in Organic Synthesis (Wiley, N.Y. 1981) which is incorporated herein by reference in its entirety].

The invention also provides pharmaceutical compositions of compounds of formula (I) in admixture with one or more pharmaceutically acceptable carriers, for example those described in *Remington's Pharmaceutical Sciences Handbook*, XVII Ed., Mack Pub., N.Y., U.S.A., which is incorporated herein by reference in its entirety.

In the present invention, the terms active ingredient or active or compound are to be considered synonyms to be used interchangeably.

Administration of the compounds of the invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering the compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable excipients such as preservatives, wetting agents, sweeteners, flavorants, as well as agents for emulsifying and/or suspending the compounds of the invention. The compounds of the present invention may be injected, for example, intravenously, in the form of an isotonic sterile solution. Other compositions are also possible.

Suppositories for rectal administration of the compounds of the present invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation. Inhalable compositions include inhalable powders, propellant-containing metering aerosols or propellant-free inhalable formulations.

For administration as a dry powder, known single- or multi-dose inhalers may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic or mesh vibrating nebulizers or by soft-mist nebulizers.

The compounds of the invention may be administered as the sole active agent or in combination with other pharmaceutical active ingredients including those currently used in the treatment of respiratory disorders, e.g. beta2-agonists, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs) and mucus regulators.

The invention also provides combinations of a compound of formula (I) with a β2-agonist selected from the group consisting of GSK-642444, indacaterol, milveterol, arformoterol, salbutamol, levalbuterol, terbutaline, AZD-3199, BI-1744-CL, LAS-100977, bambuterol, isoproterenol, procaterol, clenbuterol, reproterol, fenoterol and ASF-1020.

The invention also provides combinations of a compound of formula (I) with a corticosteroid selected from the group consisting of propionate, ciclesonide, mometasone furoate and budesonide.

The invention also provides combinations of a compound of formula (I) with a P38 inhibitor selected from the group consisting of semapimod, talmapimod, pirfenidone, PH-797804, GSK-725, minokine and losmapimod.

The invention also provides combinations of a compound of formula (I) with a IKK2 inhibitor.

The invention also provides combinations of a compound of formula (I) with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled. The invention also provides combinations of a compound of formula (I) with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TP1-PD3, ELB-353, CC-11050, GSK-256066, oglemilast, OX-914, tetomilast, MEM-1414 and RPL-554.

The invention also provides combinations of a compound of formula (I) with a leukotriene modulator selected from the group consisting of montelukast, zafirlukast and pranlukast.

The invention also provides combinations of a compound of formula (I) with a NSAID selected from the group consisting of ibuprofen and ketoprofen.

The invention also provides combinations of a compound of formula (I) with a mucus regulator selected from the group consisting of INS-37217, diquafosol, sibenadet, CS-003, talnetant, DNK-333, MSI-1956 and gefitinib.

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound. Advantageously, the compounds of formula (I) can be administered for example, at a dosage of 0.001 to 1000 mg/day, preferably 0.1 to 500 mg/day.

When the compounds of formula (I) are administered by inhalation route, they are preferably given at a dosage of 0.001 to 500 mg/day, preferably 0.1 to 200 mg/day.

The compounds of formula (I) may be administered for the prevention and/or treatment of any disease wherein M3 antagonists are active. Said disease include: diseases involving inflammation such as asthma and COPD, acute rhinitis; diseases involving the gastrointestinal tract such as peptic ulcer; diseases involving the cardiovascular system such as acute myocardial infarction; diseases involving the genitourinary tract such as renal colic; anticholinesterase and mushroom poisoning; uses in anesthesia; uses in ophthalmology.

They also include neurological and psychiatric disorders such as Parkinsonism and motion sickness.

Preferably, the compounds of formula (I) may be administered for the prevention and/or treatment of respiratory diseases such as from mild to acute severe conditions of asthma and COPD.

Other respiratory diseases include bronchitis, bronchiolitis, bronchiectasis, acute nasopharyngitis, acute and chronic sinusitis, maxillary sinusitis, pharyngitis, tonsillitis, laryngitis, tracheitis, epiglottitis, croup, chronic disease of tonsils and adenoids, hypertrophy of tonsils and adenoids, peritonsillar abscess, rhinitis, abscess or ulcer and nose, pneumonia, viral and bacterial pneumonia, bronchopneumonia, influenza, extrinsic allergic alveolitis, coal workers' pneumoconiosis, asbestosis, pneumoconiosis, pneumonopathy, respiratory conditions due to chemical fumes, vapors and other external agents, emphysema, pleurisy, pneumothorax, abscess of lung and mediastinum, pulmonary congestion and hypostasis, postinflammatory pulmonary fibrosis, other alveolar and parietoalveolar pneumonopathy, idiopathic fibrosing alveolitis, Hamman-Rich syndrome, atelectasis, ARDS, acute respiratory failure, mediastinitis.

Other features of the invention will become apparent in the course of the following descriptions of exemplary embodiments which are given for illustration of the invention and are not intended to be limiting thereof.

EXAMPLES

In the following examples:
I=intermediates
C=compounds.

Example 1

Preparation of (R)-quinuclidin-3-yl 2-phenyl-2-(phenylamino)-acetate (Diastereomers 1 and 2 of I2)

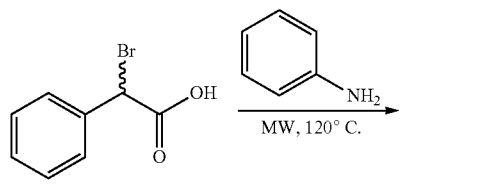

Scheme 2

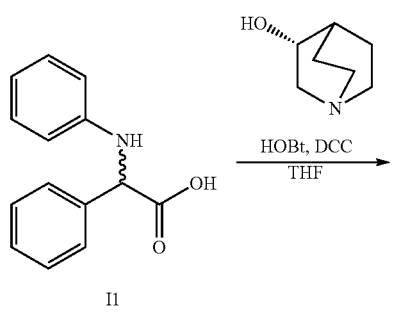

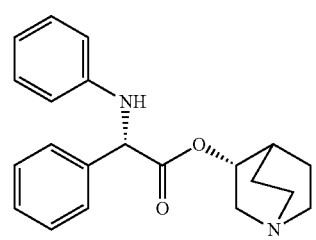

Diastereomer 1 of I2

+

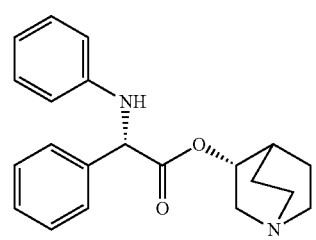

Diastereomer 2 of I2

Preparation of 2-phenyl-2-(phenylamino)acetic acid (I1)

α-Bromophenylacetic acid (5.01 g, 23.2 mmol) was dissolved in aniline (25 ml, 274 mmol), and the mixture reacted in a closed vessel under microwave irradiation at 120° C. for 5 minutes (UPLC-MS monitoring: complete conversion). Dichloromethane (DCM) (100 ml) was added to the reaction mixture, and the resulting solid was filtered; 2M $Na_2CO_3$ (50 ml) was added to the solution, and the aqueous layer was washed with DCM (3×100 ml). The aqueous layer was acidified with 12N HCl (36 ml) and the title compound was recovered as racemic mixture by filtration (5.1 g, 97% yield).

Preparation of (R)-quinuclidin-3-yl 2-phenyl-2-(phenylamino)-acetate (Diastereomers 1 and 2 of I2)

To a solution of 2-phenyl-2-(phenylamino)acetic acid (I1) (3.40 g, 14.9 mmol) in THF (600 ml), was added DCC (4.02 g, 19.4 mmol), HOBt (3.06 g, 19.44 mmol) and 3(R)-quinuclidinol (3.80 g, 29.9 mmol). The resulting mixture was stirred for 16 hours at room temperature (UPLC-MS monitoring: complete conversion). The solvent was evaporated, the residue was taken up with EtOAc and the insoluble was removed by filtration. The clear solution was washed with 1M $K_2CO_3$ and then with brine, was dried over $Na_2SO_4$, filtered and evaporated to dryness. The resulting crude was purified by flash chromatography (DCM/MeOH=95/5, 0.1% $NH_3$ (aq.)) recovering first diastereomer 1 of I2 (1.13 g, 22.5% yield, single diastereomer), and subsequently diastereomer 2 of I2 (0.69 g, 13.7% yield, single diastereomer).

Diastereomer 1 of I2:

$^1$H NMR (300 MHz, DMSO-$d_6$) ppm: 7.48-7.59 (m, 2H), 7.26-7.46 (m, 3H), 7.02-7.14 (m, 2H), 6.67-6.79 (m, 2H), 6.51-6.64 (m, 1H), 6.27 (d, 1H), 5.26 (d, 1H), 4.61-4.78 (m, 1H), 2.96 (ddd, 1H), 2.55-2.67 (m, 3H), 2.16-2.37 (m, 1H), 2.06 (d, 1H), 1.79-1.94 (m, 1H), 1.59-1.76 (m, 1H), 1.35-1.59 (m, 2H), 1.20-1.34 (m, 1H);

LC-MS (ESI POS): 337.04 (MH+);
$[\alpha]_D$=−44.6 (c=0.25 MeOH).

Diastereomer 2 of I2:

$^1$H NMR (300 MHz, DMSO-$d_6$) ppm: 7.48-7.60 (m, 2H), 7.24-7.43 (m, 3H), 6.97-7.14 (m, 2H), 6.66-6.78 (m, 2H), 6.51-6.66 (m, 1H), 6.26 (d, 1H), 5.24 (d, 1H), 4.62-4.81 (m, 1H), 3.08 (ddd, 1H), 2.54-2.70 (m, 5H), 1.64-1.79 (m, 1H), 1.32-1.64 (m, 2H), 1.16-1.32 (m, 1H), 0.93-1.16 (m, 1H);

LC-MS (ESI POS): 337.04 (MH+);
$[\alpha]_D$=+27.6 (c=0.25 MeOH).

Example 2

Preparation of (R)-3-(2-oxo-1-phenyl-2-(quinuclidin-3-yloxy)ethylamino)benzoic acid (I5)

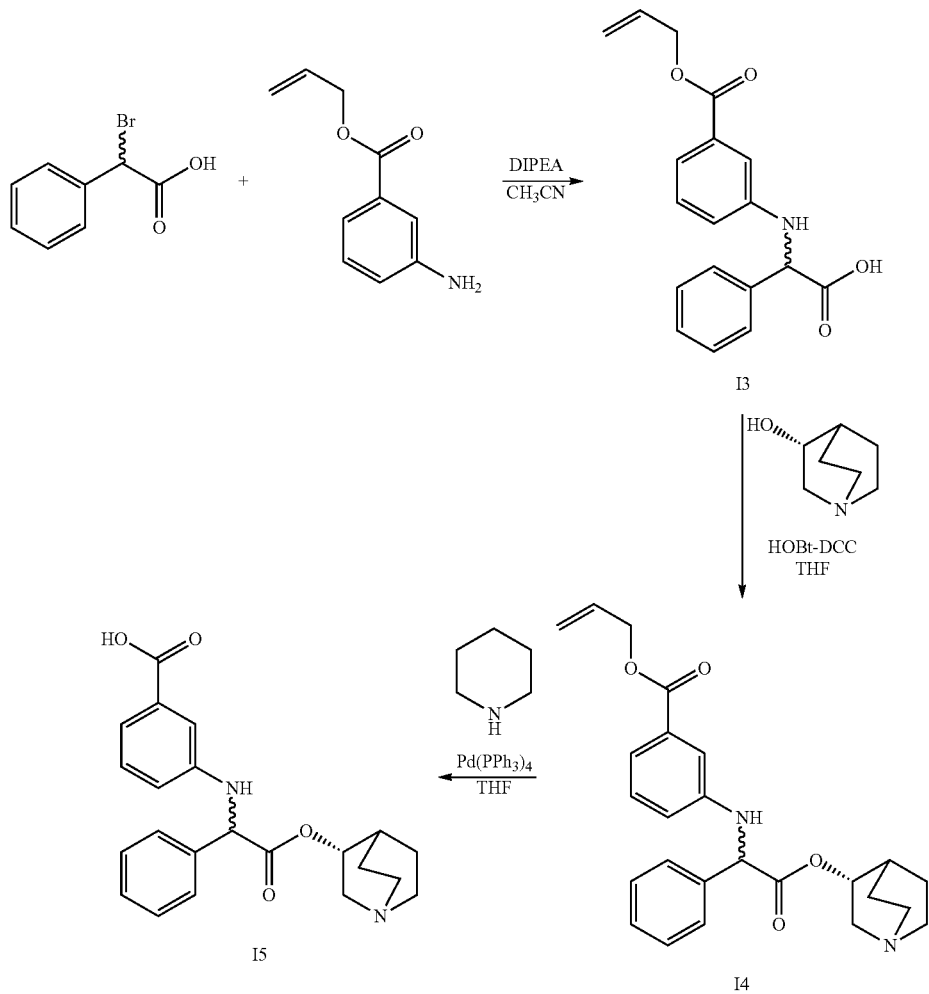

Scheme 3

Preparation of 2-(3-(allyloxycarbonyl)phenylamino)-2-phenylacetic acid (I3)

2-Bromo-2-phenylacetic acid (1.86 g, 8.65 mmol) was added to a solution of allyl 3-aminobenzoate (2.30 g, 13.0 mmol) and DIPEA (2.27 ml, 13.0 mmol) in acetonitrile (48 ml). The reaction was heated at 100° C. for 1 hour under microwave irradiation. The solvent was removed in vacuo and the residue was purified by flash chromatography (DCM/MeOH=95/5) to obtain 2-(3-(allyloxycarbonyl)phenylamino)-2-phenylacetic acid (2.65 g, 98% yield).

Preparation of allyl 3-(2-oxo-1-phenyl-2-((R)-quinuclidin-3-yloxy)ethylamino)benzoate (I4)

To a solution of 2-(3-(allyloxycarbonyl)phenylamino)-2-phenylacetic acid (I3) (2.69 g, 8.64 mmol) in dry THF (80 ml), were added DCC (3.57 g, 17.3 mmol) and HOBt (2.65 g, 17.3 mmol). After 30 minutes, (R)-quinuclidin-3-ol (3.30 g, 25.9 mmol) was added and reaction was stirred at room temperature for 18 hours. The solvent was removed in vacuo and the crude residue was purified by flash-chromatography (DCM/MeOH=97/3+0.3% NH$_4$OH) to obtain allyl 3-(2-oxo-1-phenyl-2-((R)-quinuclidin-3-yloxy)ethylamino)benzoate (2.40 g, 66.1% yield).

Preparation of (R)-3-(2-oxo-1-phenyl-2-(quinuclidin-3-yloxy)ethylamino)benzoic acid (I5)

To a solution of allyl 3-(2-oxo-1-phenyl-2-((R)-quinuclidin-3-yloxy)ethyl-amino)benzoate (I4) (1.40 g, 3.33 mmol) in dry THF (45 ml), were added tetrakis-(triphenylphosphine)palladium(0) (1.15 g, 1.00 mmol) and piperidine (0.99 ml, 1.00 mmol) and the reaction mixture was stirred at 60° C. for 1.5 hours. The solvent was removed in vacuo and the crude was purified by flash chromatography (DCM/MeOH=9/1 to MeOH) to obtain (R)-3-(2-oxo-1-phenyl-2-(quinuclidin-3-yloxy)ethylamino)benzoic acid (500 mg, 39.5% yield).

$^1$H NMR (300 MHz, DMSO-d$_6$) δ ppm 7.49-7.66 (m, 2H), 7.24-7.48 (m, 4H), 7.15 (d, 1H), 7.02 (t, 1H), 6.61-6.86 (m, 1H), 6.25 (d, 1 H), 5.23 and 5.24 (d, 1H), 4.55-4.84 (m, 1H), 2.94 and 3.06 (ddd, 1H), 2.54-2.86 (m, 4H), 1.98-2.40 (m, 1H), 1.65-1.76 and 1.85-1.96 (m, 1H), 1.18-1.63 (m, 4H);
LC-MS (ESI POS): 381.40 (MH+).

Example 3

Preparation of (R)-quinuclidin-3-yl 2-(4-fluorophenylamino)-2-phenylacetate (1S,2S)-1,2-dicarboxyethane-1,2-bis(olate) (Diastereomer 1 and 2 of I8)

Preparation of ethyl 2-(4-fluorophenylamino)-2-phenylacetate (I6)

4-Fluoroaniline (2.38 ml, 24.8 mmol) was added to a solution of ethyl 2-bromo-2-phenylacetate (4.34 ml, 24.8 mmol) in acetonitrile (50 ml). The reaction was heated under microwave irradiation at 100° C. for 30 minutes. Acetonitrile was evaporated, the residue was taken up with EtOAc and washed with 1N NaHCO₃, 1N HCl and brine (100 ml). The organic phase was dried over Na₂SO₄, filtered and evaporated to

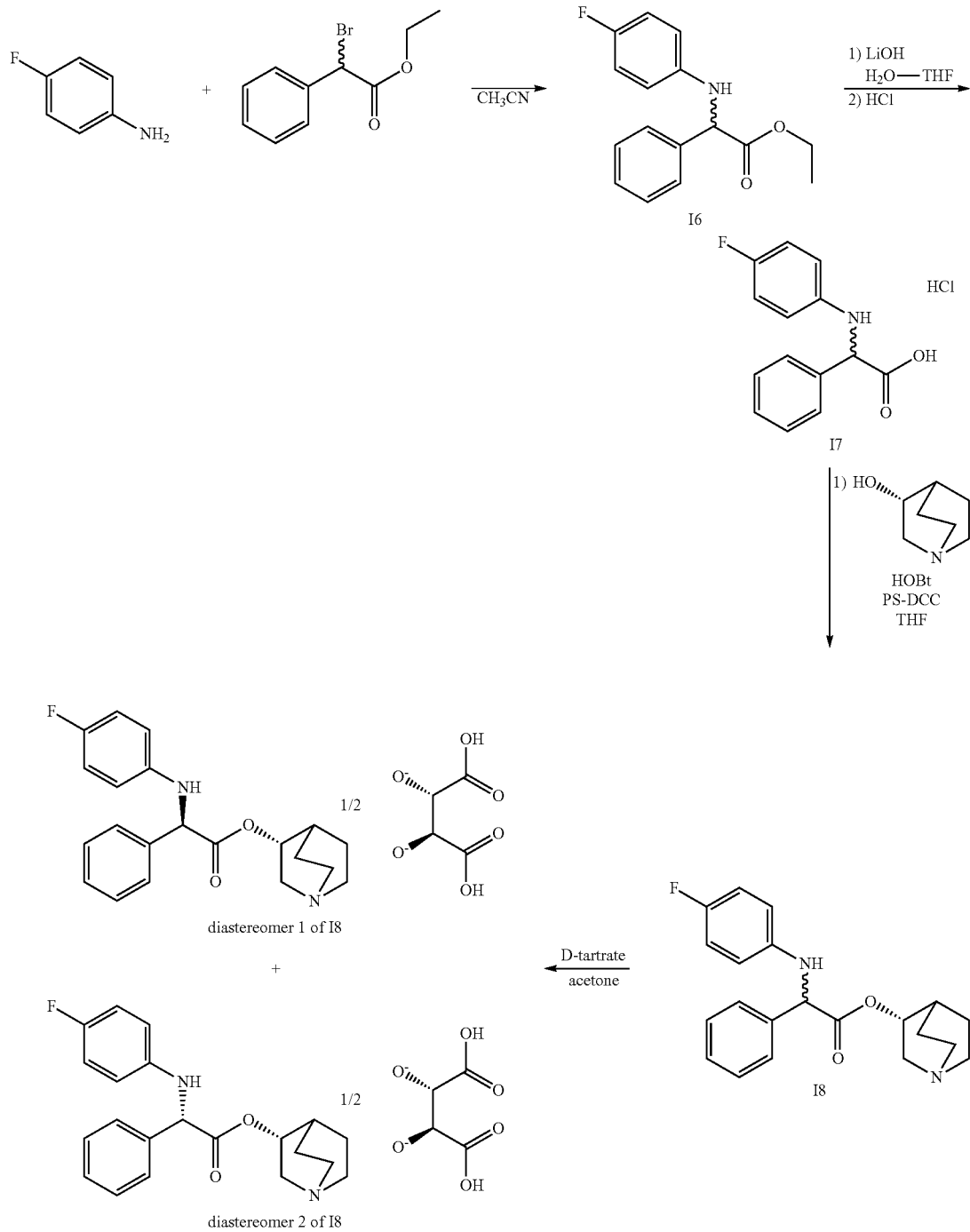

dryness. The crude was purified by flash chromatography (Petroleum ether/EtOAc=99/1 to 8/2) to afford ethyl 2-(4-fluorophenylamino)-2-phenylacetate (4.90 g, 72.3% yield).

Preparation of 2-(4-fluorophenylamino)-2-phenylacetic acid hydrochloride (I7)

Ethyl 2-(4-fluorophenylamino)-2-phenylacetate (I6) (4.10 g, 15.0 mmol) and lithium hydroxide (1.26 g, 52.5 mmol) were dissolved in THF (100 ml) and water (50 ml). The reaction was stirred at room temperature for three days. THF was evaporated, and the resulting basic aqueous solution was acidified till pH 1 with 1N HCl. The solid that precipitated was recovered by suction filtration and dried at 40° C. under vacuum overnight to obtain 2-(4-fluorophenylamino)-2-phenylacetic acid hydrochloride (4.06 g, 96% yield).

Preparation of (R)-quinuclidin-3-yl 2-(4-fluorophenylamino)-2-phenylacetate (I8)

2-(4-Fluorophenylamino)-2-phenylacetic acid hydrochloride (I7) (2.00 g, 8.15 mmol), (R)-quinuclidin-3-ol (1.14 g, 8.97 mmol), HOBt (1.10 g, 8.15 mmol) and DCC (0.841 g, 4.08 mmol) were dissolved in THF (25 ml), and the mixture was stirred at room temperature for three days. Then a second portion of HOBt (0.55 g, 4.08 mmol), DCC (0.84 g, 4.08 mmol) and (R)-quinuclidin-3-ol (0.52 g, 4.08 mmol) were added and the mixture was stirred at room temperature overnight. THF was removed under vacuum, and the residue was treated with H₂O and extracted twice with EtOAc. The organic phase was washed with saturated Na₂CO₃ and dried over Na₂SO₄, filtered and the solvent was evaporated in vacuo. The crude was purified by flash chromatography (EtOAc/MeOH=9/1 to 75/25) to obtain (R)-quinuclidin-3-yl 2-(4-fluorophenylamino)-2-phenylacetate (1.1 g, 38.1% yield, mixture of diasteromers).

Preparation of (R)-quinuclidin-3-yl 2-(4-fluorophenylamino)-2-phenylacetate (1S,2S)-1,2-dicarboxyethane-1,2-bis(olate) (diastereomer 1 and 2 of I8)

(2S,3S)-2,3-Dihydroxysuccinic acid (0.23 g, 1.52 mmol) was added to a suspension of (R)-quinuclidin-3-yl 2-(4-fluorophenylamino)-2-phenylacetate (I8) (1.08 g, 3.05 mmol) in acetone (140 ml). The resulting mixture was heated at reflux and then allowed to cool at room temperature. The precipitate was collected by filtration to obtain (S)—((R)-quinuclidin-3-yl) 2-(4-fluorophenylamino)-2-phenylacetate (1S,2S)-1,2-dicarboxyethane-1,2-bis(olate) (689 mg, 45% yield, diastereomer 2 of I8). Evaporation of the mother solution gave (R)—((R)-quinuclidin-3-yl) 2-(4-fluorophenylamino)-2-phenylacetate (1S,2S)-1,2-dicarboxyethane-1,2-bis(olate) (535 mg, 41% yield, diastereomer 1 of I8).

Diastereomer 1 of I8: ¹H NMR (300 MHz, DMSO-d₆) δ ppm 7.48-7.58 (m, 2H), 7.28-7.43 (m, 3H), 6.85-6.97 (m, 2H), 6.64-6.77 (m, 2H), 6.28 (d, 1H), 5.25 (d, 1H), 4.64-4.81 (m, 1H), 3.01 (ddd, 1H), 2.54-2.72 (m, 3H), 2.21-2.40 (m, 1H), 2.03-2.15 (m, 1H), 1.86-1.97 (m, 1H), 1.38-1.74 (m, 3H), 1.21-1.38 (m, 1H);

Diastereomer 2 of I8: ¹H NMR (300 MHz, DMSO-d₆) δ ppm 7.48-7.63 (m, 2H), 7.24-7.48 (m, 3H), 6.83-7.02 (m, 2H), 6.61-6.81 (m, 2H), 6.30 (d, 1H), 5.26 (d, 1H), 4.80-4.93 (m, 1H), 3.36 (ddd, 1H), 2.69-3.04 (m, 5H), 1.80-1.92 (m, 1H), 1.48-1.76 (m, 2H), 1.21-1.40 (m, 2H).

Example 4

Preparation of (R)—((R)-quinuclidin-3-yl) 2-(4-fluorophenylamino)-2-phenylacetate (Diastereoisomer 1 of I9)

Scheme 5

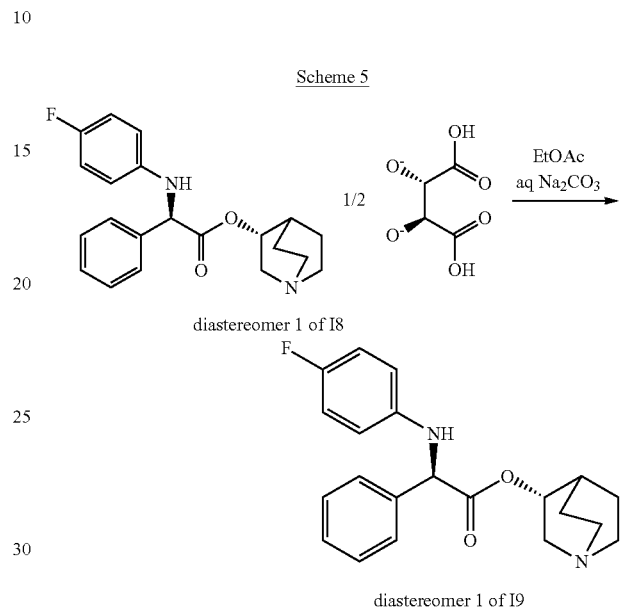

(R)—((R)-quinuclidin-3-yl) 2-(4-fluorophenylamino)-2-phenylacetate (1S,2S)-1,2-dicarboxyethane-1,2-bis(olate) (diastereomer 1 of I8) (535 mg, 1.25 mmol) was dissolved in EtOAc (250 mL) and washed with saturated Na₂CO₃ solution (50 ml). The organic phase was dried over Na₂SO₄, filtered and evaporated to give (R)—((R)-quinuclidin-3-yl) 2-(4-fluorophenylamino)-2-phenylacetate (490 mg; 45% yield, single diastereomer).

¹H NMR (300 MHz, DMSO-d₆) δ ppm 7.48-7.58 (m, 2H), 7.28-7.43 (m, 3H), 6.85-6.97 (m, 2H), 6.64-6.77 (m, 2H), 6.28 (d, 1H), 5.25 (d, 1H), 4.64-4.81 (m, 1H), 3.01 (ddd, 1H), 2.54-2.72 (m, 3H), 2.21-2.40 (m, 1H), 2.03-2.15 (m, 1H), 1.86-1.97 (m, 1H), 1.38-1.74 (m, 3H), 1.21-1.38 (m, 1H);

LC-MS (ESI POS): 355.2 (MH+).

Example 5

Preparation of 2-bromo-1-(3-fluoro-4-hydroxyphenyl)ethanone (I10)

Scheme 6

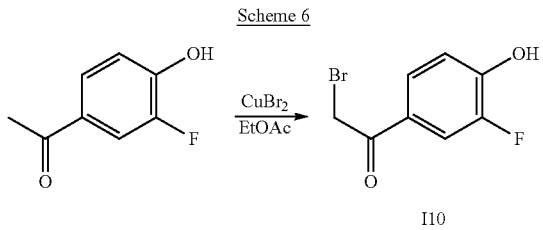

To a solution of 1-(3-fluoro-4-hydroxyphenyl)ethanone (200 mg, 1.30 mmol) in EtOAc (15 ml), was added finely ground copper(II) bromide (522 mg, 2.34 mmol), and the reaction mixture was refluxed for 6 h (UPLC-MS: complete conversion). The reaction mixture was filtered on a celite pad, and the solvent was evaporated to obtain 2-bromo-1-(3-fluoro-4-hydroxyphenyl)ethanone (290 mg, 96% yield). This intermediate was used in the next step without further purification.

LC-MS (ESI POS): 233.1 (M+1+), 235.1 (M+3+).

The compounds listed in Table 1 were prepared by working as previously described for I10, by reaction of $CuBr_2$ with commercially available acetophenone derivatives.

TABLE 1

| Compound | Structure | Yield | Analytical |
|---|---|---|---|
| I11 | (structure: 2-bromo-1-(3,4-dihydroxyphenyl)ethanone) | 97% | LC-MS (ESI POS): 231.0 (M + 1+), 233.0 (M + 3+). |
| I12 | (structure: ethyl 4-(2-bromoacetyl)benzoate) | 100% | LC-MS (ESI POS): Not detectable |
| I13 | (structure: butyl 4-(2-bromoacetyl)benzoate) | 100% | LC-MS (ESI POS): Not detectable |
| I14 | (structure: 2-bromo-1-(4-phenoxyphenyl)ethanone) | 100% | LC-MS (ESI POS): 291.2 (M + 1+), 293.2 (M + 3+). |

Example 6

Preparation of 2-bromo-1-o-tolylethanone (I15)

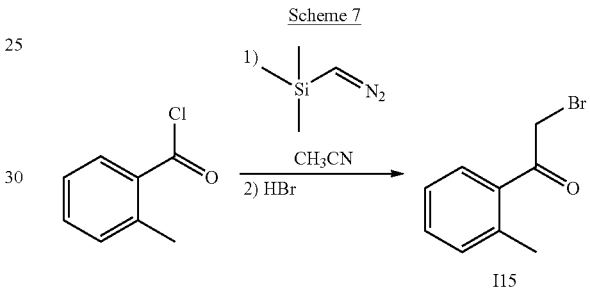

Scheme 7

To a solution of 2-methylbenzoyl chloride (169 μl, 1.29 mmol) in dry acetonitrile (5 ml) and cooled at 0° C., under nitrogen atmosphere, was added (diazomethyl)-trimethylsilane (1.94 ml, 3.88 mmol, 2M in hexane). The reaction was stirred at room temperature for 15 hours, then it was cooled at 0° C. and 48% HBr (512 μl, 4.53 mmol) was slowly added. The reaction was stirred at room temperature for 3 hours. EtOAc and water were added, the organic layer was separated and the aqueous phase was neutralized with 1M NaOH and extracted with EtOAc. The combined organic layers were dried over $Na_2SO_4$, filtered and evaporated to dryness to obtain 2-bromo-1-o-tolylethanone (250 mg, 91% yield). This intermediate was used in the next step without any further purification.

$^1$H NMR (300 MHz, DMSO-$d_6$) δ ppm 7.82-7.91 (m, 1H), 7.45-7.52 (m, 1H), 7.25-7.40 (m, 2H), 4.86 (s, 2H), 2.41 (s, 3H).

The compounds listed in Table 2 were prepared by working as previously described for I15, by reaction of (diazomethyl)trimethylsilane and hydrobromic acid with commercially available acyl chloride derivatives.

TABLE 2

| Compound | Structure | Yield | Analytical |
|---|---|---|---|
| I16 | (structure: 2-bromo-1-m-tolylethanone) | 91% | $^1$H NMR (300 MHz, DMSO-$d_6$) δ ppm 7.74-7.88 (m, 2 H), 7.48-7.54 (m, 1 H), 7.44 (t, 1 H), 4.91 (s, 2 H), 2.39 (s, 3 H) |

TABLE 2-continued

| Compound | Structure | Yield | Analytical |
|---|---|---|---|
| I17 | 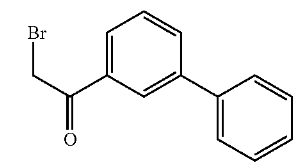 [SMILES: O=C(CBr)c1cccc(-c2ccccc2)c1] | 92% | $^1$H NMR (300 MHz, DMSO-$d_6$) δ ppm 8.26 (t, 1 H), 7.91-8.05 (m, 2 H), 7.73-7.80 (m, 2 H), 7.66 (t, 1 H), 7.47-7.57 (m, 2 H), 7.37-7.47 (m, 1 H), 5.05 (s, 2 H) |
| I18 | 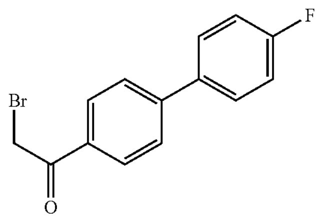 [SMILES: O=C(CBr)c1ccc(-c2ccc(F)cc2)cc1] | 100% | $^1$H NMR (300 MHz, DMSO-$d_6$) δ ppm 8.04-8.19 (m, 2 H), 7.76-7.93 (m, 4 H), 7.25-7.43 (m, 2 H), 4.95 (s, 2 H) |

Example 7

Preparation of 2-chloro-1-phenylethanone (I19)

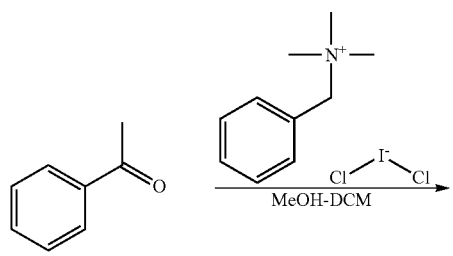

To a solution of acetophenone (5.00 g, 41.6 mmol) in DCM (42 ml), was added benzyltrimethylammonium tetrachloroiodate (28.8 g, 83.0 mmol). The reaction was heated at 60° C. for 1 hour, then the solvent was evaporated under vacuum. The residue was portioned between DCM (300 ml) and water (300 ml). The organic phase was washed sequentially with aqueous Na$_2$S$_2$O$_5$ and brine, dried over Na$_2$SO$_4$, filtered and evaporated to dryness. The residue was triturated with petroleum ether to obtain 2-chloro-1-phenylethanone (4.90 g, 76.2% yield)

LC-MS (ESI POS): 155.0 (M+1+), 156.9 (M+3+)..

Example 8

Preparation of (R)-1-(2-(3-cyanophenyl)-2-oxoethyl)-3-((R)-2-phenyl-2-(phenylamino)acetoxy)-1-azoniabicyclo[2.2.2]octane bromide (Diastereomer 1 of C20)

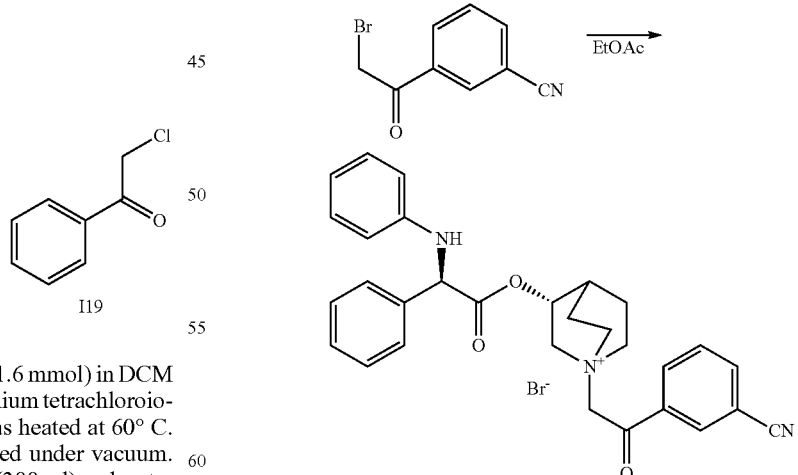

3-(2-Bromoacetyl)benzonitrile (40.0 mg, 0.18 mmol) was added to a solution of (R)—((R)-quinuclidin-3-yl) 2-phenyl-2-(phenylamino)acetate (diastereomer 1 of I2) (60 mg, 0.18 mmol) in EtOAc (2 ml). The reaction mixture was stirred at room temperature overnight (UPLC-MS: complete conversion). EtOAc was removed under vacuum, and the residue is triturated with Et$_2$O. The solid was collected by suction filtration and dried at 40° C. for 48 hours to obtain the (R)-1-(2-(3-cyanophenyl)-2-oxoethyl)-3-((R)-2-phenyl-2-(phenylamino)acetoxy)-1-azoniabicyclo[2.2.2]octane bromide (61.1 mg, 61% yield).

$^1$H NMR (300 MHz, DMSO-d$_6$) δ ppm 8.45 (s, 1H), 8.15-8.30 (m, 2H), 7.83 (t, 1H), 7.51-7.66 (m, 2H), 7.29-7.51 (m, 3H), 7.00-7.19 (m, 2H), 6.69-6.82 (m, 2H), 6.53-6.66 (m, 1H), 6.36 (d, 1H), 5.39 (d, 1H), 5.16-5.30 (m, 1H), 5.11 (s, 2H), 3.94-4.17 (m, 1H), 3.55-3.76 (m, 3H), 3.41-3.53 (m, 1H), 3.32-3.41 (m, 1H), 2.36 (m, 1H), 1.83-2.16 (m, 4H);

LC-MS (ESI POS): 480.2 (MH+).

The compounds listed in Table 3 were prepared by working as previously described for C20, by reaction of diastereomer 1 of I2 with commercially available alkylating agents.

TABLE 3

| Compound | Structure | Yield | Analytical |
|---|---|---|---|
| Diastereomer 1 of C21 | 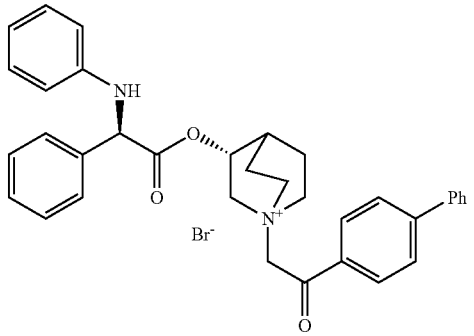<br>Single diastereomer | 69% | LC-MS (ESI POS): 531.2 (M$^+$)<br>$^1$H NMR (300 MHz, DMSO-d$_6$) δ ppm 8.00-8.13 (m, 2 H), 7.88-8.00 (m, 2 H), 7.71-7.85 (m, 2 H), 7.28-7.65 (m, 8 H), 7.03-7.17 (m, 2 H), 6.70-6.88 (m, 2 H), 6.55-6.66 (m, 1 H), 6.37 (d, 1 H), 5.40 (d, 1 H), 5.19-5.28 (m, 1 H), 5.14 (s, 2 H), 4.00-4.18 (m, 1 H), 3.58-3.78 (m, 3 H), 3.48-3.58 (m, 1 H), 3.33-3.49 (m, 1 H), 2.33-2.43 (m, 1 H), 1.77-2.18 (m, 4 H) |
| Diastereomer 1 of C22 | 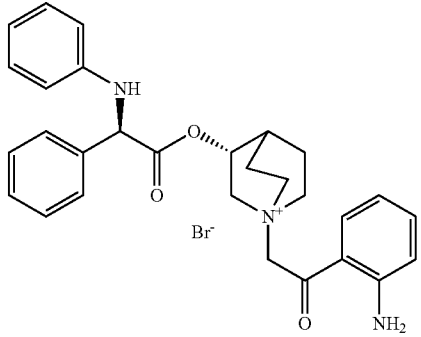<br>Single diastereomer | 50% | LC-MS (ESI POS): 500.1 (M$^+$)<br>$^1$H NMR (300 MHz, DMSO-d$_6$) δ ppm 8.29 (dd, 1 H), 8.00 (td, 1 H), 7.89 (td, 1 H), 7.82 (dd, 1 H), 7.52-7.63 (m, 2 H), 7.27-7.51 (m, 3 H), 7.02-7.17 (m, 2 H), 6.71-6.84 (m, 2 H), 6.53-6.65 (m, 1 H), 6.37 (d, 1 H), 5.40 (d, 1 H), 5.19-5.30 (m, 1 H), 4.96 (s, 2 H), 3.96-4.25 (m, 1 H), 3.55-3.78 (m, 3 H), 3.44-3.55 (m, 1 H), 3.34-3.44 (m, 1 H), 2.32-2.42 (m, 1 H), 1.66-2.19 (m, 4 H) |
| Diastereomer 1 of C23 | 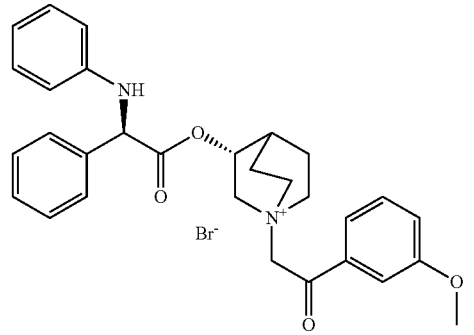<br>Single diastereomer | 67% | LC-MS (ESI POS): 485.2 (M$^+$)<br>$^1$H NMR (300 MHz, DMSO-d$_6$) δ ppm 7.28-7.65 (m, 9 H), 6.98-7.17 (m, 2 H), 6.68-6.81 (m, 2 H), 6.54-6.68 (m, 1 H), 6.37 (d, 1 H), 5.39 (d, 1 H), 5.16-5.28 (m, 1 H), 5.09 (s, 2 H), 3.99-4.16 (m, 1 H), 3.85 (s, 3 H), 3.54-3.75 (m, 3 H), 3.46-3.54 (m, 1 H), 3.33-3.46 (m, 1 H), 2.32-2.42 (m, 1 H), 1.74-2.17 (m, 4 H) |

TABLE 3-continued

| Compound | Structure | Yield | Analytical |
|---|---|---|---|
| Diastereomer 1 of C24 | 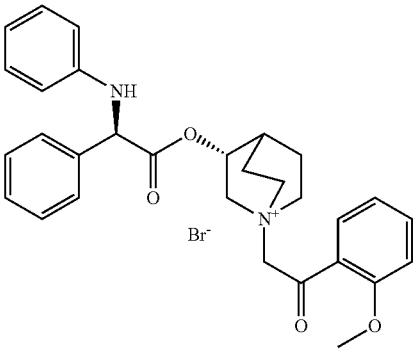 Single diastereomer | 69% | LC-MS (ESI POS): 482.2 (M+)<br>$^1$H NMR (300 MHz, DMSO-d$_6$) δ ppm 7.80 (dd, 1 H), 7.70 (ddd, 1 H), 7.54-7.64 (m, 2 H), 7.32-7.49 (m, 3 H), 7.27 (d, 1 H), 7.02-7.20 (m, 3 H), 6.68-6.80 (m, 2 H), 6.53-6.67 (m, 1 H), 6.37 (d, 1 H), 5.38 (d, 1 H), 5.14-5.28 (m, 1 H), 4.83 (s, 2 H), 4.09 (ddd, 1 H), 3.96 (s, 3 H), 3.55-3.70 (m, 3 H), 3.43-3.55 (m, 1 H), 3.31-3.43 (m, 1 H), 2.30-2.41 (m, 1 H), 1.76-2.20 (m, 4 H) |
| Diastereomer 1 of C25 | 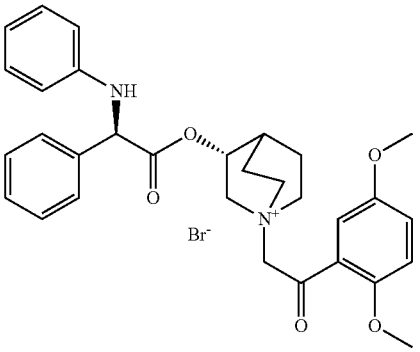 Single diastereomer | 89% | LC-MS (ESI POS): 515.2 (M+)<br>$^1$H NMR (300 MHz, DMSO-d$_6$) δ ppm 7.59 (d, 2 H) 7.18-7.49 (m, 6 H) 7.10 (t, 2 H) 6.75 (d, 2 H) 6.60 (t, 1 H) 6.37 (d, 1 H) 5.38 (d, 1 H) 5.12-5.26 (m, 1 H) 4.82 (s, 2 H) 3.98-4.18 (m, 1 H) 3.91 (s, 3 H) 3.78 (s, 3 H) 3.55-3.70 (m, 3 H) 3.49 (d, 1 H) 3.35 (m, 1 H) 2.31-2.42 (m, 1 H) 1.77-2.15 (m, 4 H) |
| Diastereomer 1 of C26 | 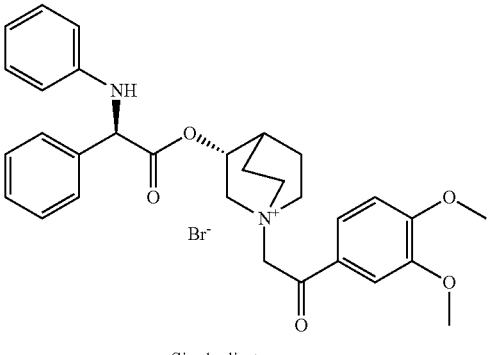 Single diastereomer | 87% | LC-MS (ESI POS): 515.2 (M+)<br>$^1$H NMR (300 MHz, DMSO-d$_6$) δ ppm 7.53-7.74 (m, 3 H) 7.31-7.51 (m, 4 H) 7.01-7.23 (m, 3 H) 6.74 (d, 2 H) 6.60 (t, 1 H) 6.37 (d, 1 H) 5.38 (d, 1 H) 5.14-5.28 (m, 1 H) 5.04 (s, 2 H) 4.00-4.17 (m, 1 H) 3.85 (s, 3 H) 3.89 (s, 3 H) 3.47-3.76 (m, 4 H) 3.34-3.47 (m, 1 H) 2.31-2.43 (m, 1 H) 1.81-2.16 (m, 4 H) |
| Diastereomer 1 of C27 | 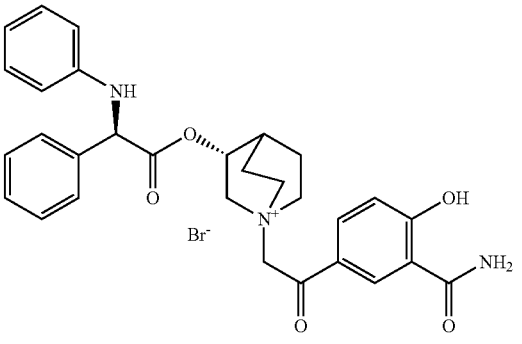 Single diastereomer | 54% | LC-MS (ESI POS): 514.1 (M+)<br>$^1$H NMR (300 MHz, DMSO-d$_6$) δ ppm 13.86 (br. s., 1 H) 8.58-8.83 (m, 1 H) 8.52 (m, 1 H) 8.08-8.30 (m, 1 H) 8.01 (dd, 1 H) 7.52-7.65 (m, 2 H) 7.26-7.48 (m, 3 H) 7.01-7.18 (m, 3 H) 6.74 (d, 2 H) 6.60 (t, 1 H) 6.36 (d, 1 H) 5.38 (d, 1 H) 5.15-5.28 (m, 1 H) 5.04 (d, 2 H) 4.09 (m, 1 H) 3.48-3.77 (m, 4 H) 3.33-3.48 (m, 1 H) 2.32-2.42 (m, 1 H) 1.80-2.17 (m, 4 H) |

TABLE 3-continued

| Compound | Structure | Yield | Analytical |
|---|---|---|---|
| Diastereomer 1 of C28 | Single diastereomer | 87% | LC-MS (ESI POS): 471.25 (M+)<br>$^1$H NMR (300 MHz, DMSO-$d_6$) δ ppm 11.13 (br. s., 1 H) 7.77 (dd, 1 H) 7.51-7.63 (m, 3 H) 7.31-7.50 (m, 3 H) 6.92-7.22 (m, 4 H) 6.69-6.81 (m, 2 H) 6.60 (t, 1 H) 6.37 (d, 1 H) 5.33-5.43 (m, 1 H) 5.12-5.27 (m, 1 H) 4.81-4.99 (m, 2 H) 3.99-4.19 (m, 1 H) 3.33-3.73 (m, 5 H) 2.30-2.41 (m, 1 H) 1.79-2.12 (m, 4 H) |
| Diastereomer 1 of C29 | Single diastereomer | 81% | LC-MS (ESI POS): 489.22 (M+)<br>$^1$H NMR (300 MHz, DMSO-$d_6$) δ ppm 8.01 (t, 1 H) 7.92 (dt, 1 H) 7.83 (s, 1 H) 7.53-7.72 (m, 3 H) 7.29-7.49 (m, 3 H) 7.09 (dd, 2 H) 6.68-6.83 (m, 2 H) 6.60 (t, 1 H) 6.37 (d, 1 H) 5.35-5.45 (m, 1 H) 5.16-5.27 (m, 1 H) 5.14 (s, 2 H) 3.96-4.18 (m, 1 H) 3.33-3.73 (m, 5 H) 2.32-2.43 (m, 1 H) 1.78-2.18 (m, 4 H) |
| Diastereomer 1 of C30 | Single diastereomer | 79% | LC-MS (ESI POS): 539.15 (M+)<br>$^1$H NMR (300 MHz, DMSO-$d_6$) δ ppm 8.11 (d, 2 H) 7.60 (s, 4 H) 7.27-7.50 (m, 3 H) 7.02-7.21 (m, 2 H) 6.75 (dd, 2 H) 6.60 (t, 1 H) 6.37 (d, 1 H) 5.32-5.45 (m, 1 H) 5.15 (s, 2 H) 5.00-5.30 (m, 1 H) 3.98-4.19 (m, 1 H) 3.57-3.79 (m, 3 H) 3.34-3.57 (m, 2 H) 2.31-2.44 (m, 1 H) 1.81-2.18 (m, 4 H) |
| Diastereomer 1 of C31 | Single diastereomer | 84% | LC-MS (ESI POS): 489.24 (M+)<br>$^1$H NMR (300 MHz, DMSO-$d_6$) δ ppm 11.16 (s, 1 H) 7.28-7.67 (m, 7 H) 6.98-7.18 (m, 3 H) 6.75 (d, 2 H) 6.61 (t, 1 H) 6.37 (d, 1 H) 5.31-5.43 (m, 1 H) 5.12-5.26 (m, 1 H) 4.81-4.96 (m, 2 H) 4.01-4.16 (m, 1 H) 3.34-3.73 (m, 5 H) 2.30-2.43 (m, 1 H) 1.76-2.14 (m, 4 H) |

TABLE 3-continued

| Compound | Structure | Yield | Analytical |
|---|---|---|---|
| Diastereomer 1 of C32 | Single diastereomer | 87% | LC-MS (ESI POS): 513.25 (M$^+$)<br>$^1$H NMR (300 MHz, DMSO-d$_6$) δ ppm 7.31-7.65 (m, 7 H) 7.04-7.12 (m, 3 H) 6.72-6.77 (m, 2 H) 6.60 (t, 1 H) 6.36 (d, 1 H) 5.36-5.40 (m, 1 H) 5.17-5.23 (m, 1 H) 4.95-5.08 (m, 2 H) 4.24-4.42 (m, 4 H) 3.97-4.14 (m, 1 H) 3.32-3.70 (m, 5 H) 2.29-2.43 (m, 1 H) 1.78-2.15 (m, 4 H) |
| Diastereomer 1 of C33 | Single diastereomer | 77% | LC-MS (ESI POS): 527.3 (M$^+$)<br>$^1$H NMR (300 MHz, DMSO-d$_6$) δ ppm 7.31-7.65 (m, 7 H) 7.04-7.12 (m, 3 H) 6.72-6.77 (m, 2 H) 6.60 (t, 1 H) 6.36 (d, 1 H) 5.36-5.40 (m, 1 H) 5.17-5.23 (m, 1 H) 4.95-5.08 (m, 2 H) 4.24-4.42 (m, 4 H) 3.97-4.14 (m, 1 H) 3.32-3.70 (m, 5 H) 2.29-2.43 (m, 1 H) 1.78-2.15 (m, 4 H) |
| Diastereomer 1 of C34 | Single diastereomer | 88% | LC-MS (ESI POS): 524.19 (M$^+$)<br>$^1$H NMR (300 MHz, DMSO-d$_6$) δ ppm 7.79 (d, 2 H) 7.52-7.64 (m, 2 H) 7.28-7.48 (m, 3 H) 7.09 (dd, 2 H) 6.68-6.83 (m, 2 H) 6.52-6.68 (m, 3 H) 6.36 (d, 1 H) 5.37 (d, 1 H) 5.13-5.25 (m, 1 H) 4.89 (dd, 2 H) 4.01-4.18 (m, 1 H) 3.46-3.80 (m, 4 H) 3.32-3.45 (m, 5 H) 2.30-2.40 (m, 1 H) 1.75-2.12 (m, 8 H) |

Example 9

Preparation of (R)-1-(2-(4-carboxyphenyl)-2-oxoethyl)-3-((R)-2-phenyl-2-(phenylamino)acetoxy)-1-azoniabicyclo[2.2.2]octane 2,2,2-trifluoroacetate (Diastereomer 1 of C35)

Scheme 10

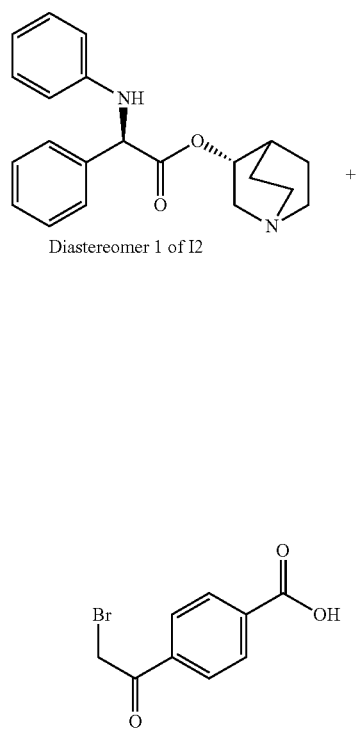

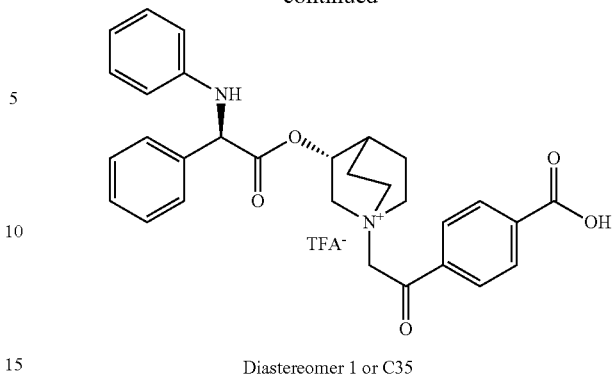

Diastereomer 1 or C35

4-(2-Bromoacetyl)benzoic acid (50.6 mg, 0.21 mmol) was added to a solution of (R)—((R)-quinuclidin-3-yl) 2-phenyl-2-(phenylamino)acetate (diastereomer 1 of I2) (70 mg, 0.21 mmol) in EtOAc (2 ml), and the reaction was stirred at room temperature overnight (UPLC-MS: complete conversion). Solvent was evaporated under reduced pressure, and the crude was purified by preparative HPLC to obtain the (R)-1-(2-(4-carboxyphenyl)-2-oxoethyl)-3-((R)-2-phenyl-2-(phenylamino)acetoxy)-1-azoniabicyclo[2.2.2]octane 2,2,2-trifluoroacetate (53.3 mg, 42% yield).

$^1$H NMR (300 MHz, DMSO-$d_6$) δ ppm 8.10-8.17 (m, 2H), 8.02-8.10 (m, 2H), 7.54-7.67 (m, 2H), 7.29-7.48 (m, 3H), 7.01-7.17 (m, 2H), 6.71-6.80 (m, 2H), 6.54-6.66 (m, 1H), 6.36 (br. s., 1H), 5.39 (s, 1H), 5.18-5.30 (m, 1H), 5.13 (s, 2H), 3.95-4.22 (m, 1H), 3.52-3.81 (m, 5H), 2.33-2.43 (m, 1H), 1.76-2.21 (m, 4H);

LC-MS (ESI POS): 499.2 (M$^+$).

The compounds listed in Table 4 were prepared by working as previously described for C35, by reaction of diastereomer 1 of I2 with commercially available alkylating agents and through purification by preparative HPLC.

TABLE 4

| Compound | Structure | Yield | Analytical |
|---|---|---|---|
| Diastereomer 1 of C36<br>Single diastereomer | (structure shown) | 27% | LC-MS (ESI POS): 500.3 (M$^+$)<br>$^1$H NMR (300 MHz, DMSO-$d_6$) δ ppm 8.68 (t, 1 H), 8.57 (ddd, 1 H), 8.35 (ddd, 1 H), 7.92 (t, 1 H), 7.53-7.65 (m, 2 H), 7.28-7.53 (m, 3 H), 7.02-7.21 (m, 2 H), 6.69-6.81 (m, 2 H), 6.55-6.69 (m, 1 H), 6.36 (br. s., 1 H), 5.39 (s, 1 H), 5.20-5.29 (m, 1 H), 5.18 (s, 2 H), 4.00-4.16 (m, 1 H), 3.28-3.77 (m, 5 H), 2.33-2.43 (m, 1 H), 1.68-2.18 (m, 4 H) |

TABLE 4-continued

| Compound | Structure | Yield | Analytical |
|---|---|---|---|
| Diastereomer 1 of C37 | Single diastereomer | 38% | LC-MS (ESI POS): 554.3 (M+)<br>$^1$H NMR (300 MHz, DMSO-d$_6$) δ ppm 7.88 (d, 2 H) 7.81-7.85 (m, 1 H) 7.51-7.63 (m, 2 H) 7.29-7.49 (m, 5 H) 7.09 (dd, 2 H) 6.74 (d, 2 H) 6.60 (t, 1 H) 5.38 (s, 1 H) 5.16-5.27 (m, 1 H) 5.06 (s, 2 H) 4.07 (m, 1 H) 3.28-3.76 (m, 5 H) 2.96-3.09 (m, 2 H) 2.61-2.77 (m, 2 H) 2.31-2.41 (m, 1 H) 1.86-2.17 (m, 4 H) 1.80 (s, 3 H) 1.72 (quin, 2 H) |
| Diastereomer 1 of C38 | Single diastereomer | 33% | LC-MS (ESI POS): 526.24 (M+)<br>$^1$H NMR (300 MHz, DMSO-d$_6$) δ ppm 10.97 (s, 1 H) 7.52-7.68 (m, 3 H) 7.28-7.52 (m, 4 H) 7.11 (dt, 3 H) 6.74 (d, 2 H) 6.60 (t, 1 H) 6.20-6.53 (m, 1 H) 5.38 (s, 1 H) 5.12-5.28 (m, 1 H) 5.00 (s, 2 H) 4.74 (s, 2 H) 3.94-4.16 (m, 1 H) 3.21-3.53 (m, 5 H) 2.30-2.43 (m, 1 H) 1.76-2.13 (m, 4 H) |

Example 10

Preparation of (R)-1-(2-(3-aminophenyl)-2-oxoethyl)-3-((R)-2-phenyl-2-(phenylamino)acetoxy)-1-azoniabicyclo[2.2.2]octane 2,2,2-trifluoroacetate (diastereomer 1 of C39)

Scheme 11

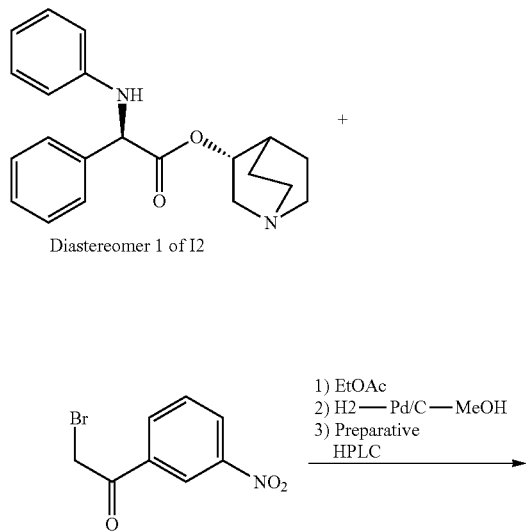

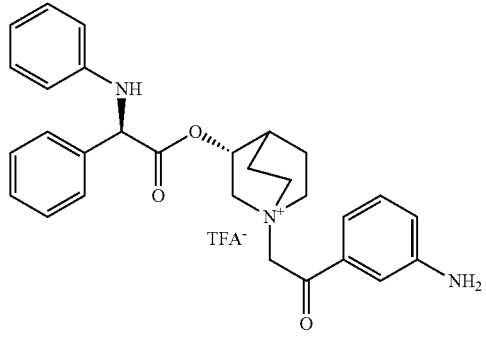

Diastereomer 1 or C39

2-Bromo-1-(3-nitrophenyl)ethanone (43.5 mg, 0.18 mmol) was added to a solution of (R)—((R)-quinuclidin-3-yl) 2-phenyl-2-(phenylamino)acetate (diastereomer 1 of I2) (60 mg, 0.18 mmol) in EtOAc (2 ml). The reaction mixture was stirred at room temperature overnight (UPLC-MS: complete conversion). The reaction mixture was poured into a Parr's vial and diluted with MeOH. Pd/C (cat amount; about 10 mg) was added and reaction is hydrogenated at 30 pound per square inch (psi) for 30 minutes (UPLC-MS: complete conversion). The catalyst was removed by filtration, and the clear solution was concentrated under vacuum. The crude was purified by preparative HPLC to obtain (R)-1-(2-(3-aminophenyl)-2-oxoethyl)-3-((R)-2-phenyl-2-(phenylamino)acetoxy)-1-azoniabicyclo[2.2.2]octane 2,2,2-trifluoroacetate (52.1 mg, 50.1% yield).

¹H NMR (300 MHz, DMSO-d₆) δ ppm 7.53-7.62 (m, 2H) 7.30-7.49 (m, 3H) 7.18-7.30 (m, 1H) 7.03-7.18 (m, 4H) 6.93 (dd, 1H) 6.68-6.80 (m, 2H) 6.60 (t, 1H) 5.38 (s, 1H) 5.15-5.27 (m, 1H) 5.00 (s, 2H) 4.06 (dd, 1H) 3.55-3.75 (m, 3H) 3.27-3.55 (m, 2H) 2.30-2.42 (m, 1H) 1.80-2.15 (m, 4H);

LC-MS (ESI POS): 470.2 (M⁺).

The compound C40 in Table 5 was prepared by working as previously described for C39, by alkylation of diastereomer 1 of I2 with 2-bromo-1-(2-nitrophenyl)ethanone, reduction and purification by preparative HPLC.

TABLE 5

| Compound | Structure | Yield | Analytical |
|---|---|---|---|
| Diastereomer 1 of C40 | 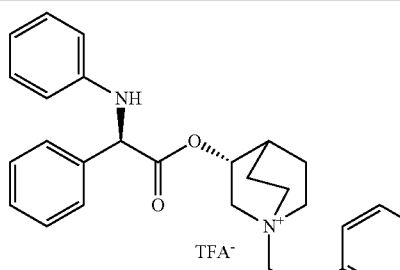 Single diastereomer | 55.7% | LC-MS (ESI POS): 470.2 (M⁺)<br>¹H NMR (300 MHz, DMSO-d₆) δ ppm 7.53-7.65 (m, 3 H) 7.27-7.48 (m, 4 H) 7.05-7.16 (m, 2 H) 6.83 (dd, 1 H) 6.74 (dd, 2 H) 6.51-6.65 (m, 2 H) 5.38 (s, 1 H) 5.16-5.26 (m, 1 H) 4.81-5.00 (m, 2 H) 4.00 (dd, 1 H) 3.37-3.72 (m, 5 H) 2.31-2.42 (m, 1 H) 1.79-2.16 (m, 4 H) |

Example 11

Preparation of (3R)-3-(2-(3-fluorophenyl)-2-(3,4,5-trifluorophenylamino)acetoxy)-1-(2-oxo-2-(thiophen-2-yl)ethyl)-1-azoniabicyclo[2.2.2]octane chloride (diastereomer 1 of C44)

Scheme 12

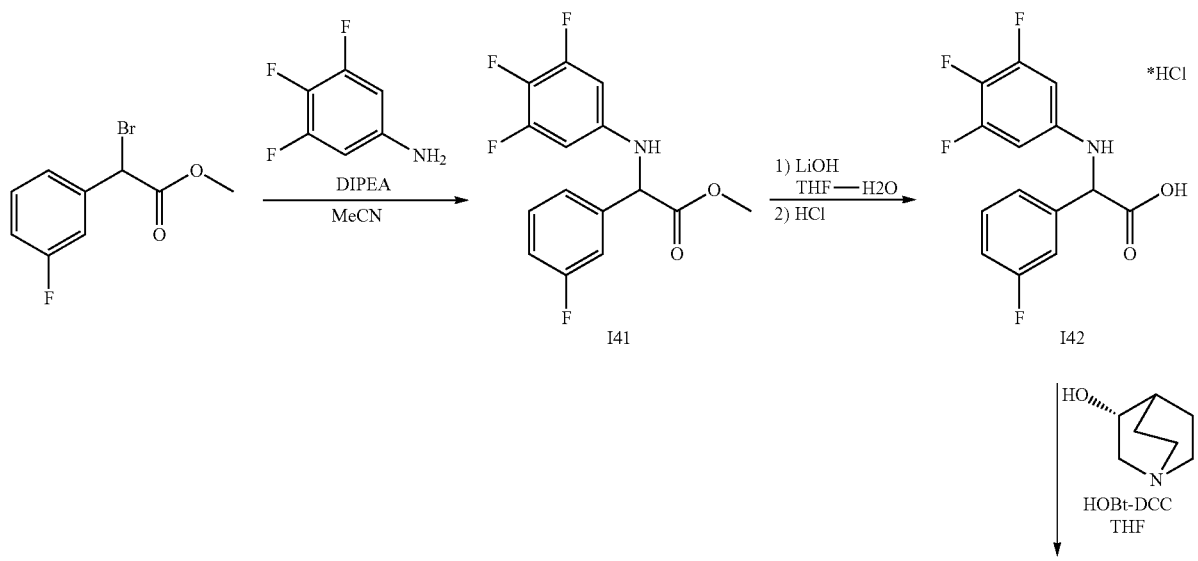

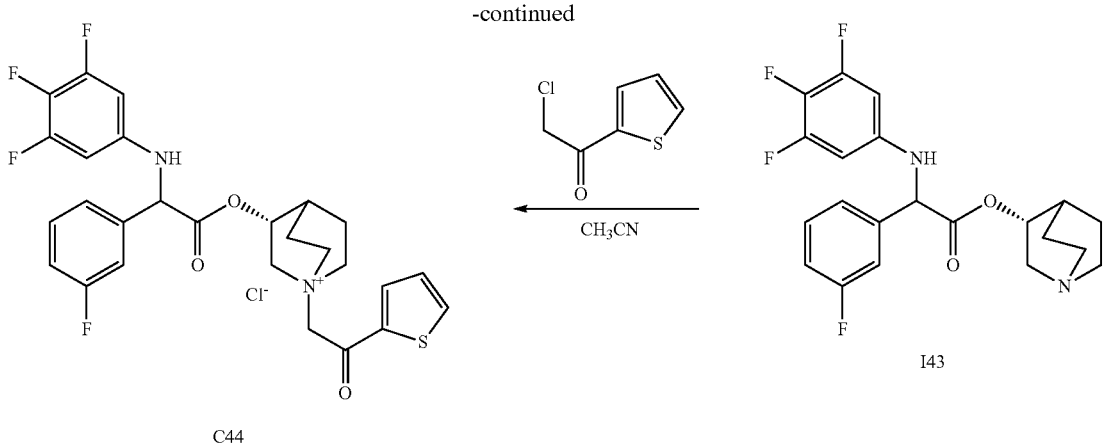

Preparation of (3-fluoro-phenyl)-(3,4,5-trifluoro-phenylamino)-acetic acid methyl ester (I41)

Methyl 2-bromo-2-(3-fluorophenyl)acetate (300 mg, 1.21 mmol) and 3,4,5-trifluoroaniline (268 mg, 1.82 mmol) were dissolved in acetonitrile (4 ml) and stirred under microwave heating into a sealed vial at 120° C. for 1 hours. Some crystals of KI were added, and the resulting mixture was stirred under the same conditions for 1 hour (UPLC-MS: conversion complete). Solvent was evaporated, and the crude residue was purified by flash chromatography (Petroleum ether/EtOAc=9/1) to obtain (3-fluoro-phenyl)-(3,4,5-trifluoro-phenylamino)-acetic acid methyl ester (202 mg, 53% yield).

LC-MS (ESI POS): 314.1 (MH+).

Preparation of 2-(3-fluorophenyl)-2-(3,4,5-trifluorophenylamino)acetic acid hydrochloride (I42)

Methyl 2-(3-fluorophenyl)-2-(3,4,5-trifluorophenylamino)acetate (I41) (202 mg, 0.64 mmol) was dissolved in THF/water (6 ml/3 ml). Lithium hydroxide hydrate (54.1 mg, 1.29 mmol) was added, and the solution was stirred at room temperature overnight (UPLC-MS: complete conversion). THF was evaporated, and the residue was taken up with water and pH was adjusted to pH 1 with HCl. The product was extracted twice with DCM, and the organic layers was dried ($Na_2SO_4$) and evaporated to afford the title compound 2-(3-fluorophenyl)-2-(3,4,5-trifluorophenylamino)acetic acid hydrochloride (217 mg, 100% yield).

$^1$H NMR (300 MHz, DMSO-$d_6$) δ ppm 13.19 (br. s., 1H), 7.37-7.49 (m, 1H), 7.25-7.37 (m, 3H), 7.05-7.20 (m, 1H), 6.86 (d, 1H), 6.32-6.62 (m, 1H), 5.25 (d, 1H).

Preparation of (R)-quinuclidin-3-yl 2-(3-fluorophenyl)-2-(3,4,5-trifluorophenylamino)-acetate (I43)

Polymer-Supported DiCyclohexylCarbodiimide (PS-DCC) (972 mg, 1.29 mmol, loading: 1.33 mmol/g) was suspended in dry tetrahydrofuran (10 ml). 2-(3-fluorophenyl)-2-(3,4,5-trifluorophenylamino)acetic acid hydrochloride (I42) (217 mg, 0.65 mmol), HOBT (198 mg, 1.29 mmol), and (R)-quinuclidin-3-ol (247 mg, 1.94 mmol) were added, and the mixture was shaken at r.t. for 16 hours. PS-DCC was filtered off, the filtrate was evaporated and the residue was dissolved in EtOAc and washed with $NaHCO_3$, water and brine. The organic layer was dried over $Na_2SO_4$, filtered and evaporated. The resulting crude compound was purified by filtration through a pad of silica-gel eluting with DCM/MeOH=93/7. The resulting white foam was dissolved in DCM and passed through an Isolute PE-AX cartridge (5 g, 0.6 mmol/g, DCM/MeOH=9/1) to obtain (R)-quinuclidin-3-yl 2-(3-fluorophenyl)-2-(3,4,5-trifluorophenylamino)acetate (264 mg, 32% yield).

$^1$H NMR (300 MHz, DMSO-$d_6$) δ ppm 7.26-7.57 (m, 3H), 7.07-7.24 (m, 1H), 6.95 (d, 1H), 6.36-6.78 (m, 2H), 5.45 and 5.47 (d, 1H), 4.61-4.88 (m, 1H), 2.99 and 3.09 (ddd, 1H), 2.54-2.71 (m, 4H), 1.98-2.36 (m, 1H), 1.66-1.74 and 1.87-1.95 (m, 1H), 1.10-1.66 (m, 4H).

Preparation of (3R)-3-(2-(3-fluorophenyl)-2-(3,4,5-trifluorophenylamino)acetoxy)-1-(2-oxo-2-(thiophen-2-yl)ethyl)-1-azoniabicyclo[2.2.2]octane chloride (C44).

(R)-Quinuclidin-3-yl 2-(3-fluorophenyl)-2-(3,4,5-trifluorophenylamino)acetate (I43) (85 mg, 0.21 mmol) and 2-chloro-1-(thiophen-2-yl)ethanone (35.1 mg, 0.22 mmol) were dissolved in acetonitrile (5 ml) and stirred at room temperature for 48 hours. The solvent was evaporated, and the resulting crude compound was purified by flash chromatography (DCM/MeOH=9/1) to obtain (3R)-3-(2-(3-fluorophenyl)-2-(3,4,5-trifluorophenylamino)acetoxy)-1-(2-oxo-2-(thiophen-2-yl)ethyl)-1-azoniabicyclo[2.2.2]octane chloride (70 mg; 59% yield).

$^1$H NMR (300 MHz, DMSO-$d_6$) δ ppm 8.18-8.25 (m, 1H), 8.04-8.15 (m, 1H), 7.30-7.54 (m, 4H), 7.00-7.30 (m, 2H), 6.52-6.79 (m, 2H), 5.58 (d, 1H), 5.16-5.28 (m, 1H), 5.04-5.16 (m, 2H), 3.97-4.22 (m, 1H), 3.47-3.95 (m, 5H), 2.13-2.23 (m, 1H), 1.48-2.08 (m, 4H);

LC-MS (ESI POS): 533.4 (MH+).

Example 12

Preparation of (R)-1-(2-(5-ethylthiophen-3-yl)-2-oxoethyl)-3-((R)-2-phenyl-2-(phenylamino)acetoxy)-1-azoniabicyclo[2.2.2]octane 2,2,2-trifluoroacetate (C46)

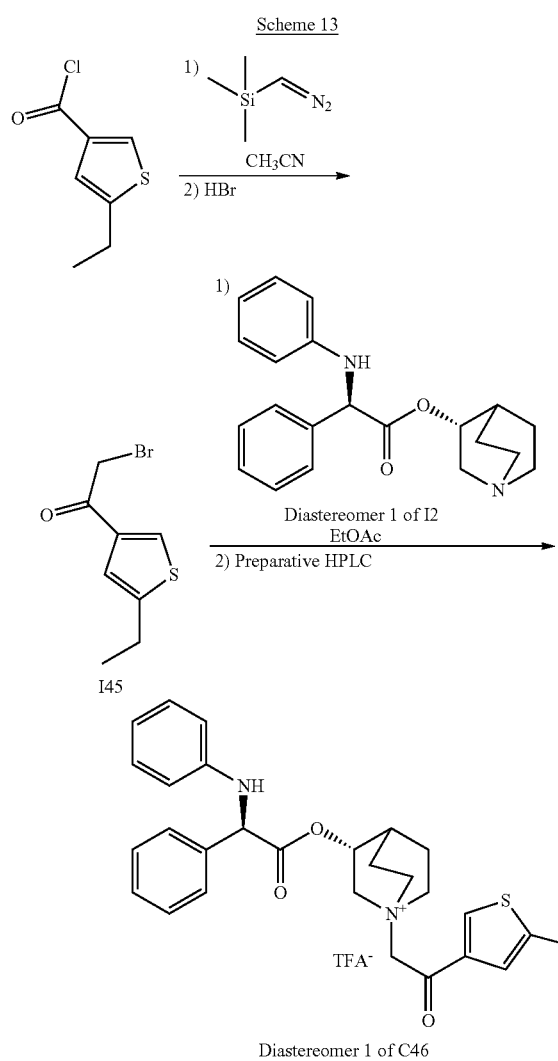

Scheme 13

Diastereomer 1 of I2

Diastereomer 1 of C46

Preparation of 2-bromo-1-(5-ethylthiophen-3-yl)ethanone (I45)

5-Ethylthiophene-3-carbonyl chloride (224 mg, 1.28 mmol) was dissolved in dry CH3CN (10 ml) and cooled at 0° C., under nitrogen atmosphere. (Diazomethyl)-trimethylsilane (1.92 ml, 3.85 mmol, 2M in hexane) was slowly added, and the resulting reaction was stirred at room temperature for 18 hours. Then the reaction was cooled at 0° C. and 48% HBr was added dropwise. The reaction was stirred at 0° C. for 2 hours. Smashed ice was added to the mixture, and then sodium bicarbonate was added until pH is about 7. The solution was extracted with EtOAc, and the organic layer was separated, dried over sodium sulfate, filtered and evaporated under reduced pressure. The crude was purified by flash chromatography (Petroleum ether/EtOAc=9/1) to obtain 2-bromo-1-(5-ethylthiophen-3-yl)ethanone (97 mg, 32.4% yield).

Preparation of (R)-1-(2-(5-ethylthiophen-3-yl)-2-oxoethyl)-3-((R)-2-phenyl-2-(phenylamino)acetoxy)-1-azoniabicyclo[2.2.2]octane 2,2,2-trifluoroacetate (C46)

2-Bromo-1-(5-ethylthiophen-3-yl)ethanone (I45) (97 mg, 0.42 mmol) was added to a solution of (R)—((R)-quinuclidin-3-yl) 2-phenyl-2-(phenylamino)acetate (diastereomer 1 of I2) (140 mg, 0.42 mmol) in EtOAc (4 ml). The reaction was stirred at room temperature overnight. Then solvent was evaporated under vacuum, and the crude was purified by preparative HPLC to obtain (R)-1-(2-(5-ethylthiophen-3-yl)-2-oxoethyl)-3-(R)-2-phenyl-2-(phenylamino)acetoxy)-1-azoniabicyclo[2.2.2]octane 2,2,2-trifluoroacetate (112 mg, 44.7% yield).

$^1$H NMR (300 MHz, DMSO-$d_6$) δ ppm 8.39 (d, 1H) 7.51-7.62 (m, 2H) 7.31-7.51 (m, 3H) 7.27 (d, 1H) 7.02-7.16 (m, 2H) 6.69-6.82 (m, 2H) 6.60 (t, 1H) 6.13-6.50 (m, 1H) 5.37 (s, 1H) 5.10-5.28 (m, 1H) 4.90(s, 2H) 3.96-4.17 (m, 1H) 3.28-3.68 (m, 5H) 2.79-2.95 (m, 2H) 2.35 (t, 1H) 1.77-2.14 (m, 4H) 1.26 (t, 3H);

LC-MS (ESI POS): 489.24 (M+).

Example 13

Preparation of (R)-1-(2-(naphthalen-2-yl)-2-oxoethyl)-3-((R)-2-phenyl-2-(phenylamino)acetoxy)-1-azoniabicyclo[2.2.2]octane bromide (Diastereomer 1 of C47)

Scheme 14

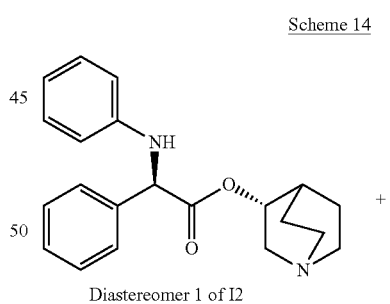

Diastereomer 1 of I2

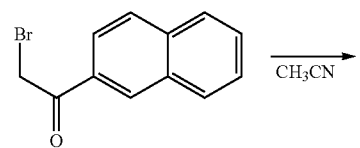

47

-continued

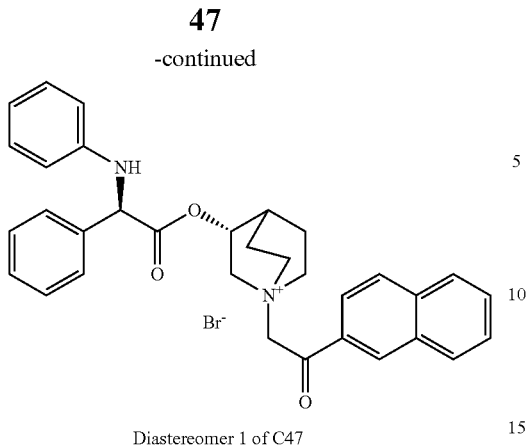

Diastereomer 1 of C47

To a solution of (R)—((R)-quinuclidin-3-yl) 2-phenyl-2-(phenylamino)acetate (diastereomer 1 of I2) (75 mg, 0.22 mmol) in acetonitrile (5 ml), was added 2-bromo-1-(naphthalen-2-yl)ethanone (55.5 mg, 0.22 mmol) and the reaction was stirred at 100° C. for 70 minutes under microwave irradiation (UPLC-MS: complete conversion). The solvent was evaporated and the crude was triturated with i-Pr$_2$O-EtOAc (9/1) to obtain (R)-1-(2-(naphthalen-2-yl)-2-oxoethyl)-3-((R)-2-phenyl-2-(phenylamino)acetoxy)-1-azoniabicyclo[2.2.2]octane bromide (121.9 mg, 93% yield).

$^1$H NMR (300 MHz, DMSO-d$_6$) δ ppm 8.68 (s, 1H), 8.15 (d, 1H), 8.11 (d, 1H), 8.06 (d, 1H), 7.97 (dd, 1H), 7.64-7.82 (m, 2H), 7.53-7.64 (m, 2H), 7.31-7.51 (m, 3H), 6.98-7.19 (m, 2H), 6.69-6.82 (m, 2H), 6.52-6.66 (m, 1H), 6.37 (d, 1H), 5.40 (d, 1H), 5.24 (s, 2H), 5.18-5.29 (m, 1H), 4.04-4.24 (m, 1H), 3.61-3.84 (m, 3H), 3.50-3.61 (m, 1H), 3.36-3.50 (m, 1H), 2.32-2.44 (m, 1H), 1.80-2.19 (m, 4H);

LC-MS (ESI POS): 505.27 (M+).

Example 14

Preparation of (R)-1-(2-(4-fluoro-2-hydroxyphenyl)-2-oxoethyl)-3-((R)-2-phenyl-2-(phenylamino)acetoxy)-1-azoniabicyclo[2.2.2]octane bromide (Diastereomer 1 of C48)

Scheme 15

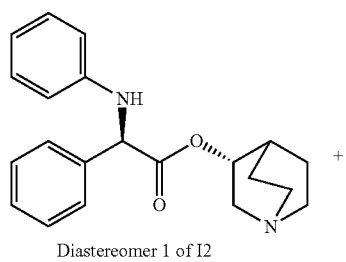

Diastereomer 1 of I2

48

-continued

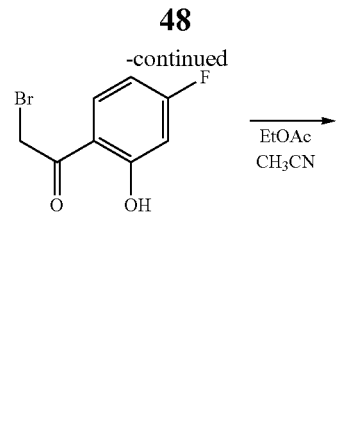

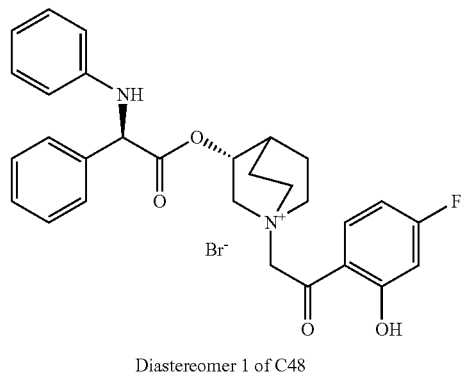

Diastereomer 1 of C48

To a solution of (R)—((R)-quinuclidin-3-yl) 2-phenyl-2-(phenylamino)acetate (diastereomer 1 of I2) (100 mg, 0.30 mmol) in EtOAc (3 ml) and acetonitrile (2 ml), was added 2-bromo-1-(4-fluoro-2-hydroxyphenyl)ethanone (69.3 mg, 0.30 mmol), and the reaction was stirred at room temperature for 15 hours (UPLC-MS: complete conversion). The solvent was evaporated and the crude was triturated in i-Pr$_2$O-EtOAc (1/1) to obtain (R)-1-(2-(4-fluoro-2-hydroxyphenyl)-2-oxoethyl)-3-((R)-2-phenyl-2-(phenylamino)acetoxy)-1-azoniabicyclo[2.2.2]octane bromide (154.0 mg, 91% yield).

$^1$H NMR (300 MHz, DMSO-d$_6$) δ ppm 11.71 (br. s., 1H), 7.86 (dd, 1H), 7.51-7.70 (m, 2H), 7.26-7.51 (m, 3H), 6.99-7.18 (m, 2H), 6.84 (td, 1H), 6.81 (dd, 1H), 6.69-6.78 (m, 2H), 6.48-6.68 (m, 1H), 6.36 (d, 1H), 5.37 (d, 1H), 5.09-5.28 (m, 1H), 4.86 (s, 2H), 3.94-4.20 (m, 1H), 3.55-3.78 (m, 3H), 3.43-3.55 (m, 1H), 3.33-3.43 (m, 1H), 2.30-2.43 (m, 1H), 1.80-2.09 (m, 4H);

LC-MS (ESI POS): 489.31 (M+).

The compounds listed in Table 6 were prepared by working as previously described for C48, by alkylation of diastereomer 1 of I2 with 2-bromo-1-(4-(methylthio)phenyl)ethanone and I11.

TABLE 6

| Compound | Structure | Yield | Analytical |
|---|---|---|---|
| Diastereomer 1 of C49 | Single diastereomer | 89% | LC-MS (ESI POS): 501.33 (M+)<br>$^1$H NMR (300 MHz, DMSO-$d_6$) δ ppm 7.78-7.95 (m, 2 H), 7.51-7.66 (m, 2 H), 7.27-7.51 (m, 5 H), 6.96-7.19 (m, 2 H), 6.68-6.82 (m, 2 H), 6.50-6.66 (m, 1 H), 6.36 (d, 1 H), 5.38 (d, 1 H), 5.14-5.26 (m, 1 H), 5.04 (s, 2 H), 3.96-4.15 (m, 1 H), 3.44-3.75 (m, 4 H), 3.33-3.44 (m, 1 H), 2.57 (s, 3 H), 2.30-2.44 (m, 1 H), 1.79-2.14 (m, 4 H) |
| Diastereomer 1 of C50 | Single diastereomer | 76% | LC-MS (ESI POS): 487.26 (M+)<br>$^1$H NMR (300 MHz, DMSO-$d_6$) δ ppm 7.51-7.68 (m, 2 H), 7.26-7.50 (m, 5 H), 7.00-7.19 (m, 2 H), 6.85 (d, 1 H), 6.66-6.79 (m, 2 H), 6.52-6.66 (m, 1 H), 6.36 (d, 1 H), 5.38 (d, 1 H), 5.10-5.26 (m, 1 H), 4.93 (s, 2 H), 4.06 (m, 1 H), 3.45-3.72 (m, 2 H), 3.18-3.43 (m, 3 H), 2.31-2.41 (m, 1 H), 1.68-2.05 (m, 4 H) |

Example 15

Preparation of (R)-1-(2-(3-chloro-4-fluorophenyl)-2-oxoethyl)-3-((R)-2-phenyl-2-(phenylamino)acetoxy)-1-azoniabicyclo[2.2.2]octane bromide (Diastereomer 1 of C51)

Scheme 16

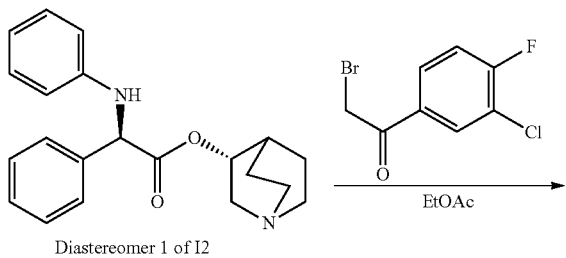

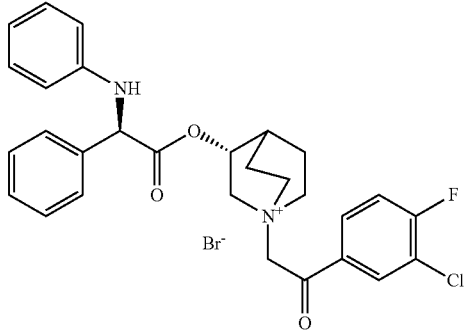

Diastereomer 1 of C51

To a solution of (R)—((R)-quinuclidin-3-yl) 2-phenyl-2-(phenylamino)acetate (diastereomer 1 of I2) (75 mg, 0.22 mmol) in EtOAc (5 ml), was added 2-bromo-1-(3-chloro-4-fluorophenyl)ethanone (61.7 mg, 0.24 mmol), and the reaction was stirred at room temperature for 15 hours. The precipitate was collected by suction filtration to obtain (R)-1-(2-(3-chloro-4-fluorophenyl)-2-oxoethyl)-3-((R)-2-phenyl-2-(phenylamino)acetoxy)-1-azoniabicyclo[2.2.2]octane bromide (120.3 mg, 92% yield).

$^1$H NMR (300 MHz, DMSO-$d_6$) δ ppm 8.21 (dd, 1H), 7.99 (ddd, 1H), 7.68 (t, 1H), 7.54-7.61 (m, 2H), 7.39-7.49 (m, 2H), 7.30-7.39 (m, 1H), 7.02-7.14 (m, 2H), 6.68-6.80 (m, 2H), 6.55-6.67 (m, 1H), 6.37 (d, 1H), 5.39 (d, 1H), 5.14-5.31 (m, 1H), 5.07 (s, 2H), 3.95-4.15 (m, 1H), 3.33-3.72 (m, 5H), 2.32-2.44 (m, 1H), 1.78-2.14 (m, 4H);

LC-MS (ESI POS): 489.31 (M+).

The compounds listed in Table 7 were prepared by working as previously described for C51, by alkylation of diastereomer 1 of I2 with 2-bromo-1-(4-morpholinophenyl)ethanone and I10.

TABLE 7

| Compound | Structure | Yield | Analytical |
|---|---|---|---|
| Diastereomer 1 of C52 | Single diastereomer | 86% | LC-MS (ESI POS): 540.38 (M+)<br>$^1$H NMR (300 MHz, DMSO-$d_6$) δ ppm 7.70-7.96 (m, 2 H), 7.51-7.70 (m, 2 H), 7.23-7.51 (m, 3 H), 6.89-7.23 (m, 4 H), 6.67-6.87 (m, 2 H), 6.48-6.67 (m, 1 H), 6.37 (d, 1 H), 5.38 (d, 1 H), 5.09-5.26 (m, 1 H), 4.98 (d, 1 H), 4.91 (d, 1 H), 3.91-4.24 (m, 1 H), 3.70-3.81 (m, 4 H), 3.45-3.70 (m, 4 H), 3.34-3.42 (m, 5 H), 2.30-2.41 (m, 1 H), 1.77-2.13 (m, 4 H) |
| Diastereomer 1 of C53 | Single diastereomer | 93% | LC-MS (ESI POS): 489.24 (M+)<br>$^1$H NMR (300 MHz, DMSO-$d_6$) δ ppm 7.76 (dd, 1 H), 7.68 (dd, 1 H), 7.53-7.61 (m, 2 H), 7.27-7.47 (m, 3 H), 6.99-7.15 (m, 3 H), 6.69-6.78 (m, 2 H), 6.55-6.64 (m, 1 H), 6.36 (d, 1 H), 5.38 (d, 1 H), 5.13-5.24 (m, 1 H), 4.97 (s, 2 H), 3.95-4.13 (m, 1 H), 3.34-3.76 (m, 5 H), 2.30-2.42 (m, 1 H), 1.77-2.14 (m, 4 H) |

Example 16

Preparation of (R)-1-(2-(4-(diethylamino)phenyl)-2-oxoethyl)-3-((R)-2-phenyl-2-(phenylamino)acetoxy)-1-azoniabicyclo[2.2.2]octane bromide (Diastereomer 1 of C54)

Scheme 17

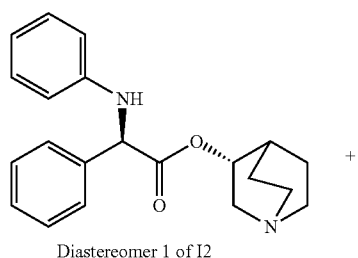

Diastereomer 1 of I2

+

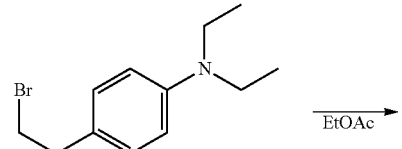

-continued

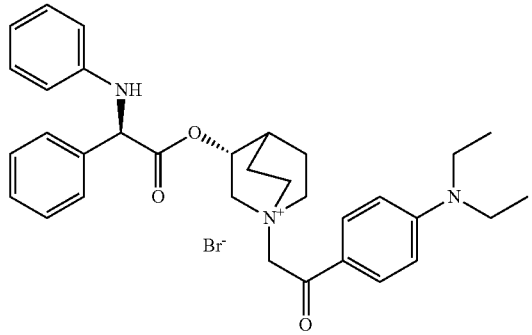

Diastereomer 1 of C54

To a solution of (R)—((R)-quinuclidin-3-yl) 2-phenyl-2-(phenylamino)acetate (diastereomer 1 of I2) (75 mg, 0.22 mmol) in EtOAc (5 ml), was added 2-bromo-1-(4-(diethylamino)phenyl)ethanone (66.3 mg, 0.24 mmol), and the reaction was stirred at room temperature for 15 hours. The solvent was evaporated and the crude was triturated with i-Pr$_2$O to obtain (R)-1-(2-(4-(diethylamino)phenyl)-2-oxoethyl)-3-((R)-2-phenyl-2(phenylamino)acetoxy)-1-azoniabicyclo[2.2.2]octane bromide (129.7 mg, 96% yield).

$^1$H NMR (300 MHz, DMSO-d$_6$) δ ppm 7.69-7.83 (m, 2H), 7.51-7.63 (m, 2H), 7.27-7.49 (m, 3H), 7.02-7.17 (m, 2H), 6.68-6.83 (m, 4H), 6.54-6.64 (m, 1H), 6.36 (d, 1H), 5.38 (d, 1H), 5.13-5.26 (m, 1H), 4.90 (d, 1H), 4.83 (d, 1H), 3.94-4.18 (m, 1H), 3.49-3.74 (m, 4H), 3.46 (q, 4H), 3.33-3.42 (m, 1H), 2.30-2.41 (m, 1H), 1.73-2.16 (m, 4H), 1.13 (t, 6H);

LC-MS (ESI POS): 526.39 (M+).

The compound C55 in Table 8 was prepared as previously described for C54, by alkylation of diastereomer 1 of I2 with 2-bromo-1-(4-(trifluoromethyl)phenyl)ethanone.

TABLE 8

| Compound | Structure | Yield | Analytical |
|---|---|---|---|
| Diastereomer 1 of C55 | Single diastereomer | 93% | LC-MS (ESI POS): 523.28 (M+)<br>$^1$H NMR (300 MHz, DMSO-d$_6$) δ ppm 8.10-8.19 (m, 2 H), 7.96-8.07 (m, 2 H), 7.54-7.66 (m, 2 H), 7.30-7.51 (m, 3 H), 7.04-7.21 (m, 2 H), 6.68-6.81 (m, 2 H), 6.53-6.68 (m, 1 H), 6.37 (d, 1 H), 5.39 (d, 1 H), 5.19-5.29 (m, 1 H), 5.16 (s, 2 H), 4.02-4.17 (m, 1 H), 3.54-3.77 (m, 3 H), 3.35-3.54 (m, 2 H), 2.32-2.44 (m, 1 H), 1.76-2.20 (m, 4 H) |

Example 17

Preparation of (R)-1-(2-(4-(ethoxycarbonyl)phenyl)-2-oxoethyl)-3-((R)-2-phenyl-2-(phenylamino)acetoxy)-1-azoniabicyclo[2.2.2]octane bromide (Diastereomer 1 of C56)

Scheme 18

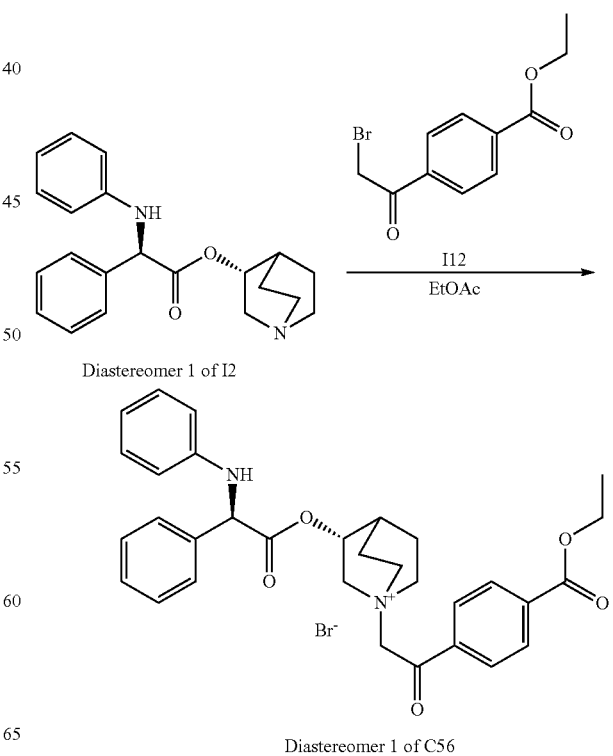

Diastereomer 1 of C56

To a solution of (R)—((R)-quinuclidin-3-yl) 2-phenyl-2-(phenylamino)acetate (diastereomer 1 of I2) (75 mg, 0.22 mmol) in EtOAc (5 ml), was added ethyl 4-(2-bromoacetyl)benzoate (I12) (66.5 mg, 0.24 mmol), and the reaction was stirred at room temperature for 15 hours. The solvent was evaporated and the crude was triturated with i-Pr$_2$O-EtOAc (1/1) to obtain (R)-1-(2-(4-(ethoxycarbonyl)phenyl)-2-oxo-ethyl)-3-((R)-2-phenyl-2-(phenylamino)acetoxy)-1-azoniabicyclo[2.2.2]octane bromide (128.5 mg, 95% yield).

$^1$H NMR (300 MHz, DMSO-d$_6$) δ ppm 8.11-8.20 (m, 2H), 8.01-8.11 (m, 2H), 7.50-7.66 (m, 2H), 7.29-7.49 (m, 3H), 7.03-7.18 (m, 2H), 6.68-6.81 (m, 2H), 6.55-6.65 (m, 1H), 6.37 (d, 1H), 5.39 (d, 1H), 5.18-5.29 (m, 1H), 5.15 (s, 2H), 4.38 (q, 2 H), 3.97-4.17 (m, 1 H), 3.34-3.75 (m, 5 H), 2.32-2.45 (m, 1 H), 1.77-2.18 (m, 4 H), 1.36 (t, 3H);

LC-MS (ESI POS): 527.38 (M+).

The compound C57 in Table 9 was prepared as previously described for C56, by alkylation of diastereomer 1 of I2 with I13.

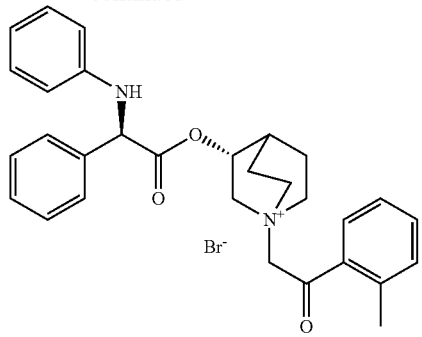

Diastereomer 1 of C58

To a solution of (R)—((R)-quinuclidin-3-yl) 2-phenyl-2-(phenylamino)acetate (diastereomer 1 of I2) (55 mg, 0.16 mmol) in EtOAc (5 ml), was added 2-bromo-1-o-tolylethanone (41.8 mg, 0.20 mmol), and the reaction was stirred at room temperature for 15 hours. The precipitate was collected by suction filtration to obtain (R)-1-(2-oxo-2-o-tolylethyl)-3-((R)-2-phenyl-2-(phenylamino)acetoxy)-1-azoniabicyclo[2.2.2]octane bromide (76.0 mg, 85% yield).

$^1$H NMR (300 MHz, DMSO-d$_6$) δ ppm 7.75-7.87 (m, 1H), 7.50-7.67 (m, 3H), 7.29-7.50 (m, 5H), 7.03-7.18 (m, 2H), 6.67-6.85 (m, 2H), 6.53-6.67 (m, 1H), 6.37 (d, 1H), 5.39 (d, 1H), 5.16-5.27 (m, 1H), 4.99 (s, 2H), 3.96-4.15 (m, 1H), 3.55-3.73 (m, 3H), 3.50 (d, 1H), 3.36-3.45 (m, 1H), 2.46 (s, 3H), 2.33-2.40 (m, 1H), 1.78-2.13 (m, 4H);

LC-MS (ESI POS): 469.31 (M+).

The compounds listed in Table 10 were prepared by working as previously described for C58, by alkylation of diastereomer 1 of I2 with I16 and commercially available alkylating agents.

TABLE 9

| Compound | Structure | Yield | Analytical |
|---|---|---|---|
| Diastereomer 1 of C57 Single diastereomer | | 72% | LC-MS (ESI POS): 555.35 (M$^+$) $^1$H NMR (300 MHz, DMSO-d$_6$) δ ppm 8.11-8.18 (m, 2 H), 8.03-8.11 (m, 2 H), 7.53-7.65 (m, 2 H), 7.39-7.50 (m, 2 H), 7.30-7.39 (m, 1 H), 7.04-7.15 (m, 2 H), 6.70-6.78 (m, 2 H), 6.56-6.64 (m, 1 H), 6.37 (d, 1 H), 5.39 (d, 1 H), 5.17-5.29 (m, 1 H), 5.14 (s, 2 H), 4.34 (t, 2 H), 3.99-4.15 (m, 1 H), 3.55-3.76 (m, 3 H), 3.45-3.55 (m, 1 H), 3.33-3.45 (m, 1 H), 2.33-2.41 (m, 1 H), 1.82-2.18 (m, 4 H), 1.65-1.82 (m, 2 H), 1.44 (sxt, 2 H), 0.95 (t, 3 H) |

Example 18

Preparation of (R)-1-(2-oxo-2-o-tolylethyl)-3-((R)-2-phenyl-2-(phenylamino)acetoxy)-1-azoniabicyclo[2.2.2]octane bromide (Diastereomer 1 of C58)

Scheme 19

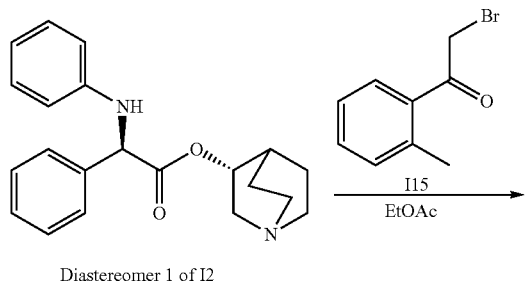

Diastereomer 1 of I2

TABLE 10

| Compound | Structure | Yield | Analytical |
|---|---|---|---|
| Diastereomer 1 of C59 | Single diastereomer | 75% | LC-MS (ESI POS): 469.41 (M+)<br>$^1$H NMR (300 MHz, DMSO-$d_6$) δ ppm 7.70-7.82 (m, 2 H), 7.54-7.64 (m, 3 H), 7.50 (t, 1 H), 7.28-7.46 (m, 3 H), 7.02-7.16 (m, 2 H), 6.69-6.79 (m, 2 H), 6.54-6.68 (m, 1 H), 6.37 (d, 1 H), 5.39 (d, 1 H), 5.16-5.27 (m, 1 H), 5.09 (s, 2 H), 3.96-4.15 (m, 1 H), 3.34-3.75 (m, 5 H), 2.41 (s, 3 H), 2.31-2.39 (m, 1 H), 1.80-2.17 (m, 4 H) |
| Diastereomer 1 of C60 | Single diastereomer | 80% | LC-MS (ESI POS): 489.31 (M+)<br>$^1$H NMR (300 MHz, DMSO-$d_6$) δ ppm 7.93 (d, 1 H), 7.47-7.66 (m, 2 H), 7.27-7.48 (m, 3 H), 7.01-7.17 (m, 3 H), 6.70-6.79 (m, 2 H), 6.52-6.67 (m, 1 H), 6.38 (d, 1 H), 5.37 (d, 1 H), 5.12-5.27 (m, 1 H), 4.93 (s, 2 H), 3.98-4.20 (m, 1 H), 3.55-3.74 (m, 3 H), 3.44-3.55 (m, 1 H), 3.32-3.42 (m, 1 H), 2.92 (q, 2 H), 2.29-2.39 (m, 1 H), 1.72-2.13 (m, 4 H), 1.28 (t, 3 H) |
| Diastereomer 1 of C61 | Single diastereomer | 80% | LC-MS (ESI POS): 499.34 (M+)<br>$^1$H NMR (300 MHz, DMSO-$d_6$) δ ppm 7.85-8.00 (m, 2 H), 7.51-7.63 (m, 2 H), 7.30-7.48 (m, 3 H), 7.03-7.18 (m, 4 H), 6.67-6.84 (m, 2 H), 6.53-6.67 (m, 1 H), 6.36 (d, 1 H), 5.38 (d, 1 H), 5.15-5.27 (m, 1 H), 5.02 (s, 2 H), 4.17 (q, 2 H), 3.97-4.12 (m, 1 H), 3.54-3.81 (m, 3 H), 3.44-3.54 (m, 1 H), 3.33-3.44 (m, 1 H), 2.30-2.44 (m, 1 H), 1.79-2.19 (m, 4 H), 1.36 (t, 3 H) |
| Diastereomer 1 of C62 | Single diastereomer | 70% | LC-MS (ESI POS): 529.23 (M+)<br>$^1$H NMR (300 MHz, DMSO-$d_6$) δ ppm 7.68 (s, 1 H), 7.52-7.65 (m, 2 H), 7.29-7.50 (m, 3 H), 6.97-7.17 (m, 2 H), 6.69-6.84 (m, 2 H), 6.55-6.65 (m, 1 H), 6.39 (d, 1 H), 5.38 (d, 1 H), 5.14-5.25 (m, 1 H), 4.89 (s, 2 H), 3.95-4.14 (m, 1 H), 3.52-3.72 (m, 3 H), 3.42-3.52 (m, 1 H), 3.33-3.42 (m, 1 H), 2.30-2.40 (m, 1 H), 1.66-2.18 (m, 4 H) |

Example 19

Preparation of (R)-1-(2-oxo-2-(4-phenoxyphenyl)ethyl)-3-((R)-2-phenyl-2-(phenylamino)acetoxy)-1-azoniabicyclo[2.2.2]octane 2,2,2-trifluoroacetate (Diastereomer 1 of C63)

Example 20

Preparation of (R)-1-(2-(biphenyl-3-yl)-2-oxoethyl)-3-((R)-2-phenyl-2-(phenylamino)acetoxy)-1-azoniabicyclo[2.2.2]octane 2,2,2-trifluoroacetate (Diastereomer 1 of C64)

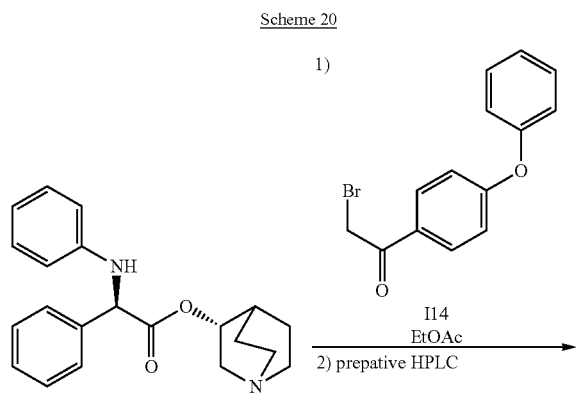

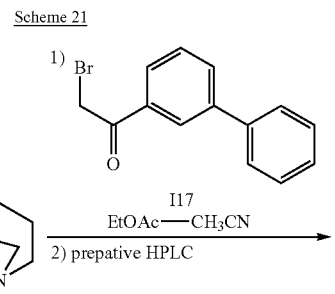

To a solution of (R)—((R)-quinuclidin-3-yl) 2-phenyl-2-(phenylamino)acetate (diastereomer 1 of I2) (75 mg, 0.22 mmol) in EtOAc (5 ml), was added 2-bromo-1-(4-phenoxyphenyl)ethanone (I14) (71.4 mg, 0.24 mmol), and the reaction was stirred at r.t. for 15 hours. The solvent was evaporated, and the crude product was purified by preparative HPLC to obtain (R)-1-(2-oxo-2-(4-phenoxyphenyl)ethyl)-3-((R)-2-phenyl-2-(phenylamino)acetoxy)-1-azoniabicyclo[2.2.2]octane 2,2,2-trifluoroacetate (53.6 mg, 36.4% yield).

$^1$H NMR (300 MHz, DMSO-d$_6$) δ ppm 7.92-8.08 (m, 2H), 7.54-7.67 (m, 2H), 7.23-7.53 (m, 6H), 7.02-7.20 (m, 6H), 6.68-6.83 (m, 2H), 6.54-6.65 (m, 1H), 6.37 (br. s., 1H), 5.38 (s, 1H), 5.16-5.29 (m, 1H), 5.04 (s, 2H), 4.01-4.18 (m, 1H), 3.22-3.74 (m, 5H), 2.31-2.42 (m, 1H), 1.69-2.20 (m, 4H);

LC-MS (ESI POS): 547.44 (M+).

To a solution of (R)—((R)-quinuclidin-3-yl) 2-phenyl-2-(phenylamino)acetate (diastereomer 1 of I2) (75 mg, 0.22 mmol) in EtOAc (5 ml) and acetonitrile (2 ml), was added 1-(biphenyl-3-yl)-2-bromoethanone (I17) (73.6 mg, 0.268 mmol). The mixture reaction was stirred at RT for 15 hours, and then the solvents were removed under vacuum. The crude was first triturated with i-Pr$_2$O-EtOAc (1/1) and then purified by preparative HPLC to obtain (R)-1-(2-(biphenyl-3-yl)-2-oxoethyl)-3-((R)-2-phenyl-2-(phenylamino)acetoxy)-1-azoniabicyclo[2.2.2]octane 2,2,2-trifluoroacetate (49.1 mg, 34.2% yield).

$^1$H NMR (300 MHz, DMSO-d$_6$) δ ppm 8.19 (t, 1H), 8.00-8.10 (m, 1H), 7.95 (dt, 1H), 7.73-7.80 (m, 2H), 7.71 (t, 1H), 7.50-7.64 (m, 4H), 7.27-7.50 (m, 4H), 6.99-7.16 (m, 2H), 6.69-6.83 (m, 2H), 6.54-6.64 (m, 1H), 6.38 (d, 1H), 5.39 (d, 1H), 5.22-5.27 (m, 1H), 5.20 (s, 2H), 3.99-4.22 (m, 1H), 3.35-3.81 (m, 5H), 2.32-2.43 (m, 1H), 1.45-2.19 (m, 4H);

LC-MS (ESI POS): 531.4 (M+).

The compound C65 in Table 11 was prepared as previously described for C64, by alkylation of diastereomer 1 of I2 with I18.

TABLE 11

| Compound | Structure | Yield | Analytical |
|---|---|---|---|
| Diastereomer 1 of C65 | 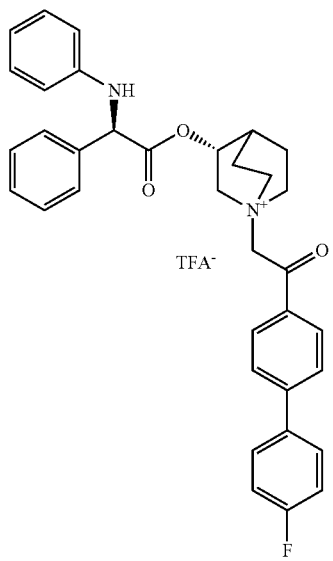 Single diastereomer | 9.5% | LC-MS (ESI POS): 549.40 (M+)<br>¹H NMR (300 MHz, DMSO-d₆) δ ppm 7.99-8.10 (m, 2 H), 7.78-7.98 (m, 4 H), 7.53-7.67 (m, 2 H), 7.30-7.51 (m, 5 H), 7.02-7.19 (m, 2 H), 6.69-6.83 (m, 2 H), 6.56-6.65 (m, 1 H), 6.37 (br. s., 1 H), 5.39 (s, 1 H), 5.17-5.29 (m, 1 H), 5.12 (s, 2 H), 4.01-4.17 (m, 1 H), 3.25-3.61 (m, 5 H), 2.32-2.42 (m, 1 H), 1.78-2.20 (m, 4 H) |

Example 21

Preparation of (R)-1-(2-oxo-2-(pyridin-2-ylamino)ethyl)-3-(R)-2-phenyl-2-(phenylamino)acetoxy)-1-azoniabicyclo[2.2.2]octane chloride (Diastereomer 1 of C66)

Scheme 22

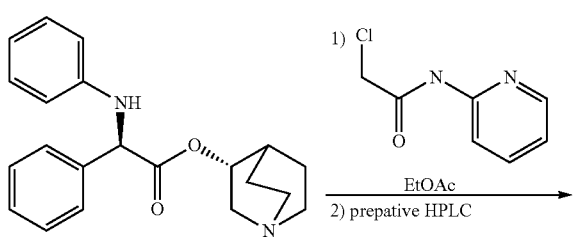

Diastereomer 1 of I2

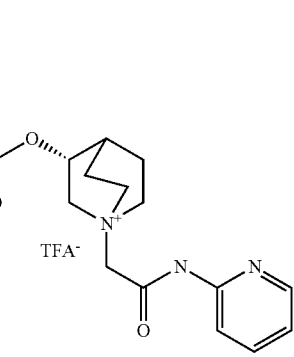

Diastereomer 1 of C66

2-Chloro-N-(pyridin-2-yl)acetamide (30.4 mg, 0.18 mmol) was added to a solution of (R)—((R)-quinuclidin-3-yl) 2-phenyl-2-(phenylamino)acetate (diastereomer 1 of I2) (60 mg, 0.18 mmol) in EtOAc (2 ml). The reaction mixture was stirred at room temperature overnight (UPLC-MS: complete conversion). The solvent was evaporated, and the crude rodcut was triturated with Et₂O (2 ml). The product was further purified by preparative HPLC to obtain (R)-1-(2-oxo-2-(pyridin-2-ylamino)ethyl)-3-((R)-2-phenyl-2-(phenylamino)acetoxy)-1-azoniabicyclo[2.2.2]octane chloride (34.5 mg, 38.2% yield).

¹H NMR (300 MHz, DMSO-d₆) δ ppm 11.06 (s, 1H), 8.39 (d, 1H), 7.96-8.10 (m, 1H), 7.73-7.96 (m, 1H), 7.50-7.65 (m, 2H), 7.27-7.50 (m, 3H), 7.18-7.27 (m, 1H), 6.98-7.11 (m, 2H), 6.66-6.77 (m, 2H), 6.50-6.66 (m, 1H), 6.37 (d, 1H), 5.37 (d, 1H), 5.09-5.25 (m, 1H), 4.22 (s, 2H), 3.97-4.13 (m, 1H), 3.35-3.75 (m, 5H), 2.30-2.39 (m, 1H), 1.63-2.15 (m, 4H);

LC-MS (ESI POS): 471.37 (M+).

Example 22

Preparation of (R)-1-(2-(4-carboxyphenyl)-2-oxoethyl)-3-((R)-2-phenyl-2-(phenylamino)acetoxy)-1-azoniabicyclo[2.2.2]octane bromide (Diastereomer 1 of C67)

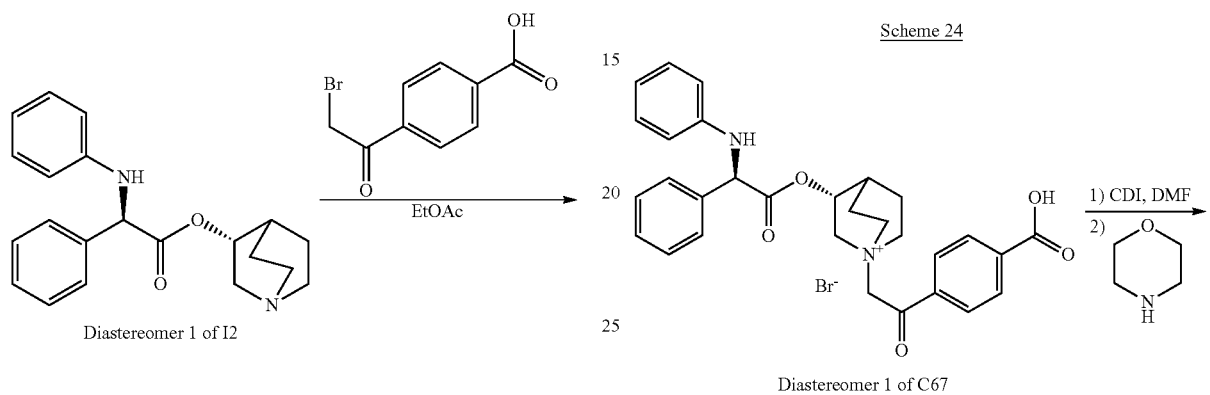

To a solution of (R)—((R)-quinuclidin-3-yl) 2-phenyl-2-(phenylamino)acetate (300 mg, 0.89 mmol) in EtOAc (5 ml), was added 4-(2-bromoacetyl)benzoic acid (238 mg, 0.98 mmol), and the reaction was stirred at r.t. for 15 hours. The precipitate was collected by suction filtration to obtain (R)-1-(2-(4-carboxyphenyl)-2-oxoethyl)-3-((R)-2-phenyl-2-(phenylamino)acetoxy)-1-azoniabicyclo[2.2.2]octane bromide (500 mg, 97% yield).

$^1$H NMR (300 MHz, DMSO-$d_6$) δ ppm 12.07-13.39 (m, 1H), 8.09-8.18 (m, 2H), 7.93-8.08 (m, 2H), 7.50-7.68 (m, 2H), 7.25-7.50 (m, 3H), 6.98-7.18 (m, 2H), 6.67-6.84 (m, 2H), 6.60 (t, 1H), 6.36 (d, 1H), 5.32-5.44 (m, 1H), 5.22 (br. s., 1H), 5.03-5.17 (m, 2H), 4.02-4.15 (m, 1H), 3.62 (d, 3H), 3.34-3.56 (m, 2H), 2.37 (br. s., 1H), 1.84-2.15 (m, 4H).

Example 23

Preparation of (R)-1-(2-(4-(morpholine-4-carbonyl)phenyl)-2-oxoethyl)-3-((R)-2-phenyl-2-(phenylamino)acetoxy)-1-azoniabicyclo[2.2.2]octane bromide (Diastereomer 1 of C68)

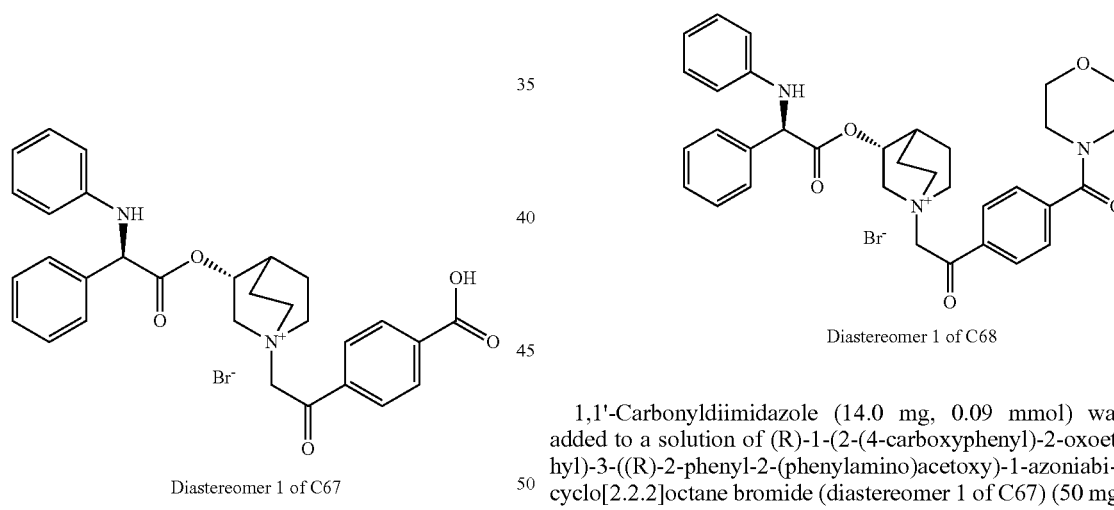

1,1'-Carbonyldiimidazole (14.0 mg, 0.09 mmol) was added to a solution of (R)-1-(2-(4-carboxyphenyl)-2-oxoethyl)-3-((R)-2-phenyl-2-(phenylamino)acetoxy)-1-azoniabicyclo[2.2.2]octane bromide (diastereomer 1 of C67) (50 mg, 0.09 mmol) in dry DMF (2 ml). The reaction mixture was stirred at room temperature for 2 hours. Then morpholine (7.52 mg, 0.09 mmol) was added, and the resulting reaction mixture was stirred at room temperature for 1 hour. DMF was evaporated and the crude was purified by preparative HPLC (eluents: $CH_3CN/H_2O$) to obtain (R)-1-(2-(4-(morpholine-4-carbonyl)phenyl)-2-oxoethyl)-3-((R)-2-phenyl-2-(phenylamino)acetoxy)-1-azoniabicyclo[2.2.2]octane bromide (18.9 mg, 33.8% yield).

$^1$H NMR (300 MHz, DMSO-$d_6$) δ ppm 7.88-8.15 (m, 2H), 7.49-7.72 (m, 4H), 7.26-7.49 (m, 3H), 7.00-7.16 (m, 2H), 6.66-6.83 (m, 2H), 6.60 (t, 1H), 6.37 (dd, 1H), 5.37 (dd, 1H), 5.23 (d, 1H), 5.04-5.20 (m, 2H), 3.92-4.24 (m, 1H), 3.60-3.63 (m, 2H), 3.34-3.85 (m, 11H), 2.32-2.41 (m, 1H), 1.48-2.20 (m, 4H);

LC-MS (ESI POS): 568.36 (M+).

Example 24

Preparation of (R)-1-(2-(4-(isopropoxycarbonyl)phenyl)-2-oxoethyl)-3-((R)-2-phenyl-2-(phenylamino)acetoxy)-1-azoniabicyclo[2.2.2]octane 2,2,2-trifluoroacetate (Diastereomer 1 of C69)

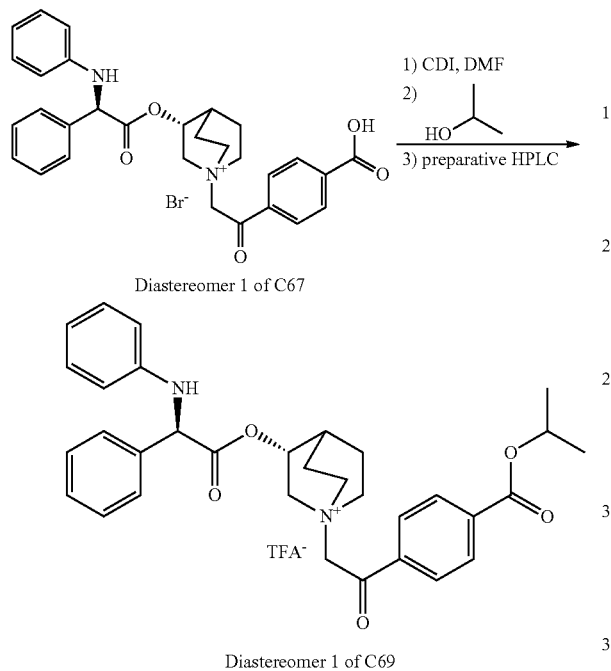

1,1'-Carbonyldiimidazole (19.6 mg, 0.12 mmol) was added to a solution of (R)-1-(2-(4-carboxyphenyl)-2-oxoethyl)-3-((R)-2-phenyl-2-(phenylamino)acetoxy)-1-azoniabicyclo[2.2.2]octane bromide (diastereomer 1 of C67) (70 mg, 0.12 mmol) in dry DMF (2 ml). The mixture reaction was stirred at room temperature for 2 hours, then propan-2-ol (7.26 mg, 0.12 mmol) was added and stirring was kept for two days (UPLC-MS: complete conversion). DMF was evaporated and the crude was purified by preparative HPLC to obtain (R)-1-(2-(4-(isopropoxycarbonyl)phenyl)-2-oxoethyl)-3-((R)-2-phenyl-2-(phenylamino)acetoxy)-1-azoniabicyclo[2.2.2]octane 2,2,2-trifluoroacetate (28.6 mg, 36.2% yield).

$^1$H NMR (300 MHz, DMSO-$d_6$) δ ppm 7.79-8.47 (m, 4H), 7.59 (dd, 2H), 7.26-7.51 (m, 3H), 7.10 (t, 2H), 6.74 (dd, 2H), 6.60 (t, 1H), 6.14-6.52 (m, 1H), 5.37 (d, 1H), 5.01-5.30 (m, 4H), 3.97-4.24 (m, 1H), 3.76 (d, 1H), 3.64 (m, 4H), 2.14 (br. s., 1H), 1.99 (d, 3H), 1.44-1.84 (m, 1H), 1.36 (d, 6H);

LC-MS (ESI POS): 541.30 (M+).

The compound C70 in Table 12 was prepared as previously described for C69, condensing diastereomer 1 of C67 with 2-(dimethylamino)ethanol.

TABLE 12

| Compound | Structure | Yield | Analytical |
|---|---|---|---|
| Diastereomer 1 of C70 | Single diastereomer | 66% | LC-MS (ESI POS): 570.33 (M$^+$)<br>$^1$H NMR (300 MHz, DMSO-$d_6$) δ ppm 9.56-9.94 (m, 1 H), 8.23 (dd, 2 H), 8.09 (t, 2 H), 7.58 (d, 2 H), 7.23-7.52 (m, 3 H), 6.91-7.23 (m, 2 H), 6.74 (d, 2 H), 6.49-6.67 (m, 1 H), 6.16-6.49 (m, 1 H), 5.17-5.55 (m, 2 H), 5.13 (s, 2 H), 4.42-4.79 (m, 2 H), 3.90-4.27 (m, 1 H), 3.58-3.84 (m, 7 H), 2.91 (br. s., 6 H), 2.16 (d, 1 H), 1.83-2.08 (m, 4 H) |

Example 25

Preparation of (R)-1-(2-(4-(methylsulfonyloxy)phenyl)-2-oxoethyl)-3-((R)-2-phenyl-2-(phenylamino)acetoxy)-1-azoniabicyclo[2.2.2]octane bromide (Diastereomer 1 of C72)

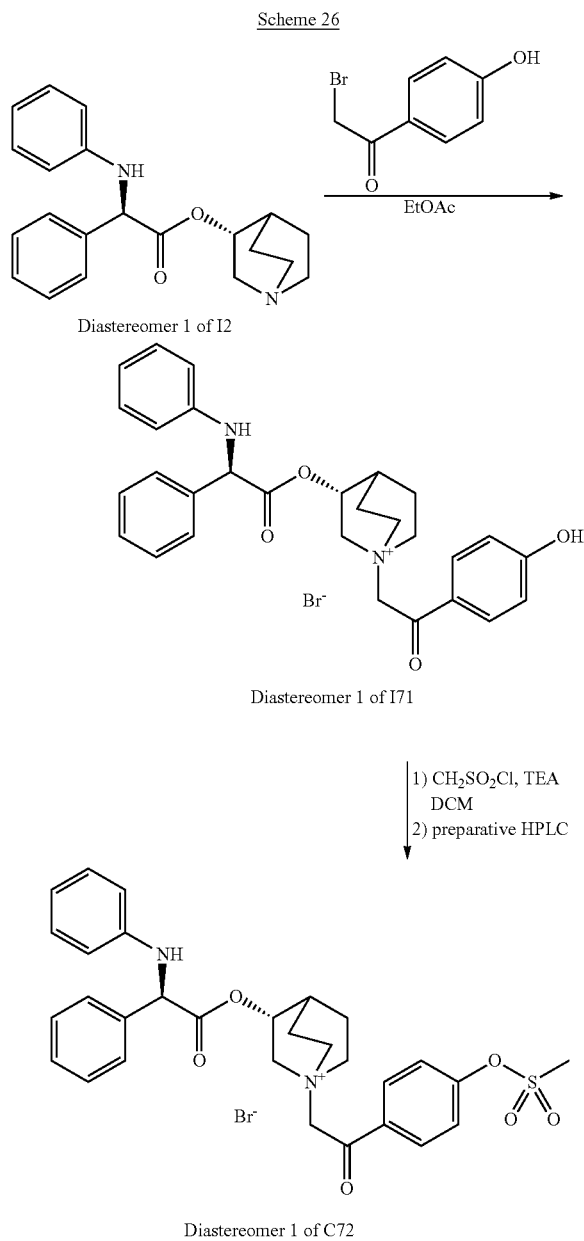

Preparation of (R)-1-(2-(4-hydroxyphenyl)-2-oxoethyl)-3-((R)-2-phenyl-2-(phenylamino)acetoxy)-1-azoniabicyclo[2.2.2]octane bromide (Diastereomer 1 of I71)

2-Bromo-1-(4-hydroxyphenyl)ethanone (256 mg, 1.19 mmol) was added to a solution of (R)—((R)-quinuclidin-3-yl) 2-phenyl-2-(phenylamino)acetate (diastereomer 1 of I2) (400 mg, 1.19 mmol) in EtOAc (15 ml). The resulting reaction was stirred at room temperature for 15 hours. The solvent was removed under vacuum, and the residue was triturated with $Et_2O$ to obtain (R)-1-(2-(4-hydroxyphenyl)-2-oxoethyl)-3-((R)-2-phenyl-2-(phenylamino)acetoxy)-1-azoniabicyclo[2.2.2]octane bromide (655 mg, 100% yield).

Preparation of (R)-1-(2-(4-(methylsulfonyloxy)phenyl)-2-oxoethyl)-3-((R)-2-phenyl-2-(phenylamino)acetoxy)-1-azoniabicyclo[2.2.2]octane bromide (Diastereomer 1 of C72)

To a solution of (R)-1-(2-(4-hydroxyphenyl)-2-oxoethyl)-3-((R)-2-phenyl-2-(phenylamino)acetoxy)-1-azoniabicyclo[2.2.2]octane bromide (diastereomer 1 of I71) (70 mg, 0.13 mmol) in DCM, were sequentially added methanesulfonyl chloride (9.9 μl, 0.13 mmol) and then TEA (17.7 μl, 0.13 mmol). The reaction mixture was stirred at room temperature for two days. The solvent was evaporated, and the crude product was purified first by trituration with $Et_2O$ and then by preparative HPLC (eluents: $CH_3CN/H_2O$) to obtain (R)-1-(2-(4-(methylsulfonyloxy)phenyl)-2-oxoethyl)-3-((R)-2-phenyl-2-(phenylamino)acetoxy)-1-azoniabicyclo[2.2.2]octane bromide (25.5 mg, 31.9% yield).

$^1$H NMR (300 MHz, DMSO-$d_6$) δ ppm 8.08 (d, 2H), 7.59 (d, 4H), 7.30-7.51 (m, 3H), 7.02-7.16 (m, 2H), 6.74 (d, 2H), 6.60 (t, 1H), 6.37 (d, 1H), 5.39 (d, 1H), 5.15-5.27 (m, 1H), 4.92-5.15 (m, 2H), 3.94-4.19 (m, 1H), 3.54-3.77 (m, 3H), 3.52 (br. s., 1H), 3.49 (s, 3H), 3.40 (dd, 1H), 2.32-2.43 (m, 1H), 1.82-2.15 (m, 4H);

LC-MS (ESI POS): 549.26 (M+).

Example 26

Preparation of (R)-1-(2-(4-acetoxyphenyl)-2-oxoethyl)-3-((R)-2-phenyl-2-(phenylamino)acetoxy)-1-azoniabicyclo[2.2.2]octane bromide (Diastereomer 1 of C73)

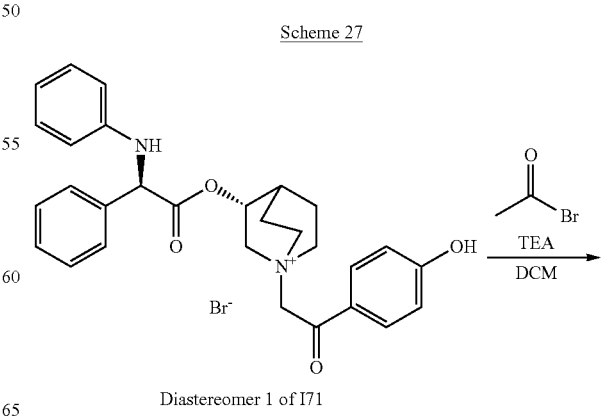

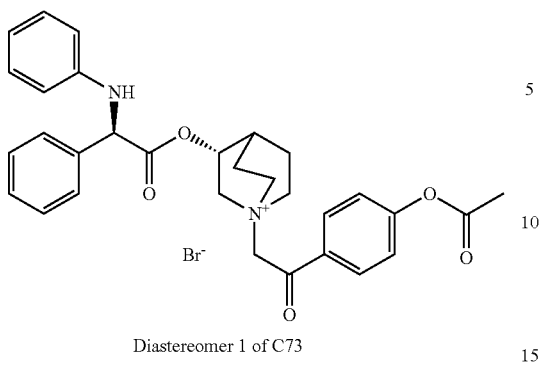

Diastereomer 1 of C73

Acetyl bromide (10 μl, 0.14 mmol) was added to a solution of (R)-1-(2-(4-hydroxyphenyl)-2-oxoethyl)-3-((R)-2-phenyl-2-(phenylamino)acetoxy)-1-azoniabicyclo[2.2.2]octane bromide (diastereomer 1 of I71) (70 mg, 0.13 mmol) in TEA (19.5 μl, 0.14 mmol) and DCM (3 ml). The reaction mixture was stirred at room temperature overnight. The solvent was evaporated, and the crude product was purified first by trituration with Et$_2$O, then by flash-chromatography (DCM/MeOH=95/5) and finally by preparative HPLC (eluents: CH$_3$CN/H$_2$O) to obtain (R)-1-(2-(4-acetoxyphenyl)-2-oxoethyl)-3-((R)-2-phenyl-2-(phenylamino)acetoxy)-1-azoniabicyclo[2.2.2]octane bromide (24 mg, 31.9% yield).

$^1$H NMR (300 MHz, DMSO-d$_6$) δ ppm 7.97-8.12 (m, 2H), 7.51-7.63 (m, 2H), 7.30-7.49 (m, 5H), 6.99-7.16 (m, 2H), 6.69-6.83 (m, 2H), 6.52-6.68 (m, 1H), 6.36 (d, 1H), 5.39 (d, 1H), 5.15-5.27 (m, 1H), 5.08 (s, 2H), 3.96-4.21 (m, 1H), 3.34-3.74 (m, 5H), 2.34-2.42 (m, 1H), 2.32 (s, 3H), 1.79-2.18 (m, 4H);

LC-MS (ESI POS): 513.39 (M+).

Example 27

Preparation of (R)-1-(2-(4-butyramidophenyl)-2-oxoethyl)-3-((R)-2-phenyl-2-(phenylamino)acetoxy)-1-azoniabicyclo[2.2.2]octane 2,2,2-trifluoroacetate (Diastereomer 1 of C75)

Scheme 28

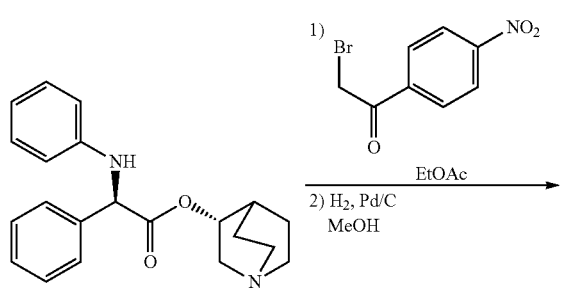

Diastereomer 1 of I2

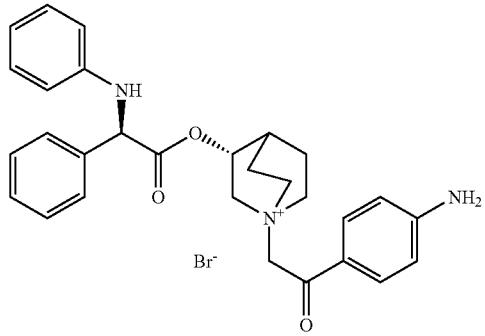

Diastereomer 1 of I74

Diastereomer 1 of C75

Preparation of (R)-1-(2-(4-aminophenyl)-2-oxoethyl)-3-((R)-2-phenyl-2-(phenylamino)acetoxy)-1-azoniabicyclo[2.2.2]octane bromide (Diastereomer 1 of I74)

2-Bromo-1-(4-nitrophenyl)ethanone (290 mg, 1.19 mmol) was added to a solution of (R)—((R)-quinuclidin-3-yl) 2-phenyl-2-(phenylamino)acetate (diastereomer 1 of I2) (400 mg, 1.19 mmol) in EtOAc (15 ml). The reaction mixture was stirred at room temperature for 2 hours. The reaction mixture was poured into a Parr's vial and diluted with MeOH. Pd/C (cat amount; about 10 mg) was added, and reaction is hydrogenated at 35 pound per square inch (psi) for 8 hours (UPLC-MS: complete conversion). The catalyst was removed by filtration, and the clear solution was concentrated under vacuum. The residue was triturated with Et$_2$O and filtered to obtain (R)-1-(2-(4-aminophenyl)-2-oxoethyl)-3-((R)-2-phenyl-2-(phenylamino)acetoxy)-1-azoniabicyclo[2.2.2]octane bromide (632 mg, 97% yield).

Preparation of (R)-1-(2-(4-butyramidophenyl)-2-oxoethyl)-3-((R)-2-phenyl-2-(phenylamino)acetoxy)-1-azoniabicyclo[2.2.2]octane 2,2,2-trifluoroacetate (Diastereomer 1 of C75)

To a solution of (R)-1-(2-(4-aminophenyl)-2-oxoethyl)-3-((R)-2-phenyl-2-(phenylamino)acetoxy)-1-azoniabicyclo[2.2.2]octane bromide (diastereomer 1 of I74) (70 mg, 0.13 mmol) in DCM, were sequentially added butyryl chloride (13.6 μl, 0.13 mmol) and then TEA (17.7 μl, 0.13 mmol). The reaction mixture was stirred at room temperature for two days. DCM was evaporated, and the crude product was purified by prep HPLC to obtain (R)-1-(2-(4-butyramidophenyl)-2-oxoethyl)-3-((R)-2-phenyl-2-(phenylamino)acetoxy)-1-azoniabicyclo[2.2.2]octane 2,2,2-trifluoroacetate (33.2 mg, 39.9% yield).

¹H NMR (300 MHz, DMSO-d₆) δ ppm 10.32 (s, 1H), 7.85-8.01 (m, 2H), 7.71-7.85 (m, 2H), 7.52-7.69 (m, 2H), 7.24-7.51 (m, 3H), 6.98-7.20 (m, 2H), 6.74 (d, 2H), 6.60 (t, 1H), 6.19-6.47 (m, 1H), 5.32-5.47 (m, 1H), 5.14-5.31 (m, 1H), 5.02 (s, 2H), 4.07 (dd, 1H), 3.40-3.77 (m, 5H), 2.31-2.39 (m, 1H), 2.35 (t, 2H), 1.81-2.16 (m, 4H), 1.63 (sxt, 2H), 0.93 (t, 3H);

LC-MS (ESI POS): 540.33 (M+).

Example 28

Preparation of (R)-1-(2-oxo-2-(4-pivalamidophenyl)ethyl)-3-((R)-2-phenyl-2-(phenylamino)acetoxy)-1-azoniabicyclo[2.2.2]octane 2,2,2-trifluoroacetate (Diastereomer 1 of C76)

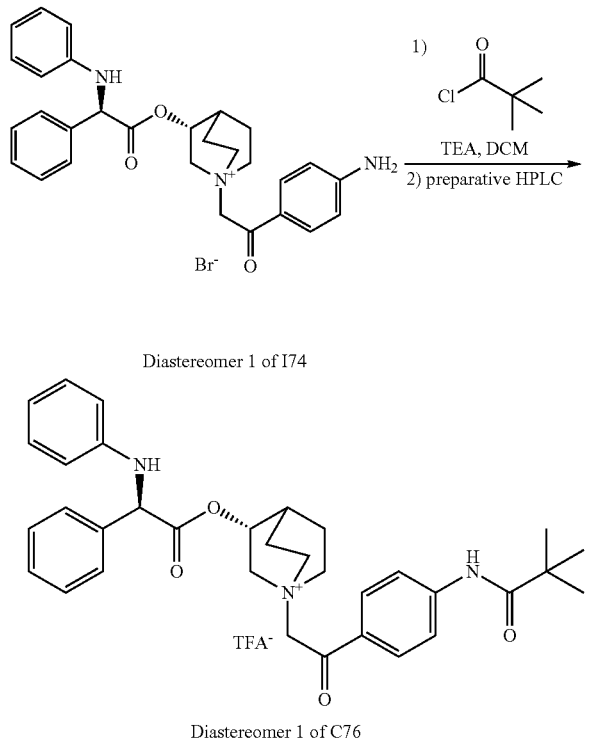

To a solution of (R)-1-(2-(4-aminophenyl)-2-oxoethyl)-3-((R)-2-phenyl-2-(phenylamino)acetoxy)-1-azoniabicyclo[2.2.2]octane bromide (diastereomer 1 of I74) (70 mg, 0.13 mmol) in DCM (3 ml), were sequentially added pivaloyl chloride (15.7 μl, 0.13 mmol) and then TEA (17.7 μl, 0.13 mmol). The reaction mixture was stirred at room temperature for two days. The solvent was evaporated and the crude product was first purified by preparative HPLC and then by flash chromatography (DCM/MeOH=97/3) to obtain (R)-1-(2-oxo-2-(4-pivalamidophenyl)ethyl)-3-((R)-2-phenyl-2-(phe-nylamino)acetoxy)-1-azoniabicyclo[2.2.2]octane 2,2,2-trifluoroacetate (14 mg, 16.5° A) yield).

¹H NMR (300 MHz, DMSO-d₆) δ ppm 9.61 (s, 1H), 7.85-8.00 (m, 4H), 7.52-7.66 (m, 2H), 7.27-7.50 (m, 3H), 6.95-7.19 (m, 2H), 6.68-6.82 (m, 2H), 6.52-6.67 (m, 1H), 6.14-6.48 (m, 1H), 5.38 (s, 1H), 5.13-5.29 (m, 1H), 5.03 (s, 2H), 3.85-4.25 (m, 1H), 3.56-3.75 (m, 3H), 3.47-3.56 (m, 2H), 2.36 (br. s., 1H), 1.81-2.12 (m, 4H), 1.25 (s, 9H);

LC-MS (ESI POS): 554.40 (M+).

Example 29

Preparation of (R)-1-(2-(4-(3-carboxypropanamido)phenyl)-2-oxoethyl)-3-((R)-2-phenyl-2-(phenylamino)acetoxy)-1-azoniabicyclo[2.2.2]octane 2,2,2-trifluoroacetate (Diastereomer 1 of C77)

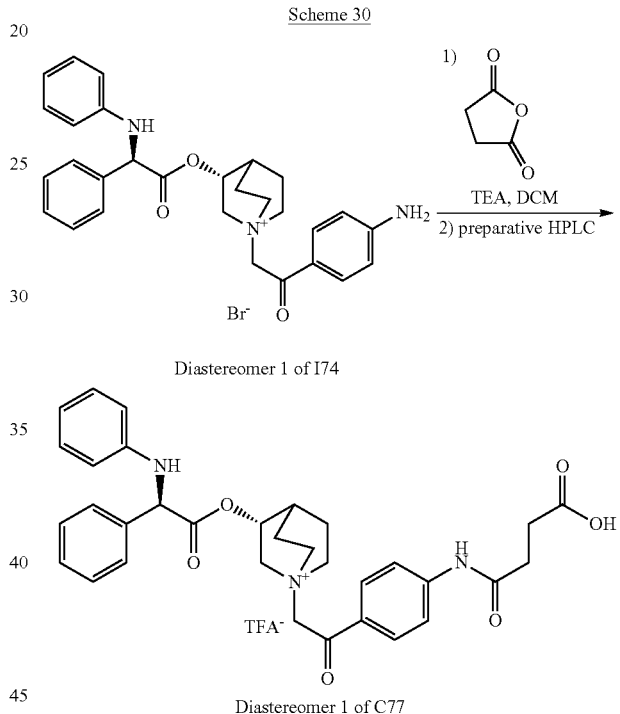

Dihydrofuran-2,5-dione (10.9 mg, 0.11 mmol) was added to a solution of (R)-1-(2-(4-aminophenyl)-2-oxoethyl)-3-((R)-2-phenyl-2-(phenylamino)acetoxy)-1-azoniabicyclo[2.2.2]octane bromide (diastereomer 1 of I74) (60 mg, 0.11 mmol) in DCM (3 ml). The reaction mixture was stirred at room temperature for 15 hours, and then it was heated at 100° C. for 1 hour under microwave irradiation. The solvent was evaporated, and the crude product was purified by preparative HPLC to obtain (R)-1-(2-(4-(3-carboxypropanamido)phenyl)-2-oxoethyl)-3-((R)-2-phenyl-2-(phenylamino)acetoxy)-1-azoniabicyclo[2.2.2]octane 2,2,2-trifluoroacetate (22.9 mg, 30.7% yield).

¹H NMR (300 MHz, DMSO-d₆) δ ppm 12.13 (br. s., 1H), 10.43 (s, 1H), 7.93 (m, 2H), 7.78 (m, 2H), 7.51-7.63 (m, 2H), 7.25-7.48 (m, 3H), 6.99-7.17 (m, 2H), 6.67-6.80 (m, 2H), 6.52-6.65 (m, 1H), 6.35 (br. s., 1H), 5.38 (br. s., 1H), 5.14-5.28 (m, 1H), 5.02 (s, 2H), 4.07 (dd, 1H), 3.54-3.75 (m, 3H), 3.45-3.54 (m, 2H), 2.59-2.68 (m, 2H), 2.55 (m, 2H), 2.36 (br. s., 1H), 1.90 (m, 4H);

LC-MS (ESI POS): 570.49 (M+).

Example 30

Preparation of (R)-1-(2-(4-(methylsulfonamido)phenyl)-2-oxoethyl)-3-((R)-2-phenyl-2-(phenylamino)acetoxy)-1-azoniabicyclo[2.2.2]octane 2,2,2-trifluoroacetate (Diastereomer 1 of C78)

Scheme 31

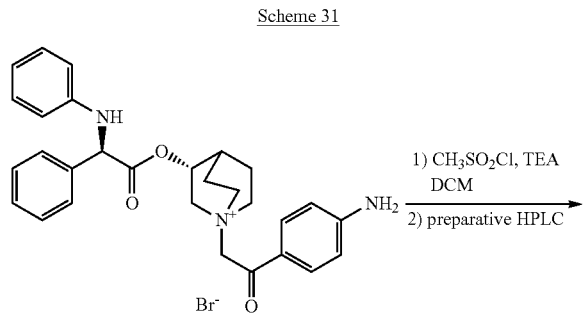

Diastereomer 1 of I74

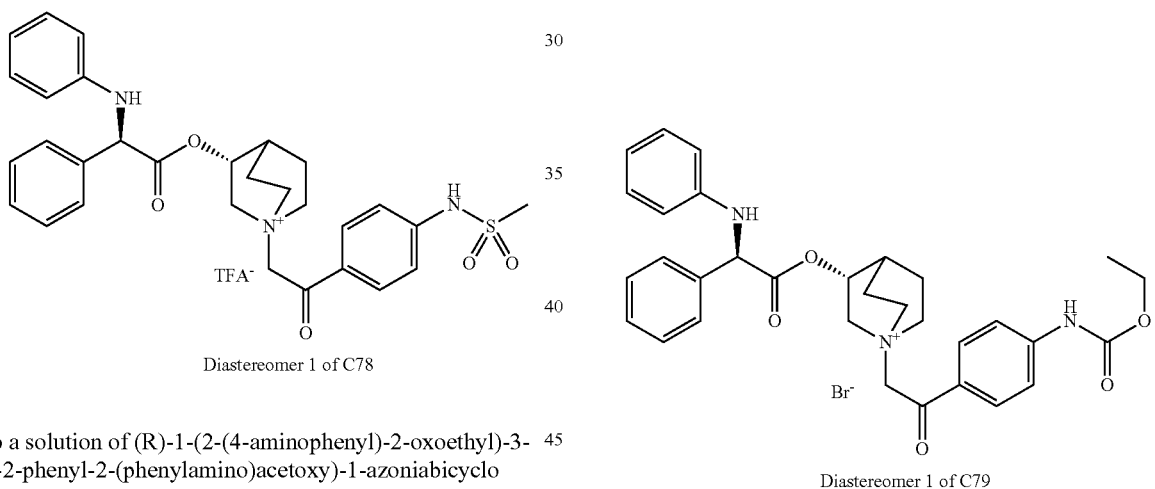

Diastereomer 1 of C78

To a solution of (R)-1-(2-(4-aminophenyl)-2-oxoethyl)-3-((R)-2-phenyl-2-(phenylamino)acetoxy)-1-azoniabicyclo[2.2.2]octane bromide (diastereomer 1 of I74) (134 mg, 0.24 mmol) in DCM (2 mL), were sequentially added methanesulfonyl chloride (20.9 µl, 0.27 mmol) and TEA (33.9 µl, 0.24 mmol). The reaction mixture was stirred at room temperature for 15 hours, and then a second portion of methanesulfonyl chloride (20.9 µl, 0.27 mmol) and TEA (33.9 µl, 0.24 mmol) were added. The reaction mixture was stirred for additional 24 hours then the solvent was evaporated. The crude product was first triturated with Et$_2$O and then purified by preparative HPLC to obtain (R)-1-(2-(4-(methylsulfonamido)phenyl)-2-oxoethyl)-3-((R)-2-phenyl-2-(phenylamino)acetoxy)-1-azoniabicyclo[2.2.2]octane 2,2,2-trifluoroacetate (24.5 mg, 15.2% yield).

$^1$H NMR (300 MHz, DMSO-d$_6$) δ ppm 10.52 (br. s., 1H), 7.86-8.00 (m, 2H), 7.52-7.65 (m, 2H), 7.27-7.49 (m, 5H), 6.99-7.19 (m, 2H), 6.67-6.79 (m, 2H), 6.54-6.64 (m, 1H), 6.37 (d, 1H), 5.33-5.43 (m, 1H), 5.12-5.26 (m, 1H), 4.96-5.10 (m, 2H), 3.98-4.17 (m, 1H), 3.33-3.75 (m, 5H), 3.14 (s, 3H), 2.31-2.42 (m, 1H), 1.77-2.07 (m, 4H);

LC-MS (ESI POS): 548.33 (M+).

Example 31

Preparation of (R)-1-(2-(4-(ethoxycarbonylamino)phenyl)-2-oxoethyl)-3-((R)-2-phenyl-2-(phenylamino)acetoxy)-1-azoniabicyclo[2.2.2]octane bromide (Diastereomer 1 of C79)

Scheme 32

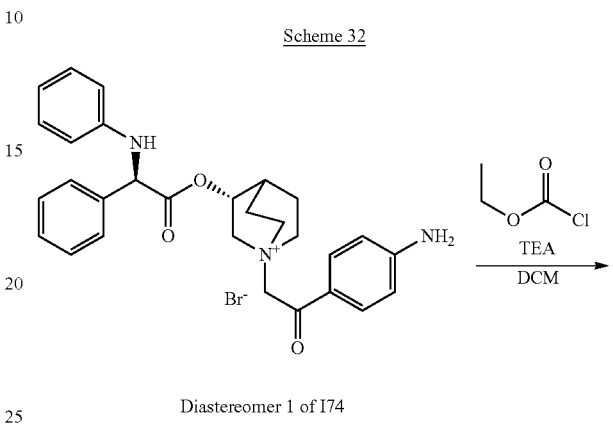

Diastereomer 1 of I74

Diastereomer 1 of C79

Ethyl carbonochloridate (10.5 µl, 0.11 mmol) was added to a solution of (R)-1-(2-(4-aminophenyl)-2-oxoethyl)-3-((R)-2-phenyl-2-(phenylamino)acetoxy)-1-azoniabicyclo[2.2.2]octane bromide (diastereomer 1 of I74) (60 mg, 0.11 mmol) in TEA (15.2 µl, 0.11 mmol) and DCM (2 mL). The reaction mixture was stirred at room temperature overnight. The solvent was evaporated under reduced pressure, and the product was purified by preparative HPLC (eluents: CH$_3$CN/H$_2$O) to obtain (R)-1-(2-(4-(ethoxycarbonylamino)phenyl)-2-oxoethyl)-3-((R)-2-phenyl-2-(phenylamino)acetoxy)-1-azoniabicyclo[2.2.2]octane bromide (14 mg, 20.6% yield).

$^1$H NMR (300 MHz, DMSO-d$_6$) δ ppm 10.18 (s, 1H), 7.91 (m, 2H), 7.66 (m, 2H), 7.50-7.62 (m, 2H), 7.28-7.47 (m, 3H), 7.00-7.17 (m, 2H), 6.70-6.80 (m, 2H), 6.55-6.64 (m, 1H), 6.36 (d, 1H), 5.38 (d, 1H), 5.14-5.27 (m, 1H), 5.01 (s, 2H), 4.18 (q, 2H), 3.99-4.13 (m, 1H), 3.35-3.75 (m, 5H), 2.36 (br. s., 1H), 1.75-2.18 (m, 4H), 1.27 (t, 3H);

LC-MS (ESI POS): 542.37 (M+).

Example 32

Preparation of (3R)-3-(2-(3-carboxyphenylamino)-2-phenylacetoxy)-1-(2-oxo-2-phenylethyl)-1-azoniabicyclo[2.2.2]octane chloride (C80)

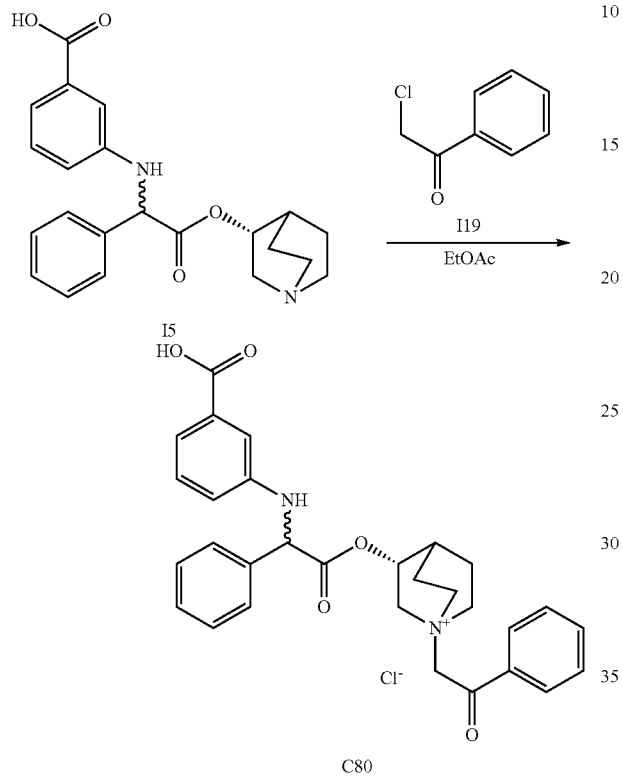

2-Chloro-1-phenylethanone (I19) (24.4 mg, 0.16 mmol) was added to a solution of 3-(2-oxo-1-phenyl-2-((R)-quinuclidin-3-yloxy)ethylamino)benzoic acid (I5) (60 mg, 0.16 mmol) in acetonitrile (1 ml) and DMF (1 ml). The reaction mixture was stirred at room temperature for 24 hours. The solvent was evaporated, and the residue was purified by preparative HPLC (eluents $CH_3CN/H_2O$) to obtain (3R)-3-(2-(3-carboxyphenylamino)-2-phenylacetoxy)-1-(2-oxo-2-phenylethyl)-1-azoniabicyclo[2.2.2]octane chloride (12 mg, 14.2% yield).

$^1$H NMR (300 MHz, DMSO-$d_6$) δ ppm 12.67 (br. s., 1H), 7.86-8.04 (m, 2H), 7.69-7.85 (m, 1H), 7.52-7.69 (m, 4H), 7.26-7.52 (m, 4H), 7.10-7.26 (m, 2H), 6.88-7.08 (m, 1H), 6.70 and 6.73 (d, 1H), 5.43 (t, 1H), 5.19-5.29 (m, 1H), 5.03-5.19 (m, 2H), 3.98-4.25 (m, 1H), 3.46-3.84 (m, 5H), 2.15 and 2.38 (br. s., 1H), 1.50-2.11 (m, 4H);

LC-MS (ESI POS): 499.26 (M+).

Example 33

Preparation of (R)-3-((S)-2-(4-fluorophenylamino)-2-phenylacetoxy)-1-(2-(4-hydroxyphenyl)-2-oxoethyl)-1-azoniabicyclo[2.2.2]octane 2,2,2-trifluoroacetate (Diastereomer 1 of C81)

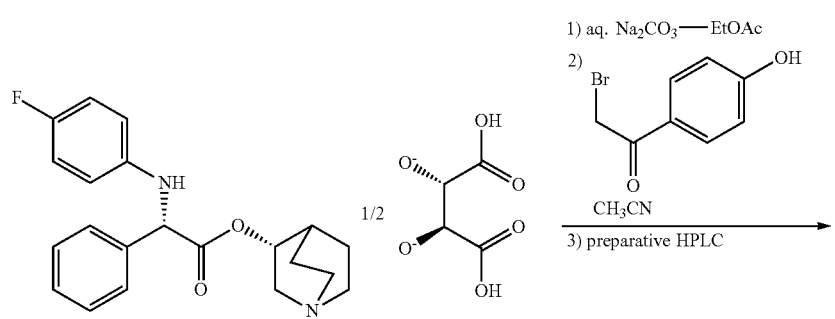

diastereomer 2 of I8

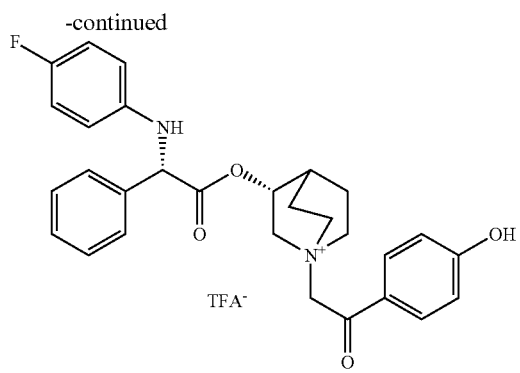

Diastereomer 1 of C81

(S)—((R)-quinuclidin-3-yl) 2-(4-fluorophenylamino)-2-phenylacetate (1S,2S)-1,2-dicarboxyethane-1,2-bis(olate) (diastereomer 2 of 18) (150 mg, 0.35 mmol) was dissolved in EtOAc (50 ml) and washed with a satured Na$_2$CO$_3$ solution (25 ml). The organic phase was dried over Na$_2$SO$_4$, and the solvent was removed in vacuo giving (S)—((R)-quinuclidin-3-yl) 2-(4-fluorophenylamino)-2-phenylacetate (60.0 mg, 0.17 mmol). This compound was dissolved in acetonitrile (2.5 ml), and 2-bromo-1-(4-hydroxyphenyl)-ethanone (36.0 mg, 0.17 mmol) was added. The reaction mixture was stirred at r.t. for 24 hours. The solvent was removed under vacuum and crude was purified by preparative HPLC to afford (R)-3-((S)-2-(4-fluorophenylamino)-2-phenylacetoxy)-1-(2-(4-hydroxyphenyl)-2-oxoethyl)-1-azoniabicyclo[2.2.2]octane 2,2,2-trifluoroacetate (23.5 mg, 23% yield).

$^1$H NMR (300 MHz, DMSO-d$_6$) δ ppm 10.73 (s, 1H), 7.81-7.96 (m, 2H), 7.52-7.62 (m, 2H), 7.27-7.49 (m, 3H), 6.87-7.00 (m, 4H), 6.66-6.80 (m, 2H), 6.36 (d, 1H), 5.32 (d, 1H), 5.17-5.25 (m, 1H), 5.07 (d, 1H), 5.01 (d, 1H), 4.01-4.17 (m, 1H), 3.44-3.86 (m, 5H), 2.06-2.18 (m, 1H), 1.84-2.07 (m, 2H), 1.66-1.84 (m, 1H), 1.45-1.66 (m, 1H);

LC-MS (ESI POS): 489.25 (M+).

Example 34

Preparation of (R)-3-((R)-2-(4-fluorophenylamino)-2-phenylacetoxy)-1-(2-(4-hydroxyphenyl)-2-oxoethyl)-1-azoniabicyclo[2.2.2]octane 2,2,2-trifluoroacetate (Diastereomer 1 of C82)

Scheme 35

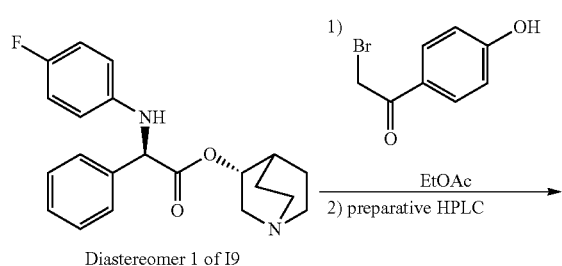

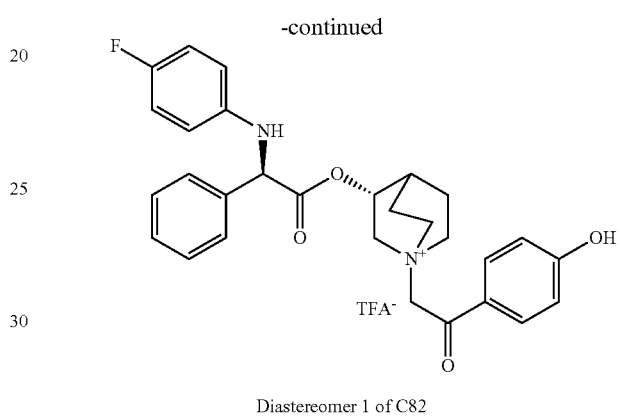

Diastereomer 1 of C82

2-Bromo-1-(4-hydroxyphenyl)ethanone (44.3 mg, 0.21 mmol) was added to a solution of (R)—((R)-quinuclidin-3-yl) 2-(4-fluorophenylamino)-2-phenylacetate (diastereomer 1 of I9) (73 mg, 0.21 mmol) in EtOAc (2 ml). The mixture was stirred at r.t. for 16 hours, and then a second portion of 2-bromo-1-(4-hydroxyphenyl)ethanone (4.4 mg, 0.02 mmol) was added. The reaction mixture was stirred at room temperature for 1 hour, and then the solvent was removed under vacuum. The residue was purified by preparative HPLC to afford the title compound (64.0 mg, 52% yield).

$^1$H NMR (300 MHz, DMSO-d$_6$) δ ppm 10.71 (br. s., 1H), 7.76-7.99 (m, 2H), 7.51-7.62 (m, 2H), 7.27-7.49 (m, 3H), 6.64-7.03 (m, 6H), 6.34 (br. s., 1H), 5.36 (s, 1H), 5.15-5.26 (m, 1H), 4.99 (s, 2H), 4.00-4.20 (m, 1H), 3.34-3.81 (m, 5H), 2.31-2.42 (m, 1H), 1.71-2.17 (m, 4H);

LC-MS (ESI POS): 489.24 (M+).

Example 35

Preparation of (R)-3-((R)-2-(4-fluorophenylamino)-2-phenylacetoxy)-1-(2-(3-hydroxyphenyl)-2-oxoethyl)-1-azoniabicyclo[2.2.2]octane 2,2,2-trifluoroacetate (Diastereomer 1 of C83)

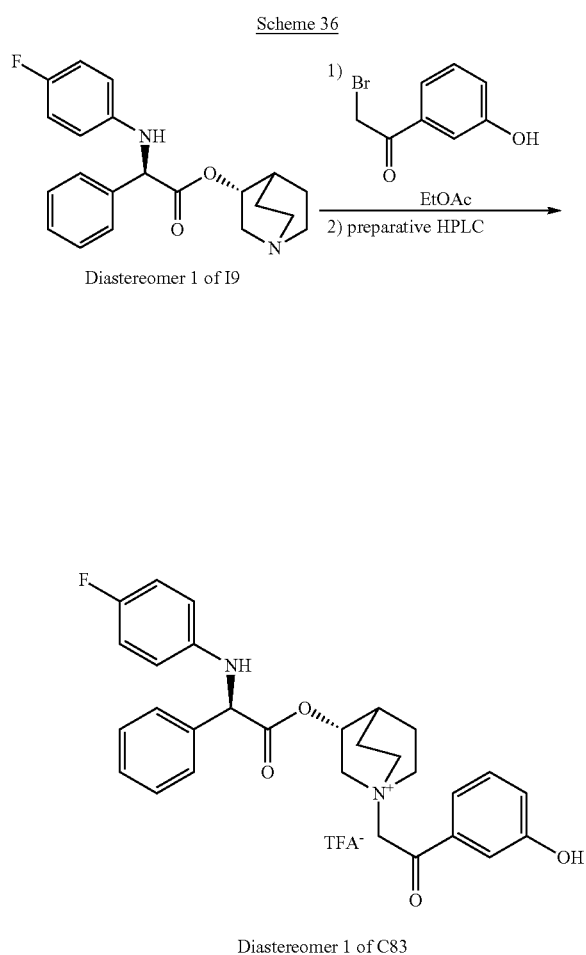

Diastereomer 1 of C83

2-Bromo-1-(3-hydroxyphenyl)ethanone (44.3 mg, 0.21 mmol) was added to a solution of (R)—((R)-quinuclidin-3-yl) 2-(4-fluorophenylamino)-2-phenylacetate (diastereomer 1 of I9) (73 mg, 0.21 mmol) in EtOAc (2 ml). The mixture was stirred at r.t. for 16 hours, and then a second portion of 2-bromo-1-(3-hydroxyphenyl)ethanone (4.4 mg, 0.02 mmol) was added. The reaction mixture was stirred at r.t. for 1 hour, and then the mixture was evaporated to dryness. The residue was triturated with DCM-Et$_2$O (1 ml/3 ml). The resulting precipitate was filtered and purified by preparative HPLC to obtain the title compound (42.9 mg, 34.6% yield).

$^1$H NMR (300 MHz, DMSO-d$_6$) δ ppm 9.98 (br. s., 1H), 7.51-7.60 (m, 2H), 7.27-7.51 (m, 6H), 7.08-7.20 (m, 1H), 6.86-7.01 (m, 2H), 6.64-6.84 (m, 2H), 6.35 (br. s., 1H), 5.33 and 5.36 (s, 1H), 5.15-5.24 (m, 1H), 5.06 and 5.12 (s, 2H), 3.97-4.11 (m, 1H), 3.32-3.63 (m, 5H), 2.30-2.42 (m, 1H), 1.41-2.20 (m, 4H);

LC-MS (ESI POS): 489.16 (M+).

Example 36

Preparation of (R)-3-((R)-2-(4-fluorophenylamino)-2-phenylacetoxy)-1-(2-(2-hydroxyphenyl)-2-oxoethyl)-1-azoniabicyclo[2.2.2]octane 2,2,2-trifluoroacetate (Diastereomer 1 of C84)

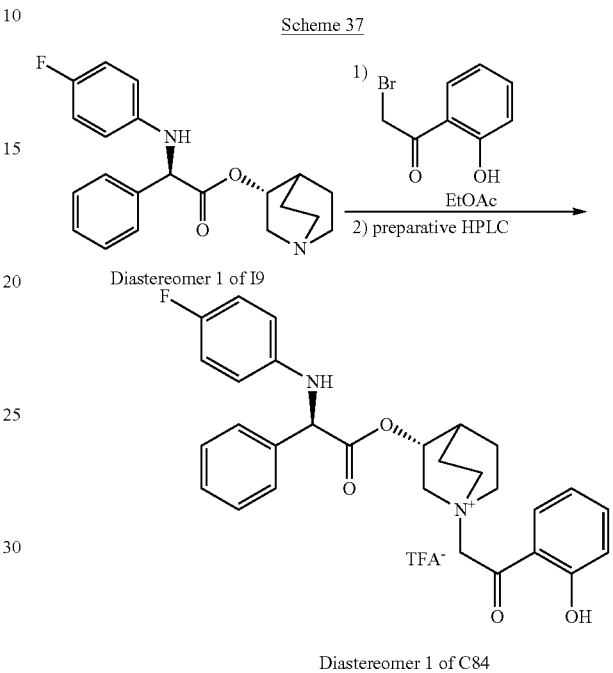

Diastereomer 1 of C84

(R)—((R)-quinuclidin-3-yl) 2-(4-fluorophenylamino)-2-phenylacetate (diastereomer 1 of I9) (73 mg, 0.21 mmol) was dissolved in EtOAc (2 ml) and 2-bromo-1-(2-hydroxyphenyl)ethanone (44.3 mg, 0.21 mmol) was added. The reaction mixture was stirred at r.t. for 16 hours. Then 2-bromo-1-(2-hydroxyphenyl)ethanone (4.4 mg, 0.02 mmol) was added again, and the reaction was stirred for an additional hour. The solvent was removed in vacuo and the residue was purified by preparative HPLC to give the title compound (25.2 mg, 20.3% yield).

$^1$H NMR (300 MHz, DMSO-d$_6$) δ ppm 11.17 and 11.21 (s, 1H), 7.77 (dd, 1H), 7.49-7.64 (m, 3H), 7.28-7.49 (m, 3H), 6.85-7.12 (m, 4H), 6.67-6.80 (m, 2H), 6.34 (br. s., 1H), 5.36 (br. s., 1H), 5.12-5.22 (m, 1H), 4.91 and 4.97 (s, 2H), 4.01-4.14 (m, 1H), 3.52-3.89 (m, 5H), 2.09-2.20 and 2.31-2.39 (m, 1H), 1.45-2.19 (m, 4H);

LC-MS (ESI POS): 489.24 (M+).

Biological Characterisation

Example 37

Examples of Radioligand Binding Assay for Cloned Human Muscarinic Receptors

CHO—K1 clone cells expressing the human M1-, M2-, M3-receptors (Euroscreen, Swissprot P11229, P08172, P20309, Genbank: J02960 respectively) were harvested in Ca$^{++}$/Mg$^{++}$ free phosphate-buffered saline and collected by centrifugation at 1500 rpm for 10 minutes, at 4° C. The pellets were resuspended in ice cold buffer A (15 mM Tris-HCl pH 7.4, 2 mM MgCl$_2$, 0.3 mM EDTA, 1 mM EGTA). Cloned cells expressing M1-, M2-, and M3-receptors were homogenized by a PIM politron (setting 5 for 15 s). The crude membrane fraction was collected by two consecutive centrifugation steps at 40000 g for 20 minutes at 4° C., separated by a washing step in buffer A. The pellets obtained from the three cell lines were finally resuspended in buffer C (75 mM Tris HCl pH 7.4, 12.5 mM MgCl$_2$, 0.3 mM EDTA, 1 mM EGTA, 250 mM sucrose) and aliquots were stored at −80° C.

The day of experiment, M1-, M2-, and M3-receptor frozen membranes were resuspended in buffer D (50 mM Tris-HCl pH 7.4, 2.5 mM MgCl$_2$, 1 mM EDTA). The non selective muscarinic radioligand [3 H]-N-methyl scopolamine (Mol. Pharmacol. 45:899-907) was used to label the M1, M2, and M3 binding sites. Binding experiments were performed in duplicate (ten point concentrations curves) in 96 well plates at radioligand concentration of 0.1 to 0.3 nM. The non-specific binding was determined in the presence of cold N-methyl scopolamine 10 µM. Samples (final volume 0.75 ml) were incubated at RT for 120 minutes for M1, 60 minutes for M2, and 90 minutes for M3 binding assay. The reaction was terminated by rapid filtration through GF/B Unifilter plates and two washes (0.75 ml) with cold buffer using a Packard Filtermate Harvester. Radioactivity on the filters was measured by a microplate scintillation counter TopCount NXT (Canberra Packard).

In the present assays, Ki values for the tested compounds were determined from the observed IC50 values according to known methods. A lower Ki value indicates that the tested compound has a higher binding affinity for the receptor.

The Ki values of the tested compounds of the invention are comprised between 0.1 nM and 1 µM. The interaction with M3 muscarinic receptors can be estimated by the results of in vitro studies which evaluated the potency of the test compounds and the offset of the inhibitory activity produced after washout of the antagonists in isolated guinea pig trachea.

Example 38

In Vitro Interaction with Guinea Pigs M3 Receptors

The potency of the antagonist activity in isolated guinea pig trachea was investigated following a method previously described by Haddad E B et al. in *Br. J. Pharmacol.*, 127, 413-420, 1999, which is incorporated herein by reference in its entirety, with few modifications.

A cumulative concentration-response curve to test antagonists was constructed on preparations precontracted by carbachol, until a complete inhibition of smooth muscle tone was achieved. The concentration of antagonist producing a 50% reversal of carbachol-induced tonic contraction (IC$_{50}$) was taken as a measure of its potency in this bioassay.

The IC$_{50}$ values for the tested compounds are comprised between 0.1 nM and 300 nM.

In the experiments aiming at assessing the offset of the inhibitory effects produced by test compounds, the minimal concentration of the test compounds known to produce a maximal inhibitory effect was administered to carbachol-precontracted preparations. As soon as the tonic contraction was completely reversed, the organ bath solution was renewed and preparations were thoroughly washed with fresh Krebs solution. Carbachol (0.3 µM) was administered again (at 30 min interval between washout and next administration) during the next 4 hours.

After 4 hours from the administration of carbachol, the inhibitory effect of the compounds of the invention, administered at a submaximal concentration (the concentration producing an inhibition of 80% of carbachol contraction) was found to be higher than 50%.

Example 39

Plasma Stability

In order to demonstrate that the compounds are degraded, stability in human plasma at 1 and 5 hours was tested for the compound of the invention. Briefly 10 µl of a stock solution 250 µM of the compound in acetonitrile were added to 1 ml of human plasma and samples were incubated at 37° C. Plasma (50 µL) was taken after 0, 1, and 5 hours of incubation and added to 140 µl of acetonitrile with addition of verapamil as internal standard (250 ng/ml). Samples were analysed by HPLC-MS/MS analysis. Plasma stability is calculated as percentage remaining after 1 and 5 hours by dividing the peak area at 1 or 5 hours by the area of the peak at time 0.

After 1 and 5 hours of incubation, plasma stability being tested for some representative compounds of the invention result to be comprised between 0 and 25%, indicating that the compounds of the invention are very unstable in human plasma.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

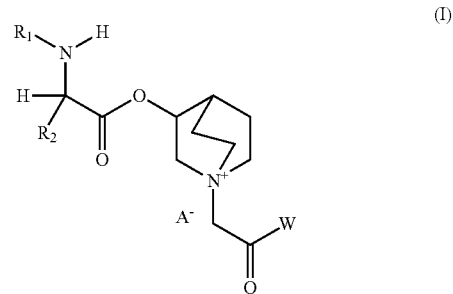

wherein:
R$_1$ is aryl optionally substituted by one or more substituents selected from the group consisting of a halogen atom and —COOH;
R$_2$ is aryl optionally substituted by one or more halogen atoms;
W is either:
(1) aryl which is substituted by one or more substituents, the same or different, selected from the group consisting of iodo, —CN, ethyl, n-propyl, isopropyl, n-butyl, isobutyl, sec-butyl, tert-butyl, pentyl, hexyl, ethoxy, n-propoxy, isopropoxy, n-butoxy, isobutoxy, sec-butoxy, tert-butoxy, pentoxy, hexoxy, ($C_1$-$C_6$)haloalkyl, ($C_1$-$C_6$)haloalkoxy, ($C_3$-$C_8$)cycloalkyl, heterocyclyl, aryl, aryloxy, haloaryl, ($C_1$-$C_6$)alkyl-NCO—($C_1$-$C_6$)alkyl, —$SR_3$, —$OSO_2R_3$, —$COR_3$, —$CO_2H$, —$OCOR_3$, —$CON(R_3)_2$, —$NHCO_2R_3$, —$NHSO_2R_3$, —NHCO—($C_1$-$C_6$)alkyl-COOH, —$CO_2$—($C_1$-$C_6$)alkyl-$N(R_3)_2$ and —CO-heterocyclyl; or (2) heteroaryl which is substituted by one or more substituents, the same or different, selected from the group consisting of fluoro, bromo, iodo, —$NO_2$, —CN, ethyl, n-propyl, isopropyl, n-butyl, isobutyl, sec-butyl, tert-butyl, pentyl, hexyl, ($C_1$-$C_6$)alkoxy, ($C_1$-$C_6$)haloalkyl, ($C_1$-$C_6$)haloalkoxy, ($C_3$-$C_8$)cycloalkyl, heterocyclyl, aryl, aryloxy, haloaryl, ($C_1$-$C_6$)alkyl-NCO—($C_1$-$C_6$)alkyl, —$OR_3$, —$N(R_3)_2$, —$SR_3$, —$OSO_2R_3$, —$COR_3$, —$OCOR_3$, —$CON(R_3)_2$, —$NHCOR_3$, —$NHCO_2R_3$, —$NHSO_2R_3$, —NHCO—($C_1$-$C_6$)alkyl-COOH, —$CO_2$—($C_1$-$C_6$)alkyl-$N(R_3)_2$ and —CO-heterocyclyl;

$R_3$ is H or ($C_1$-$C_6$)alkyl; and $A^-$ is a physiologically acceptable anion;

or a pharmaceutically acceptable salt thereof.

2. A compound or salt thereof according to claim 1, wherein $R_1$ is a phenyl group optionally substituted by one or more halogen atoms or —COOH groups.

3. A compound or salt thereof according to claim 1, wherein $R_2$ is a phenyl group optionally substituted by one or more halogen atoms.

4. A compound or salt thereof according to claim 1, wherein W is aryl which is substituted by one or more substituents, the same or different, selected from the group consisting of iodo, —$SR_3$, —$OSO_2R_3$, —$COR_3$, —$OCOR_3$, —$CON(R_3)_2$, —CN, —$NHCO_2R_3$, —$NHSO_2R_3$, (ethyl, n-propyl, isopropyl, n-butyl, isobutyl, sec-butyl, tert-butyl, pentyl, hexyl, ($C_1$-$C_6$)haloalkyl, ethoxy, n-propoxy, isopropoxy, n-butoxy, isobutoxy, sec-butoxy, tert-butoxy, pentoxy, hexoxy, ($C_1$-$C_6$)haloalkoxy, ($C_3$-$C_8$)cycloalkyl, ($C_3$-$C_8$)heterocyclyl, aryl, —NHCO—($C_1$-$C_6$)alkyl-COOH, —$CO_2$—($C_1$-$C_6$)alkyl-$N(R_3)_2$, ($C_1$-$C_6$)alkyl-NCO—($C_1$-$C_6$)alkyl, and —CO-heterocyclyl.

5. A compound or salt thereof according to claim 4, wherein W is which is substituted by one or more substituents, the same or different, selected from the group consisting of ethyl, n-propyl, isopropyl, n-butyl, isobutyl, sec-butyl, tert-butyl, pentyl, hexyl, ($C_1$-$C_6$)heterocycloalkyl aryl, iodo, —SH, —$CONH_2$, —CN, ethoxy, n-propoxy, isopropoxy, n-butoxy, isobutoxy, sec-butoxy, tert-butoxy, pentoxy, hexoxy, halo($C_1$-$C_6$)alkyl, and halo($C_1$-$C_6$)alkoxy.

6. A pharmaceutical composition, comprising at least one compound of formula (I) or salt thereof according to claim 1 and one or more pharmaceutically acceptable carriers and/or excipients.

7. A pharmaceutical composition, comprising at least one compound of formula (I) or salt thereof according to claim 2 and one or more pharmaceutically acceptable carriers and/or excipients.

8. A pharmaceutical composition, comprising at least one compound of formula (I) or salt thereof according to claim 3 and one or more pharmaceutically acceptable carriers and/or excipients.

9. A pharmaceutical composition, comprising at least one compound of formula (I) or salt thereof according to claim 4 and one or more pharmaceutically acceptable carriers and/or excipients.

10. A pharmaceutical composition, comprising at least one compound of formula (I) or salt thereof according to claim 5 and one or more pharmaceutically acceptable carriers and/or excipients.

11. A method for the treatment of a broncho-obstructive, comprising administering an effective amount of a compound or salt thereof according to claim 1 to a subject in need thereof.

12. A method according to claim 11, wherein said diseases is asthma, chronic bronchitis, or chronic obstructive pulmonary disease.

13. A combination, which comprises at least one compound of formula (I) or salt thereof according to claim 1 and one or more active ingredients selected from the group consisting of a beta2-agonist, a corticosteroid, a P38 MAP kinase inhibitor, a IKK2 inhibitor, an HNE inhibitor, a PDE4 inhibitor, a leukotriene modulator, a NSAID, and a mucus regulator.

14. A pharmaceutical composition according to claim 6, which is in a form suitable to be administered by inhalation.

15. A pharmaceutical composition according to claim 6, which is an inhalable powder, a propellant-containing metering aerosol, or a propellant-free inhalable formulations.

16. A device, comprising a pharmaceutical composition according to claim 15.

17. A device according to claim 16, which is a single- or multi-dose dry powder inhaler, a metered dose inhaler, or a soft mist nebulizer.

18. A compound or salt thereof according to claim 1, wherein W is heteroaryl which is substituted by one or more substituents, the same or different, selected from the group consisting of fluoro, bromo, iodo, —$NO_2$, —CN, ethyl, n-propyl, isopropyl, n-butyl, isobutyl, sec-butyl, tert-butyl, pentyl, hexyl, ($C_1$-$C_6$)alkoxy, ($C_1$-$C_6$)haloalkyl, ($C_1$-$C_6$)haloalkoxy, ($C_3$-$C_8$)cycloalkyl, heterocyclyl, aryl, aryloxy, haloaryl, ($C_1$-$C_6$)alkyl—NCO—($C_1$-$C_6$)alkyl, —$OR_3$, —$N(R_3)_2$, —$SR_3$, —$OSO_2R_3$, —$COR_3$, —$OCOR_3$, —$CON(R_3)_2$, —$NHCOR_3$, —$NHCO_2R_3$, —$NHSO_2R_3$, —NHCO—($C_1$-$C_6$)alkyl-COOH, —$CO_2$—($C_1$-$C_6$)alkyl-$N(R_3)_2$ and —CO-heterocyclyl.

19. A compound or salt thereof according to claim 1, wherein W is thiophenyl which is substituted by one or more substituents, the same or different, selected from the group consisting of fluoro, bromo, iodo, —$NO_2$, —CN, ethyl, n-propyl, isopropyl, n-butyl, isobutyl, sec-butyl, tert-butyl, pentyl, hexyl, ($C_1$-$C_6$)alkoxy, ($C_1$-$C_6$)haloalkyl, ($C_1$-$C_6$)haloalkoxy, ($C_3$-$C_8$)cycloalkyl, heterocyclyl, aryl, aryloxy, haloaryl, ($C_1$-$C_6$)alkyl-NCO—($C_1$-$C_6$)alkyl, —$OR_3$, —$N(R_3)_2$, —$SR_3$, —$OSO_2R_3$, —$COR_3$, —$OCOR_3$, —$CON(R_3)_2$, —$NHCOR_3$, —$NHCO_2R_3$, —$NHSO_2R_3$, —NHCO—($C_1$-$C_6$)alkyl-COOH, —$CO_2$—($C_1$-$C_6$)alkyl-$N(R_3)_2$ and —CO-heterocyclyl.

20. A compound or salt thereof according to claim 1, wherein W is aryl substituted with one or more trifluoromethyl groups.

21. A compound or salt thereof according to claim 1, wherein W is aryl substituted with one or more trifluoromethoxy groups.

22. A compound or pharmaceutically acceptable salt thereof, which is selected from the group consisting of:
 (R)-1-(2-(3-cyanophenyl)-2-oxoethyl)-3-((R)-2-phenyl-2-(phenylamino)acetoxy)-1-azoniabicyclo[2.2.2]octane bromide;
 (R)-1-(2-(2-nitrophenyl)-2-oxoethyl)-3-((R)-2-phenyl-2-(phenylamino)acetoxy)-1-azoniabicyclo[2.2.2]octane bromide;
 (R)-1-(2-(3-methoxyphenyl)-2-oxoethyl)-3-((R)-2-phenyl-2-(phenylamino)acetoxy)-1-azoniabicyclo[2.2.2]octane bromide;
 (R)-1-(2-(2-methoxyphenyl)-2-oxoethyl)-3-((R)-2-phenyl-2-(phenylamino)acetoxy)-1-azoniabicyclo[2.2.2]octane bromide;

(R)-1-(2-(2,5-dimethoxyphenyl)-2-oxoethyl)-3-((R)-2-phenyl-2-(phenylamino)acetoxy)-1-azoniabicyclo[2.2.2]octane bromide;

(R)-1-(2-(3,4-dimethoxyphenyl)-2-oxoethyl)-3-((R)-2-phenyl-2-(phenylamino)acetoxy)-1-azoniabicyclo[2.2.2]octane bromide;

(R)-1-(2-(3-carbamoyl-4-hydroxyphenyl)-2-oxoethyl)-3-((R)-2-phenyl-2-(phenylamino)acetoxy)-1-azoniabicyclo[2.2.2]octane bromide;

(R)-1-(2-(2-hydroxyphenyl)-2-oxoethyl)-3-((R)-2-phenyl-2-(phenylamino)acetoxy)-1-azoniabicyclo[2.2.2]octane bromide;

(R)-1-(2-(3-chlorophenyl)-2-oxoethyl)-3-((R)-2-phenyl-2-(phenylamino)acetoxy)-1-azoniabicyclo[2.2.2]octane bromide;

(R)-1-(2-oxo-2-(4-(trifluoromethoxy)phenypethyl)-3(R)-2-phenyl-2-(phenylamino)acetoxy)-1-azoniabicyclo[2.2.2]octane bromide;

(R)-1-(2-(5-fluoro-2-hydroxyphenyl)-2-oxoethyl)-3-((R)-2-phenyl-2-(phenylamino)acetoxy)-1-azoniabicyclo[2.2.2]octane bromide;

(R)-1-(2-(4-carboxyphenyl)-2-oxoethyl)-3-((R)-2-phenyl-2-(phenylamino)acetoxy)-1-azoniabicyclo[2.2.2]octane 2,2,2-trifluoroacetate;

(R)-1-(2-(3-nitrophenyl)-2-oxoethyl)-3-((R)-2-phenyl-2-(phenylamino)acetoxy)-1-azoniabicyclo[2.2.2]octane 2,2,2-trifluoroacetate;

R)-1-(2-(3-aminophenyl)-2-oxoethyl)-3-((R)-2-phenyl-2-(phenylamino)acetoxy)-1-azoniabicyclo[2.2.2]octane 2,2,2-trifluoroacetate;

(R)-1-(2-(2-aminophenyl)-2-oxoethyl)-3-((R)-2-phenyl-2-(phenylamino)acetoxy)-1-azoniabicyclo[2.2.2]octane 2,2,2-trifluoroacetate;

(3R)-3-(2-(3-fluorophenyl)-2-(3,4,5-trifluorophenylamino)acetoxy)-1-(2-oxo-2-(thiophen-2-yl)ethyl)-1-azoniabicyclo[2.2.2]octane chloride;

(R)-1-(2-(5-ethylthiophen-3-yl)-2-oxoethyl)-3-((R)-2-phenyl-2-(phenylamino)acetoxy)-1-azoniabicyclo[2.2.2]octane 2,2,2-trifluoroacetate;

(R)-1-(2-(naphthalen-2-yl)-2-oxoethyl)-3-((R)-2-phenyl-2-(phenylamino)acetoxy)-1-azoniabicyclo[2.2.2]octane bromide;

(R)-1-(2-(4-fluoro-2-hydroxyphenyl)-2-oxoethyl)-3-((R)-2-phenyl-2-(phenylamino)acetoxy)-1-azoniabicyclo[2.2.2]octane bromide;

(R)-1-(2-(4-(methylthio)phenyl)-2-oxoethyl)-3-((R)-2-phenyl-2-(phenylamino)acetoxy)-1-azoniabicyclo[2.2.2]octane bromide;

(R)-1-(2-(3,4-dihydroxyphenyl)-2-oxoethyl)-3-((R)-2-phenyl-2-(phenylamino)acetoxy)-1-azoniabicyclo[2.2.2]octane bromide;

(R)-1-(2-(3-chloro-4-fluorophenyl)-2-oxoethyl)-3-((R)-2-phenyl-2-(phenylamino)acetoxy)-1-azoniabicyclo[2.2.2]octane bromide;

(R)-1-(2-(3-fluoro-4-hydroxyphenyl)-2-oxoethyl)-3-((R)-2-phenyl-2-(phenylamino)acetoxy)-1-azoniabicyclo[2.2.2]octane bromide;

(R)-1-(2-oxo-2-(4-(trifluoromethyl)phenyl)ethyl)-3-((R)-2-phenyl-2-(phenylamino)acetoxy)-1-azoniabicyclo[2.2.2]octane bromide;

(R)-1-(2-(4-(ethoxycarbonyl)phenyl)-2-oxoethyl)-3((R)-2-phenyl-2-(phenylamino)acetoxy)-1-azoniabicyclo[2.2.2]octane bromide;

(R)-1-(2-(4-(butoxycarbonyl)phenyl)-2-oxoethyl)-3-((R)-2-phenyl-2-(phenylamino)acetoxy)-1-azoniabicyclo[2.2.2]octane bromide;

(R)-1-(2-oxo-2-o-tolylethyl)-3((R)-2-phenyl-2-(phenylamino)acetoxy)-1-azoniabicyclo[2.2.2]octane bromide;

((R)-1-(2-oxo-2-m-tolylethyl)-3((R)-2-phenyl-2-(phenylamino)acetoxy)-1-azoniabicyclo[2.2.2]octane bromide;

(R)-1-(2-(5-ethylthiophen-2-yl)-2-oxoethyl)-3((R)-2-phenyl-2-(phenylamino)acetoxy)-1-azoniabicyclo[2.2.2]octane chloride;

(R)-1-(2-(4-ethoxyphenyl)-2-oxoethyl)-3-((R)-2-phenyl-2-(phenylamino)acetoxy)-1-azoniabicyclo[2.2.2]octane bromide;

(R)-1-(2-(2,5-dichlorothiophen-3-yl)-2-oxoethyl)-3((R)-2-phenyl-2-(phenylamino)acetoxy)-1-azoniabicyclo[2.2.2]octane chloride;

(R)-1-(2-(4-carboxyphenyl)-2-oxoethyl)-3-((R)-2-phenyl-2-(phenylamino)acetoxy)-1-azoniabicyclo[2.2.2]octane bromide;

(R)-1-(2-(4-(isopropoxycarbonyl)phenyl)-2-oxoethyl)-3((R)-2-phenyl-2-(phenylamino)acetoxy)-1-azoniabicyclo[2.2.2]octane 2,2,2-trifluoroacetate;

(R)-1-(2-(4-(methylsulfonyloxy)phenyl)-2-oxoethyl)-3-((R)-2-phenyl-2-(phenylamino)acetoxy)-1-azoniabicyclo[2.2.2]octane bromide;

(R)-1-(2-(4-acetoxyphenyl)-2-oxoethyl)-3-((R)-2-phenyl-2-(phenylamino)acetoxy)-1-azoniabicyclo[2.2.2]octane bromide;

(R)-1-(2-(4-butyramidophenyl)-2-oxoethyl)-3-((R)-2-phenyl-2-(phenylamino)acetoxy)-1-azoniabicyclo[2.2.2]octane 2,2,2-trifluoroacetate;

(R)-1-(2-oxo-2-(4-pivalamidopheny)ethyl)-3((R)-2-phenyl-2-(phenylamino)acetoxy)-1-azoniabicyclo[2.2.2]octane 2,2,2-trifluoroacetate;

(R)-1-(2-(4-(3-carboxypropanamido)phenyl)-2-oxoethyl)-3-((R)-2-phenyl-2-(phenylamino)acetoxy)-1-azoniabicyclo[2.2.2]octane 2,2,2-trifluoroacetate;

(3R)-3-(2-(3-carboxyphenylamino)-2-phenylacetoxy)-1-(2-oxo-2-phenylethyl)-1-azoniabicyclo[2.2.2]octane chloride;

(R)-3-((S)-2-(4-fluorophenylamino)-2-phenylacetoxy)-1-(2-(4-hydroxyphenyl)-2-oxoethyl)-1-azoniabicyclo[2.2.2]octane 2,2,2-trifluoroacetate;

(R)-3-((R)-2-(4-fluorophenylamino)-2-phenylacetoxy)-1-(2-(4-hydroxyphenyl)-2-oxoethyl)-1-azoniabicyclo[2.2.2]octane 2,2,2-trifluoroacetate;

(R)-3-((R)-2-(4-fluorophenylamino)-2-phenylacetoxy)-1-(2-(3-hydroxyphenyl)-2-oxoethyl)-1-azoniabicyclo[2.2.2]octane 2,2,2-trifluoroacetate; and (R)-3-((R)-2-(4-fluorophenylamino)-2-phenylacetoxy)-1-(2-(2-hydroxyphenyl)-2-oxoethyl)-1-azoniabicyclo[2.2.2]octane 2,2,2-trifluoroacetate.

* * * * *